(12) United States Patent
Roberts et al.

(10) Patent No.: US 10,654,901 B2
(45) Date of Patent: May 19, 2020

(54) MICROORGANISMS WITH INCREASED PHOTOSYNTHETIC CAPACITY

(71) Applicants: Lumen Bioscience, Inc., Seattle, WA (US); Reliance Holding USA, Inc., Houston, TX (US)

(72) Inventors: James Roberts, Seattle, WA (US); Damian Carrieri, Seattle, WA (US); Mark Heinnickel, Seattle, WA (US)

(73) Assignees: Lumen Bioscience, Inc., Seattle, WA (US); Reliance Holding USA, Inc., Houston, TX (US)

(*) Notice: Subject to any disclaimer, the term of this patent is extended or adjusted under 35 U.S.C. 154(b) by 0 days.

(21) Appl. No.: 15/569,022

(22) PCT Filed: Apr. 22, 2016

(86) PCT No.: PCT/US2016/028785
§ 371 (c)(1),
(2) Date: Oct. 24, 2017

(87) PCT Pub. No.: WO2016/172438
PCT Pub. Date: Oct. 27, 2016

(65) Prior Publication Data
US 2018/0134755 A1   May 17, 2018

Related U.S. Application Data

(60) Provisional application No. 62/152,506, filed on Apr. 24, 2015.

(51) Int. Cl.
| | |
|---|---|
| C07K 14/195 | (2006.01) |
| C12N 9/22 | (2006.01) |
| C12N 15/11 | (2006.01) |
| C12N 15/90 | (2006.01) |

(52) U.S. Cl.
CPC ............. *C07K 14/195* (2013.01); *C12N 9/22* (2013.01); *C12N 15/11* (2013.01); *C12N 15/90* (2013.01); *C12N 2310/20* (2017.05); *C12N 2800/80* (2013.01)

(58) Field of Classification Search
CPC ...... C07K 14/195; C07K 14/62; C12N 15/74; C12N 15/11; C12N 15/90; C12N 2310/20; C12N 2800/80; C12N 9/22; C12N 1/20; C12N 9/0006; C12N 9/88; C12N 15/8243; C12N 15/09; C12N 5/10; C12N 15/70; C12N 9/1029; C12N 9/1217; C12N 15/8222; C12N 9/0067; Y02E 50/17; Y02E 50/13; C12P 7/065; C12P 7/64; C12P 7/6409; C12P 7/6436; C12P 7/649; C12P 7/06; C12R 1/89; C12Y 101/01001; C12Y 401/01001; C12Y 112/00
See application file for complete search history.

(56) References Cited

U.S. PATENT DOCUMENTS

| | | |
|---|---|---|
| 5,661,017 A | 8/1997 | Dunahay et al. |
| 2012/0252080 A1 | 10/2012 | Kristof et al. |
| 2014/0356867 A1 | 12/2014 | Peter et al. |

FOREIGN PATENT DOCUMENTS

| | | |
|---|---|---|
| WO | WO2014164566 | 10/2014 |
| WO | WO-2016/044336 A1 | 3/2016 |

OTHER PUBLICATIONS

Lazar et al. Mol. Cellular Biol. 8: 1247-1252, 1988.*
Extended European Search Report issued by the European Patent Office for Application No. 16783913.3, dated Sep. 7, 2018, 7 pages.
Hiroaki Kato et al: "Interactions Between Histidine Kinase NbIS and the Response Regulators RpaB and SrrA are Involved in the Bleaching Process of the Cyanobacterium Synechococcus elongatus PCC 7942", Plant and Cell Physiology 52(12):2115-2122 (2011).
Buikema et al., "Expression of the Anabaena hetR gene from a copper-regulated promoter leads to heterocyst differentiation under repressing conditions," Proc. Natl. Acad. Sci. USA, 2001; 98:2729-2734.
Chung et al., "Insertional inactivation studies of the csmA and csmC genes of the green sulfur bacterium Chlorobium vibrioforme 8327: the chlorosome protein CsmA is required for viability but CsmC is dispensable," FEMS Microbiol. Lett., 1998; 164:353-361.
De Philippis et al., "Exocellular polysaccharides from cyanobacteria and their possible applications," FEMS Microbiol. Reviews, 1998; 22:151-175.
Duran et al., "The efficient functioning of photosynthesis and respiration in Synechocystis sp. PCC 6803 strictly requires the presence of either cytochrome c6 or plastocyanin," J. of Biol. Chem., 2004; 279:7229-7233.
Hallmann et al., "Gene replacement by homologous recombination in the multicellular green alga Volvox carteri," Proc. Natl. Acad. USA, 1997; 94:7469-7474.
He et al., "The high light-inducible polypeptides in Synechocystis PCC6803. Expression and function in high light," J. Biol. Chem., 2001; 276:306-314.
Herranen et al., "Regulation of photosystem I reaction center genes in Synechocystis sp. strain PCC 6803 during Light acclimation," Plant Cell Physiol., 2005; 46:1484-1493.
Imamura et al., "Growth Phase-dependent Activation of Nitrogen-related Genes by a Control Network of Group 1 and Group 2 σ Factors in a Cyanobacterium," J. Biol. Chem., 2006; 281:2668-2675.
Iwai et al., "Improved genetic transformation of the thermophilic cyanobacterium, Thermosynechococcus elongatus BP-1," Plant Cell Physiol., 2004; 45:171-175.
Kindle et al., "Stable nuclear transformation of Chlamydomonas using the Chlamydomonas gene for nitrate reductase," J. Cell Biol., 109:2589-601 (1989).

(Continued)

*Primary Examiner* — Sarvamangala Devi
(74) *Attorney, Agent, or Firm* — Cooley LLP

(57) ABSTRACT

Microorganisms with increased photosynthetic capacity are described. Increased photosynthetic capacity is achieved by down-regulating activity of the RpaB pathway. The microorganisms include Cyanobacteria, including genetically-modified Cyanobacteria.

4 Claims, 17 Drawing Sheets
Specification includes a Sequence Listing.

(56) References Cited

OTHER PUBLICATIONS

Maeda et al., "cis-Acting Sequences Required for NtcB-Dependent, Nitrite-Responsive Positive Regulation of the Nitrate Assimilation Operon in the Cyanobacterium *Synechococcus* sp. Strain PCC 7942," J. Bacteriol., 1998; 180:4080-4088.

Mali et al., 2013, "RNA-guided human genome engineering via Cas9," Science, 339(6121):823-826. doi:10.1126/science.1232033.

Marin et al., J. Bacteriol., "Salt-Dependent Expression of Glucosylglycerol-Phosphate Synthase, Involved in Osmolyte Synthesis in the Cyanobacterium *Synechocystis* sp. Strain PCC 6803," 2002; 184:2870-2877.

Marin et al., Plant Physiol., "Gene Expression Profiling Reflects Physiological Processes in Salt Acclimation of *Synechocystis* sp. Strain PCC 6803," 2004; 136:3290-3300.

Mary et al., "Effects of high light on transcripts of stress-associated genes for the cyanobacteria *Synechocystis* sp. PCC 6803 and Prochlorococcus MED4 and MIT9313," Microbiol., 2004; 150:1271-1281.

Mendez-Alvarez et al., "Transformation of Chlorobium limicola by a plasmid that confers the ability to utilize thiosufate," J. Bacterial., 176:7395-7397 (1994).

Muramatsu et al., "Characterization of high-light-responsive promoters of the psaAB genes in *Synechocystis* sp. PCC 6803," Plant Cell Physiol., 47:878-890 (2006).

Perrone et al., "The Chlamydomonas IDA7 Locus Encodes a 140-kDa Dynein Intermediate Chain Required to Assemble the Il Inner Arm Complex," Molecular Biology of the Cell vol. 9, 3351-3365 (1998).

Qi et al., "Application of the Synechococcus nirA Promoter to Establish an Inducible Expression System for Engineering the Synechocystis Tocopherol Pathway," Appl. Environ. Microbiol., 2005; 71:5678-5684.

Samartzidou et al., "Transcriptional and posttranscriptional control of mRNA from lrtA, a light-repressed transcript in *Synechococcus* sp. PCC 7002," Plant Physiol., 1998; 117:225-234.

Sharp et al., "The codon Adaptation Index—a measure of directional synonymous codon usage bias, and its potential applications," 1987; Nucleic Acids Res., 15:1281-1295.

Steinbrenner et al., "Transformation of the Green Alga Haematococcus pluvialis with a Phytoene Desaturase for Accelerated Astaxanthin Biosynthesis," Appl Environ. Microbiol., 2006; 72:7477-7484.

Tan et al., "Establishment of a Micro-Particle Bombardment Transformation System for Dunaliella salina," J. Microbiol., 2005; 43:361-365.

Waditee et al., "Overexpression of a Na H antiporter confers salt tolerance on a freshwater cyanobacterium, making it capable of growth in sea water," PNAS, 2002; 99:4109-4114.

Welch et al., "Design Parameters to Control Synthetic Gene Expression in *Escherichia coli*," PLoS One vol. 4, Issue 9, 2009; e7002, 10 pages.

Welch et al., "You're one in a googol: optimizing genes for protein expression," J. R. Soc. Interface (2009) 6, S467-S476.

Zhang et al., "Optimum Conditions for Transformation of *Synechocystis* sp. PCC 6803," J. Microbiol., 2007; 45(5):241-245.

Moronta-Barrios, et al., "In vivo features of signal transduction by the essential response regulator RpaB from *Synechococcus elongatus* PCC 7942", Microbiology, vol. 158, No. 5, 2012, pp. 1229-1237.

PCT Invitation to Pay Additional Fees mailed Aug. 3, 2016 for International Application No. PCT/US16/28785, 2 pages.

Search Report and Written Opinion dated Sep. 30, 2016 for International Application No. PCT/US2016/028785, 15 pages.

\* cited by examiner

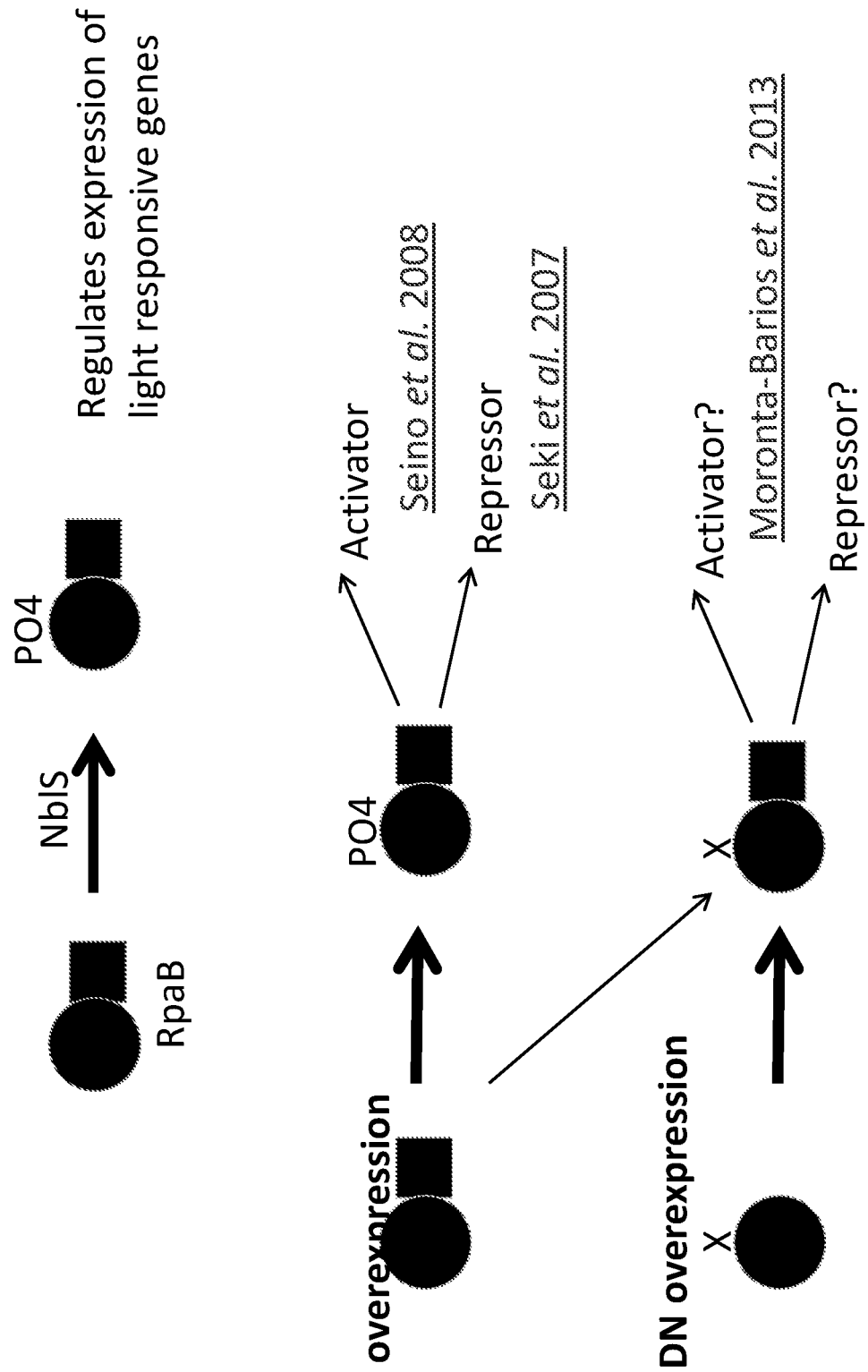

FIG. 8A

HLR1 Motif: Two direct repeats of SEQ ID NO: 1:

SEQ ID NO: 1: (G/T)TTACA(T/A)(T/A)

N-RpaB: SEQ ID NO: 2:

MENRKEKILVVDDEASIRRILETRLAMIGYEVVTAADGEEALITFRNATPDLVVLDVMMPKLDGY
GVCQELRKESDVPIIMLTALGDVADRITGLELGADDYVVKPFSPKELEARIRSVLRRVEKS

PcpcB: SEQ ID NO: 3:

tgagaaaaagtgtaaacaaatattaagaaaaagatcagaaaaatttaacaacacgtaataaaaaaatgcgtcactacgggttataa
atttacatgaaaggttaaaacacttttctgagacgattttgataaaaaagttgtcaaaaaattaagtttcttacaaatgcttaacaaaaact
tggttttaagcacaaaataagagagactaatttgcagaagttttacaaggaaatcttgaagaaaaagatctaagtaaaacgactctgttt
aaccaaaatttaacaaatttaacaaaacaaactaaatctattaggagattaactaagc PggpS: SEQ ID NO: 4:

cttgaaaaagttgaggtattaatagagcttgataaatgataataaaaacagatttagctcttattttaagggaaaaagaaataaataaaa
tattagtaaatatcaaaaatatcagcctttcaaaaataatttgactcttttcaaaaaaaaatgttatctttaaggtatgctttaaaccttaaata
cttctattggtaacactgttctcaatcttatttcagattttcccattgagcataaataaaatattaagcagaagtagaaaaggttgatattagc
aataataaaaattaacaataaaatgtgaaaacagattactactgattatttattgccatgagctaattagtaataatttgtctttttgatcga
aaaatgaaatttttaagcggaggaactgaaaatta PlrtA: SEQ ID NO: 5:

tagagtatgataaaatgacaaggaaaggattattttctcttgtttaaattctcaagattcttatgcttatttattttatgtaagtgtctcttttccttga
aatagaaagaaaaaagtggctaattttgagaaaagctaacaacgctttggttaactaaaaatcaaaagtgagattactgatcgcttaa
gaaatggagtattgatt PnbIA: SEQ ID NO: 6:

gcagttagataaataagtaatgagcgggagaaatagggggcaaatggccattcgcccctacagggaggtggcaggtgttagggtgttt
aggggatgaggtgatgagggtagagggagataaggtgtcgggtttcagatttcaggttttagaagaaagtaacgagtaattatcaact
attcactattcactattgcctgttgcccttctctccttgaaatataaaaaaatgtaaaaatatcattaagaaaagtaacaaaataaacaga
aaggttgacaaagttgacgctttaatatccgtatgttagctttataacaacgaaatcaacggaggagtgaaa PpetJ: SEQ ID NO: 7:

tatttatatataaactcgaataaaaattatcaatataaagtcaaactatatctatcctattttaactgctattggtaagtcccttaattagtgttgg
ggtgaatagattttaaaagggcaaaccccccttatcctccctcgagaggggggagggcaaaaggcaaggggcaagggaaaaatt
aagaattaagaattaaaaactccgaacacctgtaggggcgaatagccattcgcttcccctcatcccccatctccccaacaccctaag
ccccctactcgttactcatttatttacatcatttatttacatcattaagaaaagtaacaaattttgacaagtagtcttttgacaggaaaaagcaa
attctcgaagatgaaaacaatagaaaaaaattcaatcttacagtaacg

FIG. 8B

PmrgA: SEQ ID NO: 8:

agagttatatttacatagtgtgtgcgagtaagggcaacttttgtaggtagatgaataaacctcaaattactcatcttaaaagacgatattttt
aatctattcttctgtaataaaatacttctttcgatagagatatttaatacttttgagagatgaaaataatttcaataattgtcatgatagagagt
aagtgcaaataagaaaaaattgattt

PppsA: SEQ ID NO: 9:

gtgatatttggtttattctatattttccttaagtaaaaattcagtcatgagggaaacttttgttaaaatttgctttaaattaataggaagatcatta
agaaaatcttaaaaagattgagttttagatcgaaattattgaagaaaaattaacaggggttctgctcaaaattttattaaattactctactg
tagtaaaggagaaattttatt

PpstS: SEQ ID NO: 10:

ataaccaatgggacttgaattttagatccatttatttaattctattttgttacatttctttatattaatcagaattatgttactttgttttgttttatgtcgtt
accttattgaagaaagagtggatgagaaggtaaatgacggggcataaatatcgattcgttgtcagaataagctgttttattcacttaactg
gttgtttgccaatttctccctaattcccataacttgtataactaaatttaataatcaattttagtaaattaagaataggttaaaagtagtatttag
aattaagttaactttaataaatttcctgtatttttttatagaaaaaagtataaaataaaaacatatcaaaaaagtttgaaatgacaat

PrnpA: SEQ ID NO: 11:

gaatagttgataattactcgttactcattactcacttaaacctgccacctgatacctgccacctctcccccccatcacctcatcccctcaacat
tccgaaccccttgacactttgaactaaaattgtattaaagtgcaaatctggacggggttaaccagtgtgacttataatagtaaacgctgttt
tttataataaataagctaaatatttaaaaactatgagtaaatatacactaaatggtactagacgtaagcagaaaagaacctccggtttcc
gcgcccgtatgagaaccaaaaatggtagaaaagtaattcaagctcgtcgtaataagggtagaaaaagattagcagtataaaattact
gttaaataaggaagctaagtttagcattttaagtttgatattactaatcattaaatttactgtgaaatataggtgggactaccatcaaagcat
cgactgaaacggcgtttaaatttccaatctgtttatcaacagggtattcgccgctctagtcgttatttttattgtccgagggttacgg

Generalized PnirA sequence: SEQ ID NO: 12:

5'(n)$_{116}$atgcaaaaaacgaat(n)$_7$atgtgtaaaaagaaa(n)$_{15}$gtagtcaaagttac(n)$_{22}$taatgt(n)$_{55}$ccgaggacaaa(n)$_2$atg-3'

Generalized PnirA sequence with nucleotide changes in the RBS: SEQ ID NO: 13:

5'(n)$_{116}$atgcaaaaaacgaat(n)$_7$atgtgtaaaaagaaa(n)$_{15}$gtagtcaaagttac(n)$_{22}$taatgt(n)$_{55}$ggaggatcagcc(n)$_2$atg-3'

FIG. 8C

Generalized PnirA sequence with nucleotide changes in the operator region and the TATA box: SEQ ID NO: 14:

5'$(n)_{116}$atgcaaaaaacgcat$(n)_7$atgcgtaaaaagcat$(n)_{15}$gtaatcaaagttac$(n)_{22}$taatat$(n)_{55}$ccgaggacaaa$(n)_2$atg-3'

Generalized PnirA sequence with nucleotide changes in the RBS, the operator region and the TATA box: SEQ ID NO: 15:

5'$(n)_{116}$atgcaaaaaacgcat$(n)_7$atgcgtaaaaagcat$(n)_{15}$gtaatcaaagttac$(n)_{22}$taatat$(n)_{55}$ggaggatcagcc$(n)_2$atg-3'

$Co^{2+}$-inducible PcorT: SEQ ID NO: 16:

cat$(n)_7$gtttactcaaaaccttgacattgacactaatgttaaggtttaggct$(n)_{15}$caagttaaaaagcatg Modified variant of PcorT includes changes in the RBS: SEQ ID NO: 17:

cat$(n)_7$gtttactcaaaaccttgacattgacactaatgttaaggtttaggct$(n)_{15}$gaggataaaaagcatg Modified variant of PcorT includes changes in the TATA box: SEQ ID NO: 18:

cat$(n)_7$gtttactcaaaaccttgacattgactaatgttaaggtttagaat$(n)_{15}$caagttaaaaagcatg Modified variant of PcorT includes changes in the RBS and the TATA box: SEQ ID NO: 19:

cat$(n)_7$gtttactcaaaaccttgacattgacactaatgttaaggtttagaat$(n)_{15}$gaggataaaaaccatg $Zn^{2+}$-inducible PsmtA: SEQ ID NO: 20:

$(n)_8$aatacctgaataattgttcatgtgtt$(n)_4$taaaaatgtgaacaatcgttcaactattta$(n)_{12}$ggaggt$(n)_7$atg $Zn^{2+}$-inducible PsmtA with changes in the RBS: SEQ ID NO: 21:

$(n)_8$aatacctgaataattgttcatgtgtt$(n)_4$taaaaatgtgaacaatcgttcaactattta$(n)_{10}$aaggaggtgat$(n)_4$atg $Zn^{2+}$-inducible PsmtA with changes in the RBS: SEQ ID NO: 22:

22$(n)_8$aatacctgaataattgttcatgtgtt$(n)_4$taaaaatgtgaacaatcgttcaactattta$(n)_{10}$aaggaggtat$(n)_5$atg

FIG. 8D

N-RpaB Gene Sequence: SEQ ID NO: 23:

atggaaaatcgcaaggaaaaaatcctcgttgtcgacgatgaagcgagcatccggcggattcttgaaactcggttggcgatgattggtt
acgaagttgtcaccgcagccgacggcgaagaagccctcatcaccttccgcaatgctacgccggatctcgtggtgctcgatgtgatgat
gcccaagctcgatggctatggcgtttgccaagagctgcgcaaagagtcggacgttccgatcatcatgctgacagccttgggcgatgtg
gccgatcgcattacggggcttgagttgggagctgatgactacgtcgtcaaaccttctcgcctaaggaactagaagcgcgaatccgct
cggtgctgcgtcgggtcgaaaaaagctag

Reference Wild-Type RpaB Protein: SEQ ID NO: 24:

MENRKEKILVVDDEASIRRILETRLAMIGYEVVTAADGEEALITFRNATPDLVVLDVMMPKLDGY
GVCQELRKESDVPIIMLTALGDVADRITGLELGADDYVVKPFSPKELEARIRSVLRRVEKSGANG
IPSSGVIQINSIRIDTNKRQVYKGDERIRLTGMEFSLLELLVSRSGEPFSRAEILQEVWGYTPERH
VDTRVVDVHISRLRAKLEDDPGNPELILTARGTGYLFQRIVEPGEEGR

Reference Wild-Type RpaB Gene: SEQ ID NO: 25:

ttggaaaatcgcaaggaaaaaatcctcgttgtcgacgatgaagcgagcatccggcggattcttgaaactcggttggcgatgattggtta
cgaagttgtcaccgcagccgacggcgaagaagccctcatcaccttccgcaatgctacgccggatctcgtggtgctcgatgtgatgatg
cccaagctcgatggctatggcgtttgccaagagctgcgcaaagagtcggacgttccgatcatcatgctgacagccttgggcgatgtgg
ccgatcgcattacggggcttgagttgggagctgatgactacgtcgtcaaaccttctcgcctaaggaactagaagcgcgaatccgctc
ggtgctgcgtcgggtcgaaaaaagcggtgctaatggcatcccagttcgggcgtcatccagatcaacagcatccgcatcgacacca
ataagcgccaagtctacaaaggcgatgagcgcatccgtctgacgggcatggagttcagtttgttggaactgctggtcagccgctccgg
tgaacctttagccgcgccgaaatcctgcaagaggtctggggctataccccgagcgccacgtcgatacccgcgtagtcgatgtccac
atctcgcggctgcgcgccaaattggaagacgatccgggcaaccctgagctcattctgacggccccgaggaaccggctacctcttccaa
cgcatcgttgaaccgggcgaagaagggcgttag

Exemplary Homologous RpaB Protein: SEQ ID NO: 26:

MTATTPSKETILVVDDEASIRRILETRLSMIGYNVVTACDGTEALELFENTAPDLVVLDVMMPKL
DGYGVCQELRKESDVPIVMLTALGDVADRITGLELGADDYVVKPFSPKELEARIRCVLRRVEKE
SVAGIPNSGVIQVSDLRIDTNKRQVFRADERIRLTGMEFSLLELLVSRSGEPFNRGEILKEVWGY
TPERHVDTRVVDVHISRLRSKLEDDPANPELILTARGTGYLFQRIIDSVASEGP

Exemplary Homologous RpaB Protein: SEQ ID NO: 27:

MVDDEASIRRILETRLSMIGYDVVTAGDGEEALETFRKADPDLVVLDVMMPKLDGYGVCQELR
KESDVPIIMLTALGDVADRITGLELGADDYVVKPFSPKELEARIRSVLRRVDKTSASGIPSSGVIH
VANIKIDTNKRQVYKGDERIRLTGMEFSLLELLVSRSGEAFSRSEILQEVWGYTPERHVDTRVV
DVHISRLRAKLEDDPSNPELILTARGTGYLFQRIIEPGEE

FIG. 8E

Exemplary Homologous RpaB Protein: SEQ ID NO: 28:

METHKEKILVVDDEASIRRILETRLSMIGYTVVTAADGEEALTTFRQEQPDLVVLDVMMPKLDGY
GVCQELRKESDVPIIMLTALGDVADRITGLELGADDYVVKPFSPKELEARIRSVLRRIEKTNTSGI
PSSGVIQVGNIRIDTNKRQVYKGDERIRLTGMEFMLLELLVGRSGEPFSRAEILEQVWGYTPER
HVDTRVVDVHISRLRAKLEEDPSNPELILTARGTGYLFQRITEPGEASNKNQ

Arthrospira platensis RpaB Protein: SEQ ID NO: 29:

MENHKERILVVDDEASIRRILETRLSMIGYDVVTAADGEEALETFRLTEPDLVVLDVMMPKLDGY
GVCQELRKESDIPIIMLTALGDVADRITGLELGADDYVVKPFSPKELEARIRSVLRRIDKNGASGI
PSSGVIQIASIRIDTNKRQVYKGDERIRLTGMEFSLLELLVSRSGEPFSRSEILQEVWGYTPERH
VDTRVVDVHISRLRAKLEDDPSNPELILTARGTGYLFQRIIDPSEVG

Arthrospira platensis RpaB Gene: SEQ ID NO: 30:

ttggaaaaccataaggaaagaattttagttgtcgatgacgaggccagtatccgccggattttggaaactcgcctttccatgatcggttac
gatgtagtaactgccgccgacggggaggaggctttagaaaccttccgcctgacagaacctgacctcgtggttttggatgtgatgatgcc
taaactagatggctacggagtttgtcaggaattaaggaaggagtctgacatccccattattatgctcaccgccttgggggatgtcgccg
atcgcatcaccggggttagaattaggcgctgatgattatgtcgtcaaacccttttcacccaaggaactagaggcccgtatccgttccgtcct
gcgccgcattgataaaaatggcgcttctggaattcccagttctggagttatccaaattgccagtattaggattgacaccaacaagcgac
aggtttacaaaggtgatgaacgcatccgcttaaccgggatggagtttagcctattggaactcttggtcagtcggtcaggagaacccttt
cccgatccgaaattctccaggaagtttggggatatactcccgaacgccatgttgatactcgcgtcgtcgatgtgcatatttcccggctcag
agctaagttagaagatgatcctagcaacccagaactgattttgaccgctcgcggtactggctatttattccagcgcattattgatccttcag
aagtgggttga Cyanobacterium aponinum RpaB Protein: SEQ ID NO: 31:

METQKEKILVVDDEASIRRILETRLSMIGYDVVTAADGEDAIATFHETQPDLVVLDVMMP
KLDGYGVCQELRKESDIPIIMLTALGDVADRITGLELGADDYVVKPFSPKELEARIRSVL
RRVDKTGVAGIPSSGVISINSIRIDTNKRQVYKGDQRIRLTGMEFSLLELLVSKSGEPFS
RSEILQEVWGYTPERHVDTRVVDVHVSRLRAKLEDDPSNPELILTARGTGYLFQRILEP
GEKKK

FIG. 8F

*Cyanobacterium aponinum* RpaB Gene: SEQ ID NO: 32:

Ttggaaactcaaaaagagaaaattttagtagttgacgatgaagcaagtattcgccgtattttagaaactcgtctctcgatgattggttatg
atgttgtcactgccgctgatggagaagatgcgatcgcaacttttcatgaaactcaaccagatttagtggttttagacgtaatgatgcccaa
attagacggctatggagtttgtcaagaactaagaaaagaatctgatatacccattattatgttaactgctttaggagatgtagcagatcgc
attacaggtttagagctaggagcagatgattatgtggtaaaaccttctctcccaaagaattagaagcaagaatccgctctgtgttaaga
agagttgacaaaacaggagttgcaggaatacctagttcgggagttatctccattaactctatcagaattgacaccaacaaaagacag
gtttacaaaggagatcaaagaatccgcttaacaggaatggaatttagcttactagaactgcttgtaagtaaatcaggagaaccttttctc
gctcagaaatcttacaggaggtttggggatatacacctgagcgtcatgtcgatactagagttgtggacgttcacgtatcccgtttaagag
caaaattagaagatgaccctagcaatcctgaactgattttaaccgctagaggtacaggatatttgtttcaaaggatattagaaccggga
gaaaagaaaaagtag

*Synechococcus elongatus* PCC 7942 N-SrrA Gene: SEQ ID NO: 33:

atgcgatcgcttaaagctgtcgaagctccgagcctcaaggaaaaaattttagtcgtagacgacgaagctgcggtccgtcgcattttgac
tatgcgcctctcgatggctggctatcaggtggtggtcgccagcgatggccatgaagccttggcgatgtttgagcaagaagcgcccgatt
tgatcgtgttggatgtgatgctacccaaactcgatggctacggcgtttgccgtgagttgcggaagctctccgatgtaccaatcatcatgct
ctctgccctgggggatatcgccgatcgcattacagggctcgacttgggtgctgacgactatctgcccaagcccttctctcccaaggaact
ggaagcgcggatcgccacaattctgcgccggctggatgactct

*Synechococcus elongatus* PCC 7942 N-SrrA Protein: SEQ ID NO: 34:

MRSLKAVEAPSLKEKILVVDDEAAVRRILTMRLSMAGYQVVVASDGHEALAMFEQEAPDLIVLD
VMLPKLDGYGVCRELRKLSDVPIIMLSALGDIADRITGLDLGADDYLPKPFSPKELEARIATILRRL
DDS

*Synechococcus elongatus* PCC 7942 - Full Length SrrA Gene: SEQ ID NO: 35:

atgcgatcgcttaaagctgtcgaagctccgagcctcaaggaaaaaattttagtcgtagacgacgaagctgcggtccgtcg
cattttgactatgcgcctctcgatggctggctatcaggtggtggtcgccagcgatggccatgaagccttggcgatgtttgagc
aagaagcgcccgatttgatcgtgttggatgtgatgctacccaaactcgatggctacggcgtttgccgtgagttgcggaagct
ctccgatgtaccaatcatcatgctctctgccctgggggatatcgccgatcgcattacagggctcgacttgggtgctgacgact
atctgcccaagcccttctctcccaaggaactggaagcgcggatcgccacaattctgcgccggctggatgactctcccaatg
cgctatccgcccttcctccccaggggtgttgcgcatcagtgatgtagaaatcgataccaaccgccgccaagtctttcagcg
gggcgagcgggttcccctgacttacaccgaattcagcctgctggaactattgttccggcagcccggtcgggtcgtaccgcg
cgccgaaatcttggaagaactctggggctatccgccgcggcgcaatgccgacctgcgagtcgtcgatgtctatgtcgccc
gtctgcgatcaaagctcgaagccgaccccgcaatcctgagctgatcatcacagtccgcggaacaggctatacctccca
gcgcctcaaagatttaccggaagcggctggagcctag

FIG. 8G

*Synechococcus elongatus* PCC 7942 - Full Length SrrA Protein: SEQ ID NO: 36

MRSLKAVEAPSLKEKILVVDDEAAVRRILTMRLSMAGYQVVVASDGHEALAMFEQEAP
DLIVLDVMLPKLDGYGVCRELRKLSDVPIIMLSALGDIADRITGLDLGADDYLPKPFSPK
ELEARIATILRRLDDSPNALSAPSSPGVLRISDVEIDTNRRQVFQRGERVPLTYTEFSLL
ELLFRQPGRVVPRAEILEELWGYPPRRNADLRVVDVYVARLRSKLEADPRNPELIITVR
GTGYTSQRLKDLPEAAGA

*Arthrospira platensis* NIES-39 SrrA Gene: SEQ ID NO: 37:

atgaccataaaagcacggcttgacgaacggcgcaatcctgaaaaaatcctcatcgccgatgatgagtctgcaattcggc
gtattttgacaacccgtctgtcaatggtcggttacagtgttgtcgcagcagcagatggcttacaagctattgaaatgttcgatc
gcgaaagtccagacctggtagttttggatgtaatgatgccaagacttaacggttacggggtttgtcaaaaaattcgagaaat
ttctgatattcccatcattatgttaaccgccttgggagatgtagccgatcgcattaccggtttagaattgggggctgatgattac
ctcactaaacccttttctcccaaagaattggaagcccgcattcacgctatcctccgtcggttcaaagataacgcatcttcccat
gatctaagtcccgaagtcatccaagttgatactctccgcattgacaccattaaacgacgggtttacaaaggcgataaattgtt
gcccctcacatatatcgagtttaacttgctcgaactgttgtttaagcgttctggtgaagcggtttctcgttccgaaattctgcaac
aattgtggggttacaccccccgccgcattgccgatatgcgcgttgttgatgttcatgtggctcgcctacgagctaaaattgag
actgatcagcgtaatcctgagtatattctcacggttcgcggtattggctactcttcccagcgactcgcagcagtggaagaac
caattggcgcataa

*Arthrospira platensis* NIES-39 SrrA Protein: SEQ ID NO: 38:

MTIKARLDERRNPEKILIADDESAIRRILTTRLSMVGYSVVAAADGLQAIEMFDRESPDL
VVLDVMMPRLNGYGVCQKIREISDIPIIMLTALGDVADRITGLELGADDYLTKPFSPKEL
EARIHAILRRFKDNASSHDLSPEVIQVDTLRIDTIKRRVYKGDKLLPLTYIEFNLLELLFKR
SGEAVSRSEILQQLWGYTPRRIADMRVVDVHVARLRAKIETDQRNPEYILTVRGIGYS
SQRLAAVEEPIGA

FIG. 8H

*Procholorcoccus marinus SS120* SrrA Gene: SEQ ID NO: 39 atgtatgaagaaggttcatccatgcttgagaagagcaatgatgggcccggttcaaaacctgcctctctcccttctgccacaa
ttttagttgttgatgatgaaccagcagttttaaaagtcttggttaccaggcttgagttagcaggctataaagttgtttcagcttcag
atggtgaagaggctttagatgtttttcatagggaaattcctgatcttgtcgttcttgatgtaatgcttcctaagcttgatggctttgct
gtatgtaggagattgcgagctgaatcaattgtcccgattattttcttagtgctcttgaagcaatatctgagcgagtagcgggac
ttgacttgggtgctgatgattatttatctaaaccgtttagtccaaaagagcttgaagcacgtatagccacaatattgcgtagaat
gggtcctggcgcgtctgtagctgaacctagagagattcctgctgggcaaggtgtgatgaaactaggtgaattagttgtggat
acaaatcgtcgtcaggttagtcgcggtggagaaaggattggtttaacttacacagagtttagtttgcttgaattactgtttcgtg
accctgggaaagtagttcctagagcagagatacttgagcagctatggggatatcctcctaggcgtgctgctgacttaagag
ttgttgacgtttatgtagcacgtttgcgaggcaagcttgagccagatcctcgtaatccggagttaattcttactgtaagaggcat
aggttattcatctcagaggttgaatgagtttcctcctgttagctcttaa

*Procholorcoccus marinus SS120* SrrA Protein: SEQ ID NO: 40:

MYEEGSSMLEKSNDGPGSKPASLPSATILVVDDEPAVLKVLVTRLELAGYKVVSASDG
EEALDVFHREIPDLVVLDVMLPKLDGFAVCRRLRAESIVPIIFLSALEAISERVAGLDLGA
DDYLSKPFSPKELEARIATILRRMGPGASVAEPREIPAGQGVMKLGELVVDTNRRQVS
RGGERIGLTYTEFSLLELLFRDPGKVVPRAEILEQLWGYPPRRAADLRVVDVYVARLR
GKLEPDPRNPELILTVRGIGYSSQRLNEFPPVSS

Exemplary DNA Encoding Guide RNA for transcriptional interference of the nbIS gene in *Synechococcus elongatus PCC7942*: SEQ ID NO: 41:

ttggcaacaactgcgcgata

Exemplary Guide RNA for transcriptional interference of the nbIS gene in *Synechococcus elongatus PCC7942*: SEQ ID NO: 42:

uuggcaacaacugcgcgaua

FIG. 8I

Exemplary DNA sequence to drive expression of a Cas9 protein: SEQ ID NO: 43:

atggataagaaatactcaataggcttagctatcggcacaaatagcgtcggatgggcggtgatcactgatgaatataaggtt
ccgtctaaaaagttcaaggttctgggaaatacagaccgccacagtatcaaaaaaaatcttatagggggctcttttatttgaca
gtggagagacagcggaagcgactcgcctcaaacggacagctcgtagaaggtatacacgtcggaagaatcgtatttgtta
tctacaggagatttttcaaatgagatggcgaaagtagatgatagtttctttcatcgacttgaagagtcttttttggtggaagaag
ataagaagcatgaacgtcatcctattttttggaaatatagtagatgaagttgcttatcatgagaaatatccaactatctatcatct
gcgaaaaaaattggtagattctactgataaagcggatttgcgcttaatctatttggccttagcgcacatgattaagtttcgtggt
cattttttgattgagggagatttaaatcctgataatagtgatgtggacaaactatttatccagttggtacaaacctacaatcaatt
atttgaagaaaaccctattaacgcaagtggagtagatgctaaagcgattctttctgcacgattgagtaaatcaagacgatta
gaaaatctcattgctcagctccccggtgagaagaaaaatggcttatttgggaatctcattgctttgtcattgggtttgaccccta
attttaaatcaaattttgatttggcagaagatgctaaattacagctttcaaaagatacttacgatgatgatttagataaattattgg
cgcaaattggagatcaatatgctgatttgttttggcagctaagaatttatcagatgctatttactttcagatatcctaagagtaa
atactgaaataactaaggctcccctatcagcttcaatgattaaacgctacgatgaacatcatcaagacttgactcttttaaaa
gctttagttcgacaacaacttccagaaaagtataaagaaatctttttttgatcaatcaaaaaacggatatgcaggttatattgat
gggggagctagccaagaagaatttataaatttatcaaaccaattttagaaaaaatggatggtactgaggaattattggtga
aactaaatcgtgaagatttgctgcgcaagcaacggacctttgacaacggctctattcccatcaaattcacttgggtgagct
gcatgctattttgagaaggcaagaggactttatccattttaaaagacaatcgtgagaagattgaaaaaatcttgactttcg
aatcccttattatgttggtccattggcgcgtggcaatagtcgttttgcatggatgactcggaagtctgaagaaacaattcccc
atggaattttgaagaagttgtcgataaaggtgcttcagctcaatcatttattgaacgcatgacaaactttgataaaaatcttcc
aaatgaaaaagtactaccaaaacatagtttgctttatgagtattttacggtttataacgaattgacaaaggtcaaatatgttact
gaaggaatgcgaaaaccagcatttctttcaggtgaacagaagaaagccattgttgatttactcttcaaaacaaatcgaaaa
gtaaccgttaagcaattaaaagaagattatttcaaaaaaatagaatgttttgatagtgttgaaatttcaggagttgaagatag
atttaatgcttcattagggacctaccatgatttgctaaaaattattaaagataaagatttttggataatgaagaaaatgaagat
atcttagaggatattgttttaacattgaccttatttgaagatagggagatgattgaggaaagacttaaaacatacgctcacctc
tttgatgataaggtgatgaaacagcttaaacgtcgccgttatactggttggggacgtttgtctcgaaaattgattaatggtatta
gggataagcaatctggcaaaacaatattagattttttgaaatcagatggttttgccaatcgcaattttatgcagctgatccatg
atgatagtttgacatttaaagaagatattcaaaaagcacaagtgtctggacaaggcgatagtttacatgaacatattgcaaa
tttagctggtagccctgctattaaaaaaggtattttacagactgtaaaagttgttgatgaattggtcaaagtaatggggcggca
taagccagaaaatatcgttattgaaatggcacgtgaaaatcagacaactcaaaagggccagaaaaattcgcgagagcg
tatgaaacgaatcgaagaaggtatcaaagaattaggaagtcagattcttaaagagcatcctgttgaaaatactcaattgca
aaatgaaaagctctatctctattatctccaaaatggaagagacatgtatgtggaccaagaattagatattaatcgtttaagtg
attatgatgtcgatgccattgttccacaaagtttccttaaagacgattcaatagacaataaggtcttaacgcgttctgataaaa
atcgtggtaaatcggataacgttccaagtgaagaagtagtcaaaagatgaaaaactattggagacaacttctaaacgc
caagttaatcactcaacgtaagtttgataatttaacgaaagctgaacgtggaggttttgagtgaacttgataaagctggttttat
caaacgccaattggttgaaactcgccaaatcactaagcatgtggcacaaattttggatagtcgcatgaatactaaatacga
tgaaatgataaacttattcgagaggttaaagtgattaccttaaaatctaaattagtttctgacttccgaaaagatttccaattct
ataaagtacgtgagattaacaattaccatcatgcccatgatgcgtatctaaatgccgtcgttggaactgctttgattaagaaat
atccaaaacttgaatcggagtttgtctatggtgattataaagtttatgatgttcgtaaaatgattgctaagtctgagcaagaaat
aggcaaagcaaccgcaaaatatttcttttactctaatatcatgaacttcttcaaaacagaaattacacttgcaaatggagag
attcgcaaacgccctctaatcgaaactaatggggaaactggagaaattgtctgggataaagggcgagattttgccacagt
gcgcaaagtattgtccatgccccaagtcaatattgtcaagaaaacagaagtacagacaggcggattctccaaggagtca

FIG. 8J attttaccaaaaagaaattcggacaagcttattgctcgtaaaaaagactgggatccaaaaaaatatggtggttttgatagtc
caacggtagcttattcagtcctagtggttgctaaggtggaaaaagggaaatcgaagaagttaaaatccgttaaagagttac
tagggatcacaattatggaagaagttcctttgaaaaaaatccgattgacttttagaagctaaaggatataaggaagttaa
aaaagacttaatcattaaactacctaaatatagtcttttgagttagaaaacggtcgtaaacggatgctggctagtccgga
gaattacaaaaaggaaatgagctggctctgccaagcaaatatgtgaatttttatatttagctagtcattatgaaaagttgaag
ggtagtccagaagataacgaacaaaaacaattgtttgtggagcagcataagcattatttagatgagattattgagcaaatc
agtgaattttctaagcgtgttattttagcagatgccaatttagataaagttcttagtgcatataacaaacatagagacaaacca
atacgtgaacaagcagaaaatattattcatttatttacgttgacgaatcttggagctcccgctgcttttaaatatttgatacaac
aattgatcgtaaacgatatacgtctacaaaagaagttttagatgccactcttatccatcaatccatcactggtctttatgaaac
acgcattgatttgagtcagctaggaggtgactaa Exemplary Cas9 Protein: SEQ ID NO: 44:

MDKKYSIGLAIGTNSVGWAVITDEYKVPSKKFKVLGNTDRHSIKKNLIGALLFDSGETAE
ATRLKRTARRRYTRRKNRICYLQEIFSNEMAKVDDSFFHRLEESFLVEEDKKHERHPIF
GNIVDEVAYHEKYPTIYHLRKKLVDSTDKADLRLIYLALAHMIKFRGHFLIEGDLNPDNS
DVDKLFIQLVQTYNQLFEENPINASGVDAKAILSARLSKSRRLENLIAQLPGEKKNGLFG
NLIALSLGLTPNFKSNFDLAEDAKLQLSKDTYDDDLDNLLAQIGDQYADLFLAAKNLSDA
ILLSDILRVNTEITKAPLSASMIKRYDEHHQDLTLLKALVRQQLPEKYKEIFFDQSKNGYA
GYIDGGASQEEFYKFIKPILEKMDGTEELLVKLNREDLLRKQRTFDNGSIPHQIHLGELH
AILRRQEDFYPFLKDNREKIEKILTFRIPYYVGPLARGNSRFAWMTRKSEETITPWNFEE
VVDKGASAQSFIERMTNFDKNLPNEKVLPKHSLLYEYFTVYNELTKVKYVTEGMRKPA
FLSGEQKKAIVDLLFKTNRKVTVKQLKEDYFKKIECFDSVEISGVEDRFNASLGTYHDLL
KIIKDKDFLDNEENEDILEDIVLTLTLFEDREMIEERLKTYAHLFDDKVMKQLKRRRYTG
WGRLSRKLINGIRDKQSGKTILDFLKSDGFANRNFMQLIHDDSLTFKEDIQKAQVSGQG
DSLHEHIANLAGSPAIKKGILQTVKVVDELVKVMGRHKPENIVIEMARENQTTQKGQKN
SRERMKRIEEGIKELGSQILKEHPVENTQLQNEKLYLYYLQNGRDMYVDQELDINRLSD
YDVDAIVPQSFLKDDSIDNKVLTRSDKNRGKSDNVPSEEVVKKMKNYWRQLLNAKLIT
QRKFDNLTKAERGGLSELDKAGFIKRQLVETRQITKHVAQILDSRMNTKYDENDKLIRE
VKVITLKSKLVSDFRKDFQFYKVREINNYHHAHDAYLNAVVGTALIKKYPKLESEFVYGD
YKVYDVRKMIAKSEQEIGKATAKYFFYSNIMNFFKTEITLANGEIRKRPLIETNGETGEIV
WDKGRDFATVRKVLSMPQVNIVKKTEVQTGGFSKESILPKRNSDKLIARKKDWDPKKY
GGFDSPTVAYSVLVVAKVEKGKSKKLKSVKELLGITIMERSSFEKNPIDFLEAKGYKEVK
KDLIIKLPKYSLFELENGRKRMLASAGELQKGNELALPSKYVNFLYLASHYEKLKGSPE
DNEQKQLFVEQHKHYLDEIIEQISEFSKRVILADANLDKVLSAYNKHRDKPIREQAENIIH
LFTLTNLGAPAAFKYFDTTIDRKRYTSTKEVLDATLIHQSITGLYETRIDLSQLGGD

MICROORGANISMS WITH INCREASED PHOTOSYNTHETIC CAPACITY

CROSS REFERENCE TO RELATED APPLICATION

This Application claims priority to U.S. Provisional Patent Application No. 62/152,506 filed Apr. 24, 2015, the entire contents of which are incorporated by reference herein.

FIELD OF THE DISCLOSURE

The disclosure provides microorganisms with increased photosynthetic capacity. Increased photosynthetic capacity is achieved by down-regulating activity of the RpaB pathway. The microorganisms include Cyanobacteria, including genetically-modified Cyanobacteria.

BACKGROUND OF THE DISCLOSURE

Photosynthesis is a process by which solar energy is converted into chemical bond energy. The process of photosynthesis ultimately results in biomass accumulation. Biomass can be used to produce energy, fuel, chemicals, and food. As examples, bioethanol can be produced through alcohol fermentation of saccharified carbohydrate, and biodiesel oil and biojetfuel can be produced from neutral lipids such as waxesters and triglycerides. Further, photosynthesis processes environmental carbon dioxide.

Photosynthetic crops such as soy beans, corn, and palms have been used as raw materials to produce biofuel and other products. Use of edible crops for such purposes, however, can contribute to food shortages. Non-edible crops such as jatropha and camelina have also been used, but these crops have low yields per unit area.

Photosynthetic microorganisms similarly can be cultivated to produce energy, fuel, chemicals, and food, as well as to process environmental carbon dioxide. In fact, many of these photosynthetic microorganisms are capable of producing larger amount of oils, fats and carbohydrates than plants.

SUMMARY OF THE DISCLOSURE

The present disclosure provides modified photosynthetic microorganisms with increased photosynthetic capacity. Increased photosynthetic capacity is achieved by down-regulating activity of the RpaB pathway. Increased photosynthetic capacity can increase total carbon fixation, production of carbon containing compounds, and growth (biomass accumulation), among other uses.

BRIEF DESCRIPTION OF THE FIGURES

FIGS. 5 and 6 show that photoautotrophic growth of photosynthetic microorganism with down-regulated RpaB pathway activity is increased by repeatedly replacing a volume fraction of the liquid culture with an equivalent volume of new growth media.

FIG. 7 provides a scheme depicting multiple routes through which RpaB may affect expression of light responsive genes. Overexpression of full-length RpaB may increase the amount of full length, phosphorylated RpaB, which acts as an activator for some genes and a repressor for others. Dephosphorylated RpaB may as act as an activator or repressor for other sets of genes.

FIG. 8A-J provides exemplary sequences referenced throughout the disclosure.

DETAILED DESCRIPTION

Figure 1:
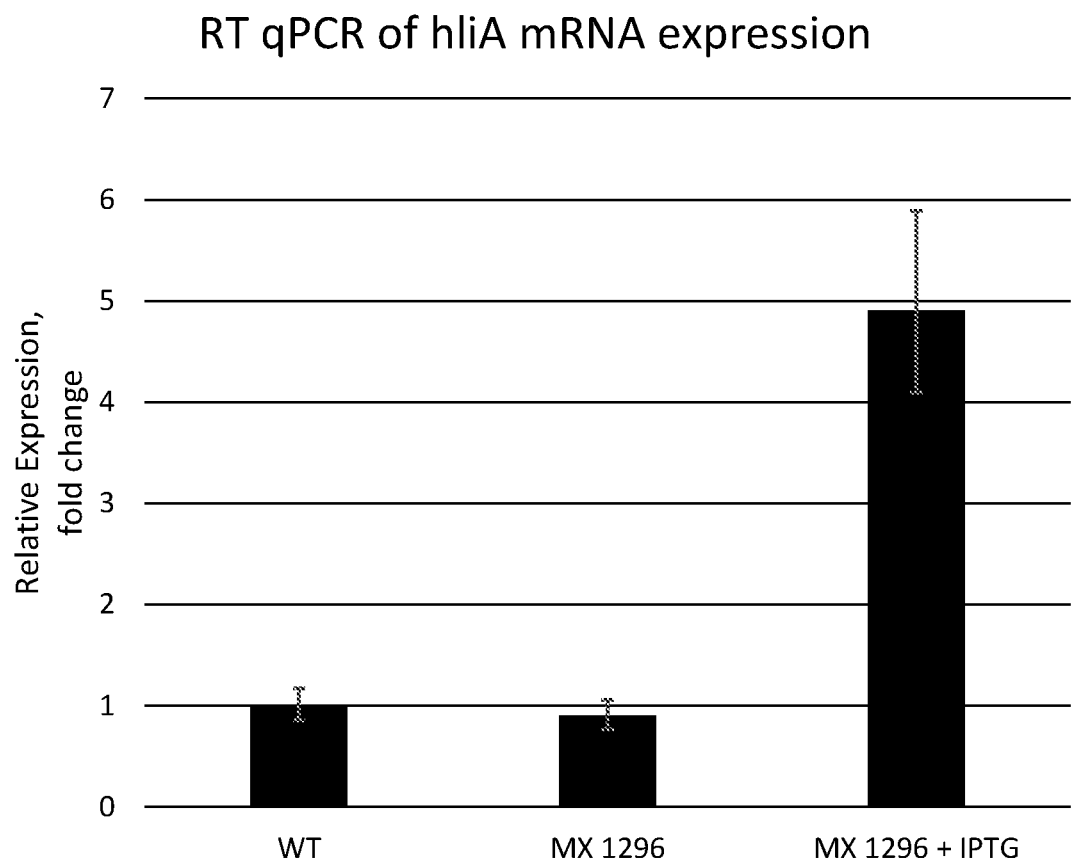
FIG. 1 depicts relative mRNA expression levels of hliA in wild type (e.g., non-modified) and mutant strain MX1296 (Ptrc:N-rpaB) without and with addition of 1 mM IPTG.

Photosynthesis is a process by which solar energy is converted into chemical bond energy. The overall reaction of photosynthesis is the light-driven conversion of carbon dioxide and water to glucose and oxygen:

$$6CO_2 + 6H_2O \rightarrow C_6H_{12}O_6 + 6O_2$$

Photosynthesis is observed in plants as well as in bacteria, and blue-green algae.

The process of photosynthesis ultimately results in biomass accumulation. Biomass can be used to produce energy, fuel, chemicals, and food. As examples, bioethanol can be produced through alcohol fermentation of saccharified carbohydrate, and biodiesel oil and biojetfuel can be produced from neutral lipids such as waxesters and triglycerides. Further, photosynthesis processes environmental carbon dioxide.

Photosynthesis includes two stages called the light reactions and the dark reactions. The light reactions require the presence of light, while the dark reactions do not depend on direct light exposure. In the light reactions, sunlight is absorbed and drives an electron transport chain that results in the formation of the energy carriers NADPH and ATP, forming $O_2$ as a by-product. In the dark reactions, a reaction driven by NADPH and ATP reduces $CO_2$ to glucose.

Photosystems are large multiprotein complexes that allow, in collaboration with other components, the conversion of captured solar energy into chemical bond energy via the electron transport chain. In general, photosystems are made up of two components: (1) a photochemical reaction center that allows solar energy to be converted into chemical energy, and (2) an antenna complex which captures light energy and transfers it to the photochemical reaction center, resulting in excitation of the photosystem.

The source of electron replenishment in a photosynthesis system differs according to the reaction center type. In purple non-sulfur bacteria, for example, electrons are cycled back to the reaction center by water-soluble electron carriers, for example, a cytochrome c type protein. In oxygenic photosynthetic organisms, including Cyanobacteria, red and green algae and plants, electron flow is non-cyclic, and occurs in two steps that involve two photosystems: Photosystem I (PSI) and Photosystem II (PSII). In these types of reactions, the deficit of electrons can be replenished by electrons taken from water molecules.

PSII is a complex composed of proteins, pigments and cofactors, located within thylakoid membranes. PSII splits water into oxygen, protons and electrons. Oxygen is released into the atmosphere and is responsible for maintaining aerobic life on Earth. The electrons are immediately energized by a photon ($\lambda$=680 nm) in PSII and passed from one compound to another, all of which compose the electron transport chain. Most of the electron carriers are quinones (Q), plastiquinones (PQ), or cytochromes (Cyt).

More particularly, the process of electron transfer in PSII includes the following steps: upon illumination, a $P_{680}$ chlorophyll is photoexcited. The photoexcited $P_{680}$ transfers electrons via intermediate cofactors called pheophytin a and plastoquinone A (PQ, $Q_A$) in order to finally doubly reduce a transiently bound PQ molecule ($Q_B$). $Q_B^{2-}$ is protonated and released from the reaction center into the thylakoid membrane. The redox active cofactors that enable electron transfer from water to the secondary quinone acceptor $Q_B$ are mainly embedded within two proteins called D1 and D2. Under normal conditions of illumination, the D1 protein of the reaction center core is irreversibly damaged over time and is replaced in a fashion that preserves the integrity of the PSII complex.

A second input of light energy ($\lambda$=700 nm) occurs during PSI and the energized electrons are passed to the terminal electron carrier, ferredoxin (Fd). Reduced Fd can serve as an electron donor to the ferredoxin-NADP$^+$-reductase (FNR) enzyme. In a parallel process (photophosphorylation), H$^+$ are released where they generate a H$^+$ gradient that is used to drive ATP production via ATP synthase. NADPH and ATP are subsequently used to produce starch and other forms of energy storage biomass.

Cyanobacteria are the only group of organisms that are able to reduce nitrogen and carbon in aerobic conditions. The water-oxidizing photosynthesis is accomplished by coupling the activity of PSII and PSI (the Z-scheme). In anaerobic conditions, Cyanobacteria are also able to use only PSI (i.e., cyclic photophosphorylation) with electron donors other than water (e.g., hydrogen sulfide, thiosulphate, or molecular hydrogen), similar to purple photosynthetic bacteria. Furthermore, Cyanobacteria share an archaeal property—the ability to reduce elemental sulfur by anaerobic respiration in the dark. The Cyanobacterial photosynthetic electron transport system shares the same compartment as the components of respiratory electron transport. Typically, the plasma membrane contains only components of the respiratory chain, while the thylakoid membrane hosts both respiratory and photosynthetic electron transport.

Phycobilisomes are complexes of phycobiliproteins and colorless polypeptides which function as the major light harvesting antennae in blue-green and red algae. The phycobilisome components (phycobiliproteins) are responsible for the blue-green pigmentation of most Cyanobacteria. Color variations are mainly due to carotenoids and phycoerythrins, which may provide the cells with a red-brownish coloration. In some Cyanobacteria, the color of light influences the composition of phycobilisomes. In green light, the cells accumulate more phycoerythrin, whereas in red light they produce more phycocyanin. Thus, the bacteria appear green in red light and red in green light. This process is known as complementary chromatic adaptation and represents a way for the cells to maximize the use of available light for photosynthesis.

As suggested, photosynthetic organisms must cope with environmental changes in their habitats, such as fluctuations in incident light. Changes in light quantity or quality (i.e., spectral composition) can result in imbalanced excitation of PSII and PSI and decrease the efficiency of photosynthetic light reactions. Photosynthetic organisms can counteract such excitation imbalances with changes in gene expression.

OmpR response regulators are response regulators wherein their phosphorylation promotes specific DNA binding by enhancing dimer or oligomer formation. In some cases, dephosphorylated OmpR response regulators have >10-fold lower affinity to their binding sites than phosphorylated forms. RpaA and RpaB are two types of OmpR response regulators.

The NbIS kinase (NbIS)-RpaB signaling pathway is the most conserved two-component system in Cyanobacteria. This pathway is involved in regulation of circadian-based changes in gene expression, regulation of photosynthesis, and acclimatization to a variety of environmental conditions.

The full length protein RpaB has an N-terminal phosphoreciever domain and a C-terminal DNA binding domain. The C-terminal domain is responsible for binding promoter regions such as HLR1 (high light-responsive element 1) and repressing transcription of downstream genes when RpaB is phosphorylated (at the N-terminal side of the protein). N-terminal fragments of the RpaB protein can have a phospho-receiver domain but no known DNA binding domain. The phosphorylatable residue of RpaB is thought to be Asp56.

With regard to regulation of circadian-based changes in gene expression, RpaB binds the KaiBC promoter and represses transcription of kaiBC and other target genes during subjective night (e.g., ~LL0). During subjective day (e.g., ~LL4-8), RpaB is released from these promoters, likely through the effects of RpaA, to allow transcription of the repressed genes.

As stated, with regard to regulation of photosynthesis, RpaB binds to the promoter HLR1. The HLR1 motif includes two direct repeats of SEQ ID NO: 1 separated by two nucleotides. When bound to HLR1, RpaB represses transcription of genes, such as rpoD3 and hliA. Under high light stress, RpaB is dephosphorylated in a process mediated by NbIS to allow translation of these genes.

Decreasing the copy number of RpaB genes in Cyanobacteria decreases energy transfer from phycobilisomes to PSII and increases energy transfer from phycobilisomes to PSI. Thus, it is been suggested that RpaA and RpaB regulate expression of proteins involved in the coupling of phycobilisomes to PSI or PSII. With regard to acclimation to other environmental conditions, RpaB has been shown to modulate transcription of genes in response to cold shock as well as osmotic, salt and oxidative stresses. In spite of the importance of the NblS-RpaB signaling pathway, actual input signals and output responses remain largely unknown.

SrrA is homologous to RpaB, but has distinctly different regulatory roles in *Synechococcus elongatus* PCC 7942 and is coded by a non-essential gene. SrrA is also known as Crr71. RpaB and SrrA are the only known substrates of the NblS kinase.

The current disclosure provides microorganisms with increased photosynthetic capacity. Increased photosynthetic capacity can be achieved by down-regulating activity of the RpaB pathway. Numerous mechanisms to down-regulate activity of the RpaB pathway are described herein. Particular examples include expression of RpaB decoys, expression of SrrA decoys and/or direct down-regulation of NblS, through, for example, CRISPRi.

Aspects of the current disclosure are now described in more detail.

Photosynthetic Microorganisms. Photosynthetic microorganisms of the disclosure may be any type of organism capable of performing photosynthesis wherein the microorganism has been modified to have down-regulated RpaB pathway activity.

Exemplary photosynthetic microorganisms that are either naturally photosynthetic or can be engineered to be photosynthetic include bacteria (e.g., Cyanobacteria); fungi; archaea; protists; eukaryotes, such as a green algae; and animals such as plankton, planarian, and amoeba. Examples of naturally occurring photosynthetic microorganisms include *Arthrospira* (*Spirulina*) *maxima*, *Arthrospira* (*Spirulina*) *platensis*, *Dunaliella salina*, *Botrycoccus braunii*, *Chlorella vulgaris*, *Chlorella pyrenoidosa*, *Serenastrum capricornutum*, *Scenedesmus auadricauda*, *Porphyridium cruentum*, *Scenedesmus acutus*, *Dunaliella* sp., *Scenedesmus obliquus*, *Anabaenopsis*, *Aulosira*, *Cylindrospermum*, *Synechoccus* sp., *Synechocystis* sp., *Cyanobacterium aponinum*, and *Tolypothrix* sp.

Cyanobacteria, also known as blue-green algae, blue-green bacteria, or Cyanophyta, is a phylum of bacteria that obtain their energy through photosynthesis. As stated, Cyanobacteria can produce metabolites, such as carbohydrates, proteins, lipids and nucleic acids, from $CO_2$, water, inorganic salts and light. Any Cyanobacteria may be used according to the disclosure. In particular embodiments the Cyanobacteria must be genetically manipulatable, e.g., permissible to the introduction and expression of exogenous genetic material (e.g., exogenous nucleotide sequences).

Cyanobacteria include both unicellular and colonial species. Colonies may form filaments, sheets or even hollow balls. Some filamentous colonies show the ability to differentiate into several different cell types, such as vegetative cells, the normal, photosynthetic cells that are formed under favorable growing conditions; akinetes, the climate-resistant spores that may form when environmental conditions become harsh; and thick-walled heterocysts, which contain the enzyme nitrogenase, vital for nitrogen fixation.

Examples of Cyanobacteria that may be utilized and/or genetically modified according to the methods described herein include *Chroocccales* Cyanobacteria from the genera *Arthrospira*, *Aphanocapsa*, *Aphanothece*, *Chamaesiphon*, *Chroococcus*, *Chroogloeocystis*, *Coelosphaerium*, *Crocosphaera*, *Cyanobacterium*, *Cyanobium*, *Cyanodictyon*, *Cyanosarcina*, *Cyanothece*, *Dactylococcopsis*, *Gloecapsa*, *Gloeothece*, *Merismopedia*, *Microcystis*, *Radiocystis*, *Rhabdoderma*, *Snowella*, *Synychococcus*, *Synechocystis*, *Thermosenechococcus*, and *Woronichinia*; *Nostacales* Cyanobacteria from the genera *Anabaena*, *Anabaenopsis*, *Aphanizomenon*, *Aulosira*, *Calothrix*, *Coleodesmium*, *Cyanospira*, *Cylindrospermosis*, *Cylindrospermum*, *Fremyella*, *Gleotrichia*, *Microchaete*, *Nodularia*, *Nostoc*, *Rexia*, *Richelia*, *Scytonema*, *Sprirestis*, and *Toypothrix*; *Oscillatoriales* Cyanobacteria from the genera *Arthrospira*, *Geitlerinema*, *Halomicronema*, *Halospirulina*, *Katagnymene*, *Leptolyngbya*, *Limnothrix*, *Lyngbya*, *Microcoleus*, *Oscillatoria*, *Phormidium*, *Planktothricoides*, *Planktothrix*, *Plectonema*, *Pseudoanabaena/Limnothrix*, *Schizothrix*, *Symploca*, *Trichodesmium*, and *Tychonema*; *Pleurocapsales* Cyanobacteria from the genera *Chroococcidiopsis*, *Dermocarpa*, *Dermocarpella*, *Myxosarcina*, *Pleurocapsa*, *Stanieria*, and *Xenococcus*; *Prochlorophytes* Cyanobacteria from the genera *Prochloron*, *Prochlorococcus*, and *Prochlorothrix*; and *Stigonematales* Cyanobacteria from the genera *Capsosira*, *Chlorogeoepsis*, *Fischerella*, *Hapalosiphon*, *Mastigocladopsis*, *Nostochopsis*, *Stigonema*, *Symphyonema*, *Symphonemopsis*, *Umezakia*, and *Westiellopsis*. In particular embodiments, the Cyanobacteria is from the genus *Synechococcus*, including *Synechococcus bigranulatus*, *Synechococcus elongatus*, *Synechococcus leopoliensis*, *Synechococcus lividus*, *Synechococcus nidulans*, and *Synechococcus rubescens*. Cyanobacteria *Thermosynechococcus*, and *Gloeobacter* can also be used.

More particular embodiments include or utilize *Anabaena* sp. strain PCC 7120, *Synechocystis* sp. strain PCC 6803, *Nostoc muscorum*, *Nostoc ellipsosporum*, or *Nostoc* sp. strain PCC 7120. In particular embodiments, the Cyanobacteria is *Synechococcus elongatus* sp. strain PCC 7942. Additional examples of Cyanobacteria that may utilized include *Synechococcus* sp. strains WH7803, WH8102, WH8103 (typically genetically modified by conjugation), Baeocyte-forming *Chroococcidiopsis* spp. (typically modified by conjugation/electroporation), non-heterocyst-forming filamentous strains *Planktothrix* sp., *Plectonema boryanum* M101 (typically modified by electroporation), Heterocyst-forming *Anabaena* sp. ATCC 29413 (typically modified by conjugation), *Tolypothrix* sp. strain PCC 7601 (typically modified by conjugation/electroporation) and *Nostoc punctiforme* strain ATCC 29133 (typically modified by conjugation/electroporation).

In particular embodiments, the Cyanobacteria may be, e.g., a marine form of Cyanobacteria or a fresh water form of Cyanobacteria. Examples of marine forms of Cyanobacteria include *Synechococcus* WH8102, *Synechococcus* RCC307, *Synechococcus* NKBG 15041c, and *Trichodesmium*. Examples of fresh water forms of Cyanobacteria include *S. elongatus* PCC 7942, *Synechocystis* PCC6803, *Plectonema boryanum*, *Cyanobacterium aponinum*, and *Anabaena* sp.

In other embodiments, a genetically modified Cyanobacteria may be capable of growing in brackish or salt water. When using a fresh water form of Cyanobacteria, the overall net cost of their use will depend on both the nutrients required to grow the culture and the price for freshwater. One can foresee freshwater being a limited resource in the future, and in that case it would be more cost effective to find an alternative to freshwater. Two such alternatives include: (1) the use of waste water from treatment plants; and (2) the use of salt or brackish water.

Salt water in the oceans can range in salinity between 3.1% and 3.8%, the average being 3.5%, and this is mostly, but not entirely, made up of sodium chloride (NaCl) ions.

Brackish water, on the other hand, has more salinity than freshwater, but not as much as seawater. Brackish water contains between 0.5% and 3% salinity, and thus includes a large range of salinity regimes and is therefore not precisely defined. Waste water is any water that has undergone human influence. It includes liquid waste released from domestic and commercial properties, industry, and/or agriculture and can encompass a wide range of possible contaminants at varying concentrations.

There is a broad distribution of Cyanobacteria in the oceans, with Synechococcus filling just one niche. Specifically, Synechococcus sp. PCC 7002 (formerly known as Agmenellum quadruplicatum strain PR-6) grows in brackish water, is unicellular and has an optimal growing temperature of 38° C. While this strain is well suited to grow in conditions of high salt, it will grow slowly in freshwater. In particular embodiments, the disclosure includes the use of a Cyanobacteria PCC 7942, altered in a way that allows for growth in either waste water or salt/brackish water. A Synechococcus elongatus PCC 7942 mutant resistant to sodium chloride stress has been described (Bagchi et al., Photosynth Res., 2007; 92:87-101), and a genetically modified S. elongatus PCC 7942 tolerant of growth in salt water has been described (Waditee et al., PNAS, 2002; 99:4109-4114). Salt water tolerant Cyanobacteria may also be prepared as described in the Examples of U.S. Pat. No. 8,394,614. According to the disclosure a salt water tolerant strain is capable of growing in water or media having a salinity in the range of 0.5% to 4.0% salinity, although it is not necessarily capable of growing in all salinities encompassed by this range. In particular embodiments, a salt tolerant strain is capable of growth in water or media having a salinity in the range of 1.0% to 2.0% salinity. In particular embodiments, a salt water tolerant strain is capable of growth in water or media having a salinity in the range of 2.0% to 3.0% salinity.

Down-regulating activity of the RpaB pathway can be achieved through various mechanisms. Down-regulation of the RpaB pathway can be achieved by, for example, decreasing the presence or activity of a protein or gene in the pathway that promotes pathway activation (e.g., full length RpaB, SrrA or NbIS). Down-regulation of the RpaB pathway can also be achieved by, for example, increasing the presence or activity of a protein or gene in the pathway that inhibits pathway activation (e.g., a pathway phosphatase or a pathway decoy that dampens effective activity of other active pathway members (e.g., a wild-type RpaB or SrrA sequence with the phospho-receiver domain substituted with amino acids that are not phosphorylatable (a non-conservative substitution) or inhibitory CRISPRi expression products).

A decrease in presence or activity of a protein or gene in a pathway can be caused by, for example, reduction of a gene's copy number, insertion of a foreign set of base pairs into a gene (e.g., into a coding region), deletion of any portion of the gene (e.g., of all or part of a coding region), substitution of base pairs within the gene (e.g., into a coding region), interference with an encoded RNA transcript, the presence of antisense sequences that interfere with transcription or translation of the gene; translation of an incomplete protein; incorrect folding of a protein; expression of an unstable protein; reduced transcription of a gene; incomplete transcription of a gene, or by any other activity resulting in reduced presence, expression or activity of a protein in the pathway that promotes pathway activation.

An increase in presence or activity of a protein or gene in a pathway can be caused by, for example, an increase in a gene's copy number, introduction of a strong and/or inducible promoter, mechanisms to prevent degradation of encoding nucleotides or expressed proteins, or other mechanisms.

In particular embodiments, the RpaB pathway is down-regulated by expressing an RpaB decoy and/or an SrrA decoy. Without being bound by theory, expressed decoys will compete with full length wild type RpaB and/or Srra for phosphorylation (e.g., on Asp56 or Asp64, respectively). This competition will result in a net decrease in the phosphorylation of wild type RpaB proteins, and thus up-regulation of RpaB-regulated gene expression. This approach can be referred to as a "dominant interfering" phenotype as the modified photosynthetic microorganism is expected to have a lower degree of transcriptional repression at HLR1. In other words, a constitutive "high light" (or deprivation of certain nutrient) phenotype can be created. Thus, in particular embodiments, down-regulation of the RpaB pathway can be evidenced by the up-regulation of an RpaB-regulated gene, such as hliA (see FIG. 1) and RpoD3.

In particular embodiments, the RpaB and/or SrrA decoy is a protein that will compete with wild-type RpaB for phosphorylation. The term "wild-type" can be used interchangeably with "naturally occurring" and refers to a gene or gene product (e.g., transcript or protein) that has the characteristics of that gene or gene product when isolated from a naturally occurring source. A wild type gene or gene product is that which is most frequently observed in a population and is thus arbitrarily designated the "normal" or "wild-type" form of the gene or gene product.

In particular embodiments, the RpaB decoy is a protein that can be phosphorylated by one or more kinases capable of phosphorylating wild-type RpaB. In particular embodiments, the RpaB decoy is a protein that can be phosphorylated by NbIS. In particular embodiments, the RpaB decoy includes a wild-type RpaB phospho-receiver domain. In particular embodiments, the RpaB decoy includes a wild-type RpaB phospho-receiver domain and 1, 2, 3, 4, or 5 wild-type amino acid residues flanking this position. In these embodiments, the phospho-receiver domain includes Asp56. In particular embodiments, the RpaB decoy includes a wild-type RpaB phospho-receiver domain and does not include a wild-type DNA binding domain or includes a non-functional DNA binding domain. In particular embodiments, the RpaB decoy includes an N-terminal fragment of the wild-type RpaB, including the wild-type phospho-receiver domain but does not include a DNA binding domain or includes a non-functional DNA binding domain. In particular embodiments, the wild-type phospho-receiver domain includes Asp56. As indicated below, this Asp can be replaced with phospho-receiver domain conservative substitutions such as Glu, Ser and Thr. In particular embodiments, the RpaB decoy can be N-RpaB (SEQ ID NO: 2).

In particular embodiments, a gene from Synechococcus elongatus PCC 7942 that encodes a RpaB decoy can be placed behind an inducible promoter in a neutral site (e.g., NS1) to drive expression of the RpaB decoy. In particular embodiments, the gene can contain the first 378 base pairs of the gene Synpcc7942_1453 (full length gene is 735 base pairs), followed by a stop codon, and can be placed behind an IPTG inducible promoter in a neutral site (e.g., NS1 or NS2) to drive expression of N-RpaB (SEQ ID NO: 2). This gene and associated nucleotide sequence is represented by SEQ ID NO: 23. In this sequence, the wild type start codon has been modified from TTG to ATG.

Overexpression of the N-RpaB protein fragment conferred a transcriptional response similar to one observed when cells are stressed with, e.g. high light or deprivation of certain nutrients. For example, the mRNA expression level of the gene hliA, which is known to increase under high light, increases 5-fold relative to wild type or uninduced mutant levels, as shown in FIG. 1.

Figure 2:
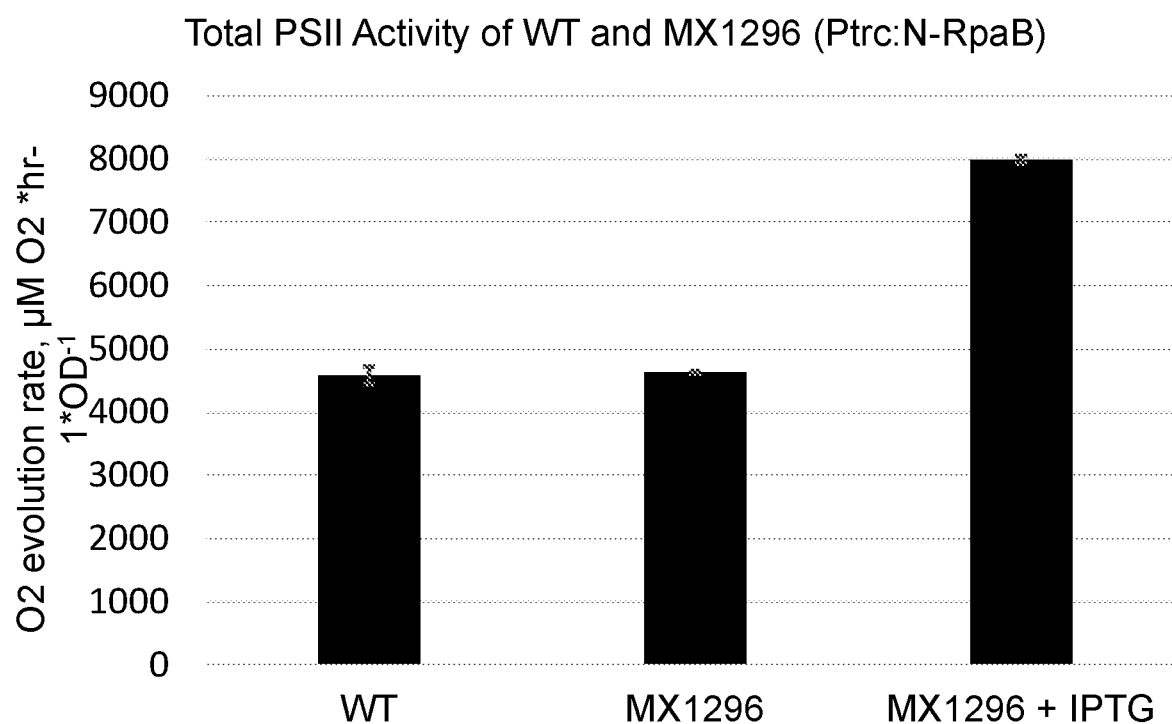
FIG. 2 depicts total photosystem II (PSII) activity of wild type and strain MX1296 grown without or with 1 mM IPTG in medium. Activity was measured by determining the rate of oxygen evolution of whole cells in the presence of para-benzoquinone and potassium ferricyanide, which serve to accept electrons directly from PSII, allowing for PSII oxygen evolution to run at maximal rate, independent of down-stream proteins in the electron transport chain.

When the strain with this mutation is grown in the presence of 1 mM IPTG, it has a higher photosystem II activity and higher photosynthetic electron transport capacity than wild type. Photosystem II activity is measured by determining the rate of oxygen evolution of whole cells in the presence of para-benzoquinone and potassium ferricyanide, which serve to accept electrons directly from PSII, allowing for PSII oxygen evolution to run at its maximal rate, independent of down-stream proteins in the electron transport chain. FIG. 2 shows the maximal oxygen evolution capacity of PSII in cells with induction of the RpaB protein fragment (denoted N-RpaB) with 1 mM IPTG.

Figure 3:
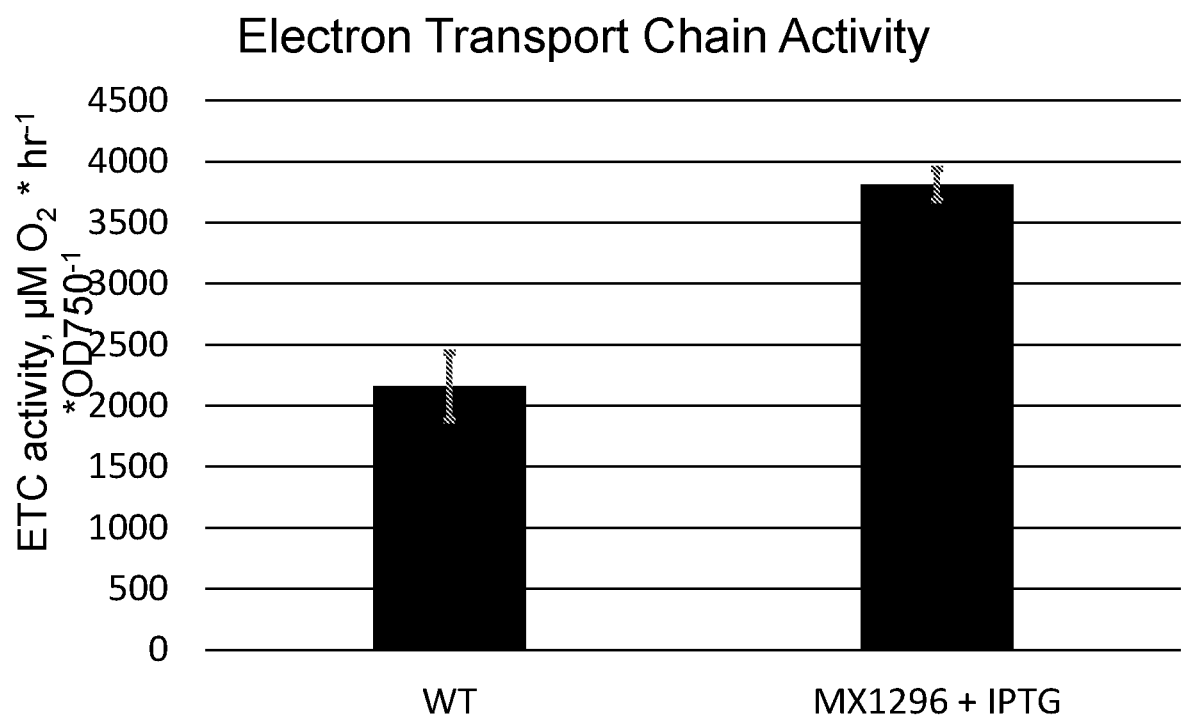
FIG. 3 depicts total electron transport chain activity of wild type and strain MX1296 grown with 1 mM IPTG in medium. Activity was measured by determining the rate of oxygen uptake of whole cells in the presence of methyl viologen and potassium cyanide, which serve to accept electrons directly from photosystem I (PSI), allowing for the entire electron transport chain to run at maximal rate, independent of down-stream proteins in, e.g., carbon fixation or nitrate reduction.

Electron transport activity is measured by determining the rate of oxygen consumption of whole cells under bright light illumination in the presence of methyl viologen and potassium cyanide. The magnitude of the measured rate of oxygen uptake is equal to the total capacity of the cell's oxygen evolution rate when electrons are passed through its entire electron transport chain via photosynthesis. This increased photosynthetic capacity can increase total carbon fixation, production of carbon containing compounds, and growth (biomass accumulation). Overexpression of the same 378 base pair gene fragment under other strong promoters confers such an increase in electron transport activity. More particularly, FIG. 3 shows the maximal electron transport chain activity of cells with and without induced production of N-RpaB. Without being bound by theory, the increase in PSII capacity allows for increased total electron transport chain activity in *Synechococcus*.

SEQ ID NO: 24 provides a reference wild-type RpaB protein sequence and SEQ ID NO: 25 provides a reference wild-type RpaB gene sequence. These reference sequences are derived from Synpcc7942_1453. SEQ ID NO: 29 provides a reference wild-type RpaB protein sequence and SEQ ID NO: 30 provides a reference wild-type RpaB gene sequence derived from *Arthrospira platensis* (NIES39_K03840). SEQ ID NO: 31 provides a reference wild-type RpaB protein sequence and SEQ ID NO: 32 provides a reference wild-type RpaB gene sequence derived from *Cyanobacterium aponinum* (WP_015219361.1). Additional homologous protein and gene sequences can also serve as reference wild-type RpaB protein sequences for the purposes of this disclosure. Exemplary homologous reference RpaB protein sequences include SEQ ID NOs: 26, 27 and 28 derived from *Synechococcus* sp. (WH 8102), *Tolypothrix* sp. (PCC 7601), and *Thermosynechococcus* sp. (NK55a) respectively.

In particular embodiments, the SrrA decoy is a protein that can be phosphorylated by one or more kinases capable of phosphorylating wild-type SrrA. In particular embodiments, the SrrA decoy is a protein that can be phosphorylated by NbIS. In particular embodiments, the SrrA decoy includes a wild-type SrrA phospho-receiver domain. In particular embodiments, the SrrA decoy includes a wild-type SrrA phospho-receiver domain and 1, 2, 3, 4, or 5 wild-type amino acid residues flanking this position. In these embodiments, the phospho-receiver domain includes Asp64. In particular embodiments, the SrrA decoy includes a wild-type SrrA phospho-receiver domain and does not include a wild-type DNA binding domain or includes a non-functional DNA binding domain. In particular embodiments, the SrrA decoy includes an N-terminal fragment of the wild-type RpaB, including the wild-type phospho-receiver domain but does not include a DNA binding domain or includes a non-functional DNA binding domain. In particular embodiments, the wild-type phospho-receiver domain includes Asp64. As indicated below, this Asp can be replaced with phospho-receiver domain conservative substitutions such as Glu, Ser and Thr. In particular embodiments, the SrrA decoy can include SEQ ID NO: 34. Non-functional DNA binding domains fail to bind DNA or bind DNA, but result in a significantly reduced amount of resulting gene expression as compared to a relevant control.

Figure 4:
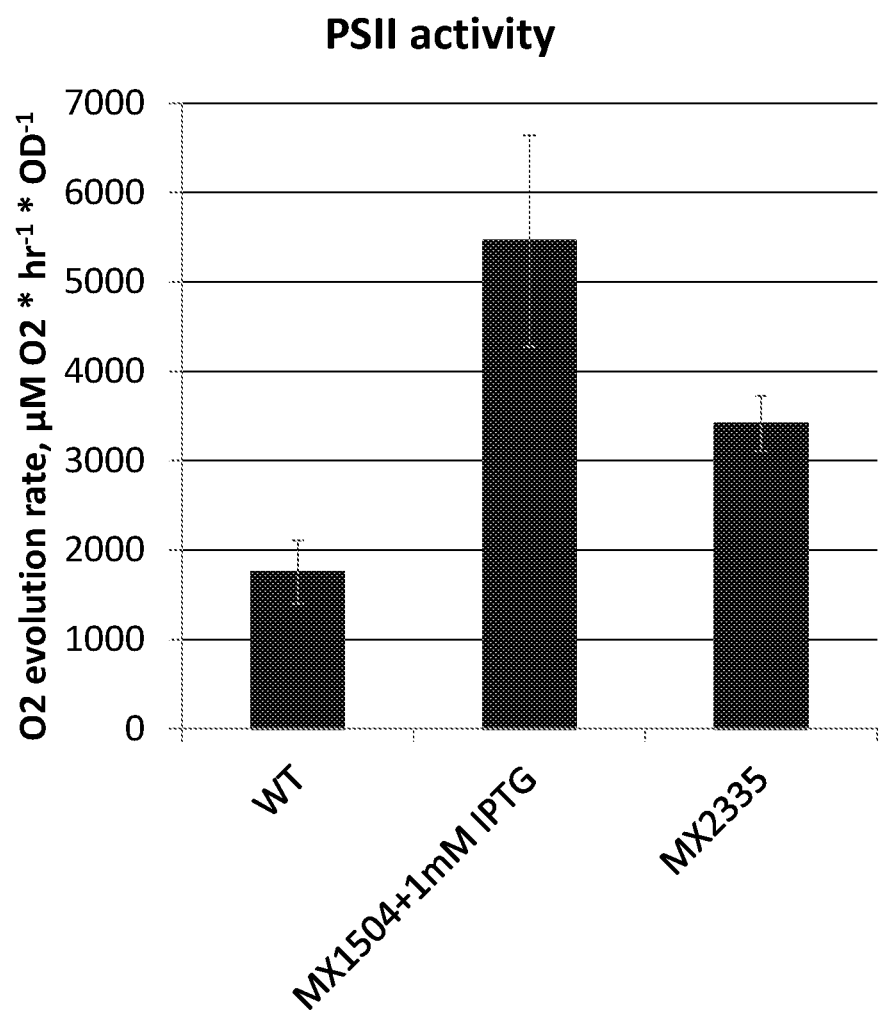
FIG. 4 depicts total photosystem II (PSII) activity of wild type, strain MX1504 (N-RpaB) with 1 mM IPTG in medium, and strain MX2335 (N-SrrA, without added IPTG). Activity was measured by determining the rate of oxygen evolution of whole cells in the presence of para-benzoquinone and potassium ferricyanide, as described in relation to FIG. 2. MX1504 is an N-RpaB strain built in a different WT background than MX1296. The appropriate WT control for MX1296 is named TGA1-75 where the appropriate WT control for MX1504 is named TGA1-30. This FIG. indicates Ptrc_N-SrrA is effective without induction with IPTG, whereas Ptrc_N-RpaB is more effective with IPTG.

In particular embodiments, a gene from *Synechococcus elongatus* PCC 7942 that encodes a SrrA decoy can be placed behind a promoter in a neutral site (e.g., NS1 or NS2) to drive expression of the SrrA decoy. MX2335, Ptrc_N-SrrA, is a strain expressing the first 404 base pairs of gene Synpcc7942_2416 (SEQ ID NO; 33; full length gene is 768 base pairs (SEQ ID NO: 35)), followed by a stop codon, placed behind a constitutive promoter in neutral site 2 (NS2) to drive expression of N-SrrA (SEQ ID NO: 34). In these embodiments, Ptrc is referred to as a constitutive promoter because no addition of IPTG is necessary for low-level induction of expression, and low-level expression of N-SrrA is sufficient to produce the decoy phenotype with increased photosynthetic capacity (FIG. 4). The full length *Synechococcus elongatus* PCC 7942 SrrA is provided as SEQ ID NO: 36.

SEQ ID NO: 38 provides a reference wild-type SrrA protein sequence and SEQ ID NO: 37 provides a reference wild-type SrrA gene sequence derived from *Arthrospira platensis* NIES-39. Additional homologous protein and gene sequences can also serve as reference wild-type SrrA sequences for the purposes of this disclosure. An additional exemplary homologous reference SrrA protein sequences includes SEQ ID NO: 40 and an additional exemplary homologous reference SrrA gene sequence includes SEQ ID NO: 39 derived from *Procholorcoccus marinus* SS120.

Based on the teachings of this disclosure, one of ordinary skill in the art can determine additional homologous sequences, relevant phospho-receiver domains, DNA binding domains, and encoding nucleotide sequences to generate functioning decoys to down-regulate RpaB pathway activity in photosynthetic microorganisms.

The RpaB pathway can also be down-regulated by directly down-regulating NbIS. As indicated previously, there are numerous ways to achieve down-regulation of a protein. In particular embodiments, NbIS can be down-regulated utilizing CRISPRi technology. For example, the minimal CRISPR system from *Streptococcus pyogenes* needed for building an NbIS CRISPRi strain requires only a single gene encoding a Cas9 protein and two RNAs, a mature CRISPR RNA (crRNA) and a partially complementary trans-acting RNA (tracrRNA), to target and cleave foreign DNA elements in a sequence-specific manner. In particular embodiments, the Cas9 protein can be modified by two point mutations (D10A and H841A) at the active sites to obtain the dCas9 protein that can bind to DNA (guided by a complementary RNA sequence) without cleaving it, potentially interfering with transcriptional initiation or elongation (Jinek et al., 2012, A programmable dual-RNA-guided DNA endonuclease in adaptive bacterial immunity. *Science* (New York, N.Y.), 337(6096), 816-21. doi:10.1126/science.1225829). Another modification can include replacement of the two original RNAs in the native system (crRNA and tracrRNA) with an engineered small guide RNA (sgRNA) (Jinek et al., 2012; Mali et al., 2013, RNA-guided human genome engineering via Cas9. *Science*, 823. doi:10.1126/science.1232033).

In particular embodiments, guide RNA designed and used for transcriptional interference of the NbIS gene in *Synechococcus elongatus* PCC7942 can be encoded by the sequence: ttggcaacaactgcgcgata (SEQ ID NO: 41) resulting in the sequence uuggcaacaacugcgcgaua (SEQ ID NO: 42). This sequence can be expressed/placed behind a promoter such as a pTac promoter, which is inducible by addition of 1 mM IPTG to the growth medium. An exemplary DNA sequence to drive expression of the Cas9 protein is provided as SEQ ID NO: 43 which encodes SEQ ID NO: 44. In particular embodiments, its expression can be driven by a promoter such as the pBAD promoter, which is inducible by addition of 0.02% arabinose to the growth medium.

Embodiments disclosed herein do not utilize RpaB knockouts, as complete RpaB knockout is lethal. Accordingly, embodiments disclosed herein utilize down-regulation, rather than elimination, of RpaB pathway activity.

As is understood by one of ordinary skill in the art, "up-regulation" and "down-regulation" of gene and protein expression as well as RpaB pathway activity can be measured against a relevant control condition including relative to the expression or activity of an unmodified photosynthetic microorganism or a photosynthetic microorganism having a different modification (such as a modification un-related to decreasing activity of the RpaB pathway).

In particular embodiments, conclusions are drawn based on whether a measure is statistically significantly different or not statistically significantly different from a reference level of a relevant control. A measure is not statistically significantly different if the difference is within a level that would be expected to occur based on chance alone. In contrast, a statistically significant difference or increase is one that is greater than what would be expected to occur by chance alone. Statistical significance or lack thereof can be determined by any of various systems and methods used in the art. An example of a commonly used measure of statistical significance is the p-value. The p-value represents the probability of obtaining a given result equivalent to a particular datapoint, where the datapoint is the result of random chance alone. A result is often considered significant (not random chance) at a p-value less than or equal to 0.05.

As indicated, various mechanisms to down-regulate the RpaB pathway rely on inserting exogenous nucleotide sequences into the genome of the selected photosynthetic microorganism. "Exogenous" refers to a nucleotide sequence that does not naturally occur in the particular position of the genome of the wild type photosynthetic microorganism where it is inserted, but is inserted at the particular position by molecular biological techniques. Examples of exogenous nucleotide sequences include vectors, plasmids, and/or man-made nucleic acid constructs.

As used herein, nucleotide sequences can include foreign sets of base pairs and genes encoding proteins or RNA (e.g., RpaB decoys, N-RpaB, SrrA decoys, N-SrrA, guide RNA, Cas9 or variants thereof, etc.). In relation to genes, this term includes various sequence polymorphisms, mutations, and/or sequence variants. In particular embodiments, the sequence polymorphisms, mutations, and/or sequence variants do not affect the function of the encoded protein or RNA. Genes may include not only coding sequences but also non-coding regulatory regions such as promoters, enhancers, and termination regions. The term further can include all introns and other DNA sequences spliced from the mRNA transcript, along with variants resulting from alternative splice sites. Nucleic acid sequences encoding proteins can be DNA or RNA that directs the expression of protein or RNA. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein or RNA. The sequences can also include degenerate codons of the native sequence or sequences that may be introduced to provide codon preference. Thus, a gene refers to a unit of inheritance that occupies a specific locus on a chromosome and consists of transcriptional and/or translational regulatory sequences and/or a coding region and/or non-translated sequences (i.e., introns, 5' and 3' untranslated sequences).

A coding sequence is any nucleotide sequence that contributes to the code for the protein or RNA product of a gene. A non-coding sequence thus refers to any nucleic acid sequence that does not contribute to the code for the protein or RNA product of a gene.

In addition to particular sequences provided, gene sequences to encode for and/or interfere with proteins described herein, as well as associated RNA are available in publicly available databases and publications.

A "vector" is a nucleotide molecule, (e.g., a DNA molecule) derived, for example, from a plasmid, bacteriophage, yeast or virus, into which a nucleotide sequence (e.g., a gene) can be inserted or cloned. A vector preferably contains one or more unique restriction sites and can be capable of autonomous replication in a photosynthetic microorganism. Autonomously replicating vectors include vectors that exist as extra-chromosomal entities, the replication of which is independent of chromosomal replication, e.g., a linear or closed circular plasmid, an extra-chromosomal element, a mini-chromosome, or an artificial chromosome. Vectors can also be integrable with the genome of the photosynthetic microorganism. This type of vector is replicated together with the chromosome(s) into which it has been integrated. Such a vector may include specific sequences that allow recombination into a particular, desired site of the host chromosome. Vectors used within the current disclosure can include any mechanism for assuring self-replication. A vector can include a single vector (or plasmid), two or more vectors, three or more vectors, etc. which together contain the total DNA required for expression of a nucleotide sequence of interest to be expressed in the photosynthetic microorganism.

As indicated, coding sequences to be expressed are operably linked to a promoter, that is, they are placed under the regulatory control of a promoter, which then controls the transcription and optionally the translation of the coding sequence. In the construction of heterologous promoter/structural coding sequence combinations, it is generally preferred to position the promoter at a distance from the coding sequence transcription start site that is approximately the same as the distance between that a promoter and the coding sequence it controls in its natural setting. As is known in the art, some variation in this distance can be accommodated without loss of function. Similarly, the preferred positioning of a regulatory sequence element with respect to a coding sequence to be placed under its control is defined by the positioning of the element in its natural setting; i.e., the genes from which it is derived.

"Constitutive promoters" are typically active, i.e., promote transcription, under most conditions. "Inducible promoters" are typically active only under certain conditions, such as in the presence of a given molecule factor (e.g., IPTG) or a given environmental condition. In the absence of that condition, inducible promoters typically do not allow significant or measurable levels of transcriptional activity.

For example, inducible promoters may be induced according to temperature, pH, a hormone, a metabolite (e.g., lactose, mannitol, an amino acid), light (e.g., wavelength specific), osmotic potential (e.g., salt induced), a heavy metal, or an antibiotic.

In particular embodiments, the promoter controlling the transcription of the coding sequence of interest can be a Cyanobacterial promoter. The promoter can be endogenous to the modified photosynthetic microorganism or can be a promoter, which was modified in order to increase its efficiency. The promoter can also be a heterologous promoter from a different photosynthetic microorganism species, such as a different Cyanobacterial or bacterial species.

In particular embodiments, the coding sequence of interest is placed under the transcriptional control of promoters (P) selected from: PaztA (e.g., from *Anabaena* (*Nostoc*) sp. strain PCC 7120); PBad, Pc1pB1, PcorT (e.g., from *Synechocystis* sp. PCC6803), PcrhC; PcpcB, (e.g., from Cyanobacteria ABICyano1 (SEQ ID NO: 3)); PcpcBA (e.g., from *Synechocystis* PCC6803), PggpS (e.g., from Cyanobacteria ABICyano1: (SEQ ID NO: 4)); PhliB; PhspA; PhtpG; PisiA; PisiB; PlrtA (e.g., from Cyanobacteria ABICyano1; SEQ ID NO: 5)); PnarB; PnblA (e.g., from Cyanobacteria ABICyano1; (SEQ ID NO: 6)); PnirA; PntcA; PpetE; PpetJ (e.g., from Cyanobacteria ABICyano1; (SEQ ID NO: 7)); PpsbA2; PpsbD; PmrgA (e.g., from Cyanobacteria ABICyano1; (SEQ ID NO: 8)); PnblA (e.g., from *Nostoc* sp. PCC7120), PnirA (e.g., from Cyanobacteria ABICyano1), PnrsB (e.g., from *Synechocystis* sp. PCC6803), PnrtA; PntcA; PppsA (e.g., from Cyanobacteria ABICyano1 (SEQ ID NO: 9)); PpsaA; PpsbD; PpstS (e.g., from Cyanobacteria ABICyano1 (SEQ ID NO: 10); PrbcL (e.g., from *Synechocystis* sp. PCC6803), PrbcLS; PrnpA (e.g., from Cyanobacteria ABICyano1 (SEQ ID NO: 11); PrpoA; PrpsL; PTac; Ptcr; PsbA2 (e.g., from *Synechocystis* PCC6803), PsigB, PsmtA (e.g., from *Synechococcus* sp. PCC 7002 and *Synechococcus* PCC 7942); and PziaA (e.g., from Synechocystis sp. PCC6803). Homologous promoters from other species (e.g., *Synechococcus elongatus, Arthrospira maxima, Arthrospira platensis,* and *Cyanobacterium aponinum*) as appropriate can also be used.

PhspA, Pc1pB1, and PhliB can be induced by heat shock (e.g., raising the growth temperature of the photosynthetic microorganism culture (the culture) from 300° C. to 400° C.), cold shock (e.g., reducing the growth temperature of the culture from 300° C. to 20° C.), oxidative stress (e.g., by adding oxidants such as hydrogen peroxide to the culture), or osmotic stress (e.g., by increasing the salinity of the culture). PsigB can be induced by stationary growth, heat shock, and osmotic stress. PntcA and PnblA can be induced by decreasing the concentration of nitrogen in the growth medium and PpsaA and PpsbA2 can be induced by low light or high light conditions. PhtpG can be induced by osmotic stress and heat shock. PcrhC can be induced by cold shock. An increase in copper concentration can be used to induce PpetE, whereas PpetJ is induced by decreasing copper concentration. PaztA, PsmtA, and PziaA can be induced by adding $Zn^{2+}$. PnrsB can be induced by adding $Ni^{2+}$. PcorT can be induced by adding cobalt. Additional details of these promoters can be found, for example, in PCT/E P2009/060526.

The Ptrc promoter is inducible by addition of the chemical IPTG. In the absence of IPTG the promoter has relatively low level of activity and in the presence of IPTG it has a relatively high level of activity. It is not a strictly "on/off" promoter, however. For some genes the low level of activity in the absence of IPTG is enough to cause a phenotype (e.g. expression of N-SrrA). For other genes the higher level of induced activity is required to cause a phenotype (e.g. expression of N-RpaB (see FIG. 4)). Thus, in particular embodiments, uninduced can mean constitutive expression at a low level, such as N-SrrA expression observed in the absence of IPTG.

Useful constitutive or inducible promoters are also described in, for example: Samartzidou et al., *Plant Physiol.,* 1998; 117:225-234; Duran et al., *J. of Biol. Chem.,* 2004; 279:7229-7233; Singh et al., *Arch Microbiol.,* 2006; 186: 273-286; Imamura et al., *FEBS Lett.,* 2003; 554:357-362; Imamura et al., *J. Biol. Chem.,* 2006; 281:2668-2675; Agrawal et al., *Biochem. Biophys. Res. Commun.,* 1999; 255:47-53; Mohamed et al., *Plant Mol. Biol.,* 1989; 13:693-700; Muramatsu et al., *Plant Cell Physiol.,* 2006; 47:878-890; Marin et al., *Plant Physiol.,* 2004; 136:3290-3300; Marin et al., *J. Bacteriol.,* 2002; 184:2870-2877; Qi et al., *Appl. Environ. Microbiol.,* 2005; 71:5678-5684; Maeda et al., *J. Bacteriol.,* 1998; 180:4080-4088; Herranen et al., *Plant Cell Physiol.,* 2005; 46:1484-1493; Buikema et al., *Proc. Natl. Acad. Sci. USA,* 2001; 98:2729-2734; Mary et al., *Microbiol.,* 2004; 150:1271-1281; He et al., *J. Biol. Chem.,* 2001; 276:306-314; Fang et al., *Curr. Microbiol.,* 2004; 49:192-198; and Kappell et al., *Arch. Microbiol.,* 2007; 187:337-342.

In the case that more than one coding sequence of interest is present, then, for example, the first and second coding sequence can be controlled by one promoter thereby forming a transcriptional operon. Alternatively the first and second coding sequence can be operably linked to different first and second promoters, respectively. When more than one promoter is used, all can be constitutive promoters, all can be inducible promoters, or a combination of constitutive and inducible promoters can be used.

Expression control can be tightened when mutations are introduced in the TATA-box, the operator sequence and/or the ribosomal binding site (RBS) of the promoter controlling the expression of the coding sequence so that the promoter has at least 90% sequence identity to an endogenous promoter of the modified photosynthetic microorganism. Examples of these approaches are described below in relation to promoters PnirA, PcorT and PsmtA.

In particular embodiments, PnirA can have the generalized nucleotide sequence of SEQ ID NO: 12 wherein each of the nucleotides n is independently selected from: a, t, c and g and wherein the two (atg)s in the 5'-region of the promoter are the start for NtcB binding sites, gta is the start for the NtcA binding site, ccg denotes the start of the RBS, and the 3'-atg is the start codon for the first recombinant coding sequence transcriptionally controlled by this promoter.

Another generalized DNA sequence of PnirA includes nucleotide changes in the RBS leading to the generalized DNA sequence of SEQ ID NO: 13. In particular embodiments the modified PnirA can include changes in the operator region (binding site for NtcB and NtcA) and the TATA box leading to the generalized nucleotide sequence of SEQ ID NO: 14. Another variant of PnirA combines changes in the RBS, operator region and the TATA box to form SEQ ID NO: 15.

Particular embodiments provide the $Co^{2+}$-inducible PcorT, which has the general nucleotide sequence of SEQ ID NO: 16 wherein each of the nucleotides n is independently selected from: a, t, c and g and wherein the 5'-cat is the start codon of corR (antisense orientation) and the 3'-atg is the start codon for the first recombinant coding sequence transcriptionally controlled by this promoter. A modified variant of PcorT includes changes in the RBS having SEQ ID NO: 17. Another variant of PcorT includes changes in the TATA box having the general sequence of SEQ ID NO: 18. A third modified PcorT combines the RBS and TATA box modifications into SEQ ID NO: 19.

Furthermore the $Zn^{2+}$-inducible PsmtA from *Synechococcus* PCC 7002 can be used having the generalalized nucleotide sequence of SEQ ID NO: 20. Changes in the RBS can lead to the following generalized nucleotide sequences of SEQ ID NO: 21 or SEQ ID NO: 22. Again, homologous sequences from other species (e.g., *Synechococcus elongatus, Arthrospira maxima, Arthrospira platensis,* and *Cyanobacterium aponinum*) as appropriate may also be used.

As suggested, particular embodiments include codon optimization. Codons preferred by a particular photosynthetic microorganism can be selected to, for example, increase the rate of protein expression or to produce a recombinant RNA transcript having desirable properties, such as a half-life which is longer than that of a transcript generated from the naturally occurring sequence. Such nucleotide sequences are typically referred to as "codon-optimized."

At least some of the nucleotide sequences to be expressed in modified photosynthetic microorganisms can be codon-optimized for optimal expression in a chosen Cyanobacterial strain. The underlying rationale is that the codon usage frequency of highly expressed genes is generally correlated to the host cognate tRNA abundance. (Bulmer, Nature, 1987; 325:728-730). In particular embodiments, the codon optimization is based on the Cyanobacteria ABICyano1 (as well as its close relative species) codon usage frequency (host codon bias), in order to achieve desirable heterologous gene expression (Sharp et al., 1987; *Nucleic Acids Res.,* 15:1281-1295). In particular embodiments, codon optimization can be based on *Synechococcus elongatus* PCC 7942.

Codon optimization can be performed with the assistance of publicly available software, such as Gene Designer (DNA 2.0). Additional modifications to minimize unwanted restriction sites, internal Shine-Dalgarno sequences, and other sequences such as internal termination sequences and repeat sequences can also be performed. These general codon-optimization methods have been shown to result in up to 1,000 fold higher expression of heterologous genes in target organisms (Welch et al., PLoS One 4, 2009; e7002; and Welch et al., *J. of the Royal Society,* 2009; Interface 6 (Suppl 4):S467-S476.

In particular embodiments, a gene that has at least 85% sequence identity; 86% sequence identity; 87% sequence identity; 88% sequence identity; 89% sequence identity; 90% sequence identity; 91% sequence identity; 92% sequence identity; 93% sequence identity; 94% sequence identity; 95% sequence identity; 96% sequence identity; 97% sequence identity; 98% sequence identity; or 99% sequence identity to SEQ ID NO: 23, SEQ ID NO: 33, SEQ ID NO: 41 and/or SEQ ID NO: 43 can be placed behind a promoter in a neutral site to drive expression of N-RpaB, N-SrrA, guide RNA and/or Cas 9 respectively.

In particular embodiments, genes that encode a protein or guide RNA having 85% sequence identity; 86% sequence identity; 87% sequence identity; 88% sequence identity; 89% sequence identity; 90% sequence identity; 91% sequence identity; 92% sequence identity; 93% sequence identity; 94% sequence identity; 95% sequence identity; 96% sequence identity; 97% sequence identity; 98% sequence identity; or 99% sequence identity to SEQ ID NO: 2; SEQ ID NO: 34; SEQ ID NO: 42 or SEQ ID NO: 44, can be placed behind a promoter in a neutral site to drive expression of N-RpaB, N-SrrA guide RNA or Cas9 variants.

Variants of N-RpaB, N-SrrA or Cas9 include proteins having one or more amino acid additions, deletions, stop positions, or substitutions, as compared to N-RpaB (SEQ ID NO: 2), N-SrrA (SEQ ID NO: 34) or Cas9 (SEQ ID NO: 44). Variants of N-RpaB N-SrrA and Cas9 have at least 85% sequence identity; 86% sequence identity; 87% sequence identity; 88% sequence identity; 89% sequence identity; 90% sequence identity; 91% sequence identity; 92% sequence identity; 93% sequence identity; 94% sequence identity; 95% sequence identity; 96% sequence identity; 97% sequence identity; 98% sequence identity; or 99% sequence identity to N-RpaB, N-SrrA or Cas9 and cause a statistically significant increase in a photosynthetic microorganism's photosynthetic capacity as compared to a photosynthetic microorganism that has not been modified to have reduced RpaB pathway activity. Variants of Cas9 cause a statistically significant increase in a photosynthetic microorganism's photosynthetic capacity as compared to a photosynthetic microorganism that has not been modified to have reduced RpaB pathway activity in combination with guide RNA or variants thereof.

An amino acid substitution of N-RpaB, N-SrrA, or Cas9 can be a conservative or a non-conservative substitution. A "conservative substitution" involves a substitution found in one of the following conservative substitutions groups: Group 1: Alanine (Ala; A), Glycine (Gly; G), Serine (Ser; S), Threonine (Thr; T); Group 2: Aspartic acid (Asp; D), Glutamic acid (Glu; E); Group 3: Asparagine (Asn; N), Glutamine (Gln; Q); Group 4: Arginine (Arg; R), Lysine (Lys; K), Histidine (His; H); Group 5: Isoleucine (Ile, I), Leucine (Leu; L), Methionine (Met; M), Valine (Val; V); and Group 6: Phenylalanine (Phe; F), Tyrosine (Tyr; Y), Tryptophan (Trp; W).

Additionally, amino acids can be grouped into conservative substitution groups by similar function, chemical structure, or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cys; acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. As indicated, in particular embodiments, conservative substitutions can include substituting Asp56 with Glu, Ser, Thr or Tyr.

Non-conservative substitutions include those that affect the function of N-RpaB, N-SrrA or Cas9 in a statistically-significant manner. Non-conservative substitutions include those in which (i) a hydrophilic residue (e.g. Ser or Thr) is substituted by a hydrophobic residue (e.g. Leu, Ile, Phe, Val, or Ala); (ii) a Cys or Pro is substituted by any other residue; (iii) a residue having an electropositive side chain (e.g. Lys, Arg, or His) is substituted by an electronegative residue (e.g. Gln or Asp); or (iv) a residue having a bulky side chain (e.g. Phe), is substituted by one not having a bulky side chain, (e.g. Gly). In particular embodiments, non-conservative substitutions can be made at Asp56 in sequences having 90% or more sequence identity with wild-type RpaB or at Asp64 in sequences having 90% or more sequence identity with wild-type SrrA to create decoys with non-functioning phospho-receiver domains. Additional information is found in Creighton (1984) Proteins, W. H. Freeman and Company.

In particular embodiments, N-RpaB variants retain Asp at position 56. In particular embodiments, no variant positions are found at position 50, 51, 52, 53, 54, 55, 56, 57, 58, 59 or 60. In particular embodiments, N-SrrA variants retain Asp at position 64. In particular embodiments, no variant positions are found at position 58, 59, 60, 61, 62, 63, 64, 65, 66, 67 or 68.

Variants of guide RNA include RNA sequences having one or more nucleotide additions, deletions, stop positions, or substitutions, as compared to SEQ ID NO: 42. Variants of guide RNA have at least 85% sequence identity; 86% sequence identity; 87% sequence identity; 88% sequence identity; 89% sequence identity; 90% sequence identity; 91% sequence identity; 92% sequence identity; 93% sequence identity; 94% sequence identity; 95% sequence identity; 96% sequence identity; 97% sequence identity; 98% sequence identity; or 99% sequence identity to SEQ ID NO: 42 and function with Cas9 or variants thereof to cause a statistically significant increase in a photosynthetic microorganism's photosynthetic capacity as compared to a photosynthetic microorganism that has not been modified to have reduced RpaB pathway activity.

Variants incorporating stop positions can be biologically active fragments. Biologically active fragments have 0.1, 0.5, 1, 2, 5, 10, 12, 14, 16, 18, 20, 22, 24, 26, 28, 30, 35, 40, 45, 50, 55, 60, 65, 70, 75, 80, 85, 90, 95, 96, 97, 98, 99, 100, 110, 120, 150, 200, 300, 400, 500, 600, 700, 800, 900, 1000% or more of the activity of a reference sequence. A reference sequence refers generally to an amino acid sequence, RNA sequence, or a nucleic acid coding sequence expressing a protein and/or guide RNA that reduces RpaB pathway activity as described herein.

"% sequence identity" refers to a relationship between two or more sequences, as determined by comparing the sequences. In the art, "identity" also means the degree of sequence relatedness between sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine sequence identity are designed to give the best match between the sequences tested. Methods to determine sequence identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp, *CABIOS,* 1989; 5:151-153 with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul et al., *J. Mol. Biol.,* 1990; 215:403-410; DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y.). Within the context of this disclosure it will be understood that where sequence analysis software is used for analysis, the results of the analysis are based on the "default values" of the program referenced. As used herein "default values" will mean any set of values or parameters which originally load with the software when first initialized.

Insertion (e.g., transformation) of a nucleotide sequence (e.g., a vector) into a photosynthetic microorganism can be achieved using any appropriate method including, for example, natural transformation (e.g., natural DNA uptake; see, e.g., Chung et al., *FEMS Microbiol. Lett.,* 1998; 164: 353-361; Frigaard et al., *Methods Mol. Biol.,* 2004; 274: 325-40; Zang et al., *J. Microbiol.,* 2007; 45:241-245); conjugation (e.g., bi- or tri-parental mating), transduction, glass bead transformation (see, e.g., Kindle et al., *J. Cell Biol.,* 1989; 109:2589-601; Feng et al., *Mol. Biol. Rep.,* 2009; 36:1433-9; U.S. Pat. No. 5,661,017), silicon carbide whisker transformation (see, e.g., Dunahay et al., *Methods Mol. Biol.,* 1997; 62: 503-9), biolistics (see, e.g., Dawson et al., *Curr. Microbiol.,* 1997; 35: 356-62; Hallmann et al., *Proc. Natl. Acad. USA,* 1997; 94:7469-7474; Doestch et al., *Curr. Genet.,* 2001; 39:49-60; Jakobiak et al., *Protist,* 2004; 155: 381-93; Ramesh et al., *Methods Mol. Biol.,* 2004; 274: 355-307; Tan et al., *J. Microbiol.,* 2005; 43:361-365; Steinbrenner et al., *Appl Environ. Microbiol.,* 2006; 72:7477-7484; Kroth, *Methods Mol. Biol.,* 2007; 390:257-267; U.S. Pat. No. 5,661,017); electroporation (see, e.g., Kjaerulff et al., *Photosynth. Res.,* 1994; 41:277-283; Iwai et al., *Plant Cell Physiol.,* 2004; 45:171-5; Ravindran et al., *J. Microbiol. Methods,* 2006; 66:174-6; Sun et al., *Gene,* 2006; 377: 140-149; Wang et al., *Appl. Microbiol. Biotechnol.,* 2007; 76:651-657; Chaurasia et al., *J. Microbiol. Methods,* 2008; 73:133-141; Ludwig et al., *Appl. Microbiol. Biotechnol.,* 2008; 78:729-35), laser-mediated transformation, or incubation with DNA in the presence of or after pre-treatment with any of poly(amidoamine) dendrimers (see, e.g., Pasupathy et al., *J. Biotechnol.,* 2008; 3:1078-82), polyethylene glycol (see, e.g., Ohnuma et al., *Plant Cell Physiol.,* 2008; 49:117-120), cationic lipids (see, e.g., Muradawa et al., *J. Biosci. Bioeng.,* 2008; 105: 77-80), dextran, calcium phosphate, or calcium chloride (see, e.g., Mendez-Alvarez et al., *J. Bacteriol.,* 1994; 176:7395-7397), optionally after treatment of the cells with cell wall-degrading enzymes (see, e.g., Perrone et al., *Mol. Biol. Cell,* 1998; 9:3351-3365).

In addition, the vector can be modified to allow for integration into a chromosome by adding an appropriate DNA sequence homologous to the target region of the photosynthetic microorganism genome, or through in vivo transposition by introducing the mosaic ends (ME) to the vector. Once a plasmid is established in a photosynthetic microorganism, it can be present, for example, at a range of from 1 to many copies per cell.

Insertion methods described above can be used for introducing nucleotide sequences (e.g., vectors) into Cyanobacterial cells harboring an extracellular polymer layer (EPS). Non-limiting examples for Cyanobacteria with an EPS include several *Nostoc* and *Anabaena* strains, such as *Nostoc commune,* and *Anabanena cylindrica* and several *Cyanothece* sp. strains, such as *Cyanothece* PCC9224, *Cyanothece* CA 3, *Cyanothece* CE 4, *Cyanothece* ET5, *Cyanothece* ET 2, and *Cyanospira capsulate* ATCC 43193. Further examples of Cyanobacteria with an EPS include *Aphanocapsa, Cyanobacterium, Anacystis, Chroococcus, Gloeothece, Microcystis, Synechocystis, Lyngbya, Microcoleus, Oscillatoria, Phormidium, Arthrospira, Anabaena, Cyanospira, Nostoc, Scytonema, Tolypothrix, Chlorogloeopsis, Fischerella,* and *Mastigocladus* (see for example: De Philippis et al., *J. of Applied Phycology*, 2001; 13:293-299; De Philippis et al., *FEMS Microbiol. Reviews*, 1998; 22:151-175).

In Cyanobacteria, restriction systems can create barriers to the introduction of exogenous nucleotide sequences. Restriction systems include a restriction enzyme and a specific DNA methyltransferase. Specific methylation of the restriction enzyme recognition sequence protects DNA in the photosynthetic microorganism from degradation by the corresponding restriction enzyme. Knowledge of particular restriction systems within particular bacterial cell types can allow one to protect exogenous nucleotide sequences by methylating it at particular sites to prevent degradation by the photosynthetic microorganism's restriction system restriction enzyme(s). Thus, an understanding of these restriction systems can be helpful in choosing appropriate transformation protocols for particular bacteria. Particular restriction systems for different Cyanobacterial cells can be found at rebase.neb.com.

Nucleotide sequences used herein can include selectable markers to identify modified photosynthetic microorganisms. Selectable markers can be any identifying factor, usually an antibiotic or chemical resistance gene, that is able to be selected for based upon the marker gene's effect, such as resistance to an antibiotic, resistance to a herbicide, colorimetric markers, enzymes, fluorescent markers, and the like, wherein the effect is used to track the transformation of a nucleotide sequence of interest and/or to identify a modified photosynthetic microorganism that has inherited the nucleotide sequence of interest. Examples of selectable marker genes known and used in the art include: genes providing resistance to ampicillin, gentamycin, hygromycin, kanamycin, spectinomycin, streptomycin, fluorescent proteins (e.g., from Promega Corporation, Invitrogen, Clontech, Stratagene, BD Biosciences Pharmingen, Evrogen JSC), and the like.

Modified photosynthetic microorganisms, including Cyanobacteria, can be cultured or cultivated according to techniques known in the art, such as those described in Acreman et al., *J. of Industrial Microbiol. and Biotechnol.*, 1994; 13:193-194), in addition to photobioreactor based techniques, such as those described in Nedbal et al., *Biotechnol. Bioeng.*, 2008; 100:902-10. One example of typical laboratory culture conditions for Cyanobacteria is growth in BG-11 medium (ATCC Medium 616) at 30° C. in a vented culture flask with constant agitation and constant illumination at 30-100 µmole photons $m^{-2} sec^{-1}$.

Additional media for culturing Cyanobacteria, include Aiba and Ogawa (AO) Medium, Allen and Amon Medium plus Nitrate (ATCC Medium 1142), Antia's (ANT) Medium, Aquil Medium, Ashbey's Nitrogen-free Agar, ASN-III Medium, ASP 2 Medium, ASW Medium (Artificial Seawater and derivatives), ATCC Medium 617 (BG-11 for Marine Blue-Green Algae; Modified ATCC Medium 616 [BG-11 medium]), ATCC Medium 819 (Blue-green Nitrogen-fixing Medium; ATCC Medium 616 [BG-11 medium] without $NO_3$), ATCC Medium 854 (ATCC Medium 616 [BG-11 medium] with Vitamin $B_{12}$), ATCC Medium 1047 (ATCC Medium 957 [MN marine medium] with Vitamin $B_{12}$), ATCC Medium 1077 (Nitrogen-fixing marine medium; ATCC Medium 957 [MN marine medium] without $NO_3$), ATCC Medium 1234 (BG-11 Uracil medium; ATCC Medium 616 [BG-11 medium] with uracil), Beggiatoa Medium (ATCC Medium 138), *Beggiatoa* Medium 2 (ATCC Medium 1193), BG-11 Medium for Blue Green Algae (ATCC Medium 616), Blue-Green (BG) Medium, Bold's Basal (BB) Medium, Castenholtz D Medium, Castenholtz D Medium Modified (Halophilic Cyanobacteria), Castenholtz DG Medium, Castenholtz DGN Medium, Castenholtz ND Medium, *Chloroflexus* Broth, *Chloroflexus* Medium (ATCC Medium 920), Chu's #10 Medium (ATCC Medium 341), Chu's #10 Medium Modified, Chu's #11 Medium Modified, DCM Medium, DYIV Medium, E27 Medium, E31 Medium and Derivatives, f/2 Medium, f/2 Medium Derivatives, Fraquil Medium (Freshwater Trace Metal-Buffered Medium), Gorham's Medium for Algae (ATCC Medium 625), h/2 Medium, Jaworski's (JM) Medium, K Medium, L1 Medium and Derivatives, MN Marine Medium (ATCC Medium 957), Plymouth Erd-schreiber (PE) Medium, *Prochlorococcus* PC Medium, Proteose Peptone (PP) Medium, Prov Medium, Prov Medium Derivatives, S77 plus Vitamins Medium, S88 plus Vitamins Medium, Saltwater Nutrient Agar (SNA) Medium and Derivatives, SES Medium, SN Medium, Modified SN Medium, SNAX Medium, Soil/Water Biphasic (S/W) Medium and Derivatives, SOT Medium for *Arthrospira* (*Spirulina*): ATCC Medium 1679, *Spirulina* (SP) Medium, van Rijn and Cohen (RC) Medium, Walsby's Medium, Yopp Medium, and Z8 Medium, among others.

Figure 5:
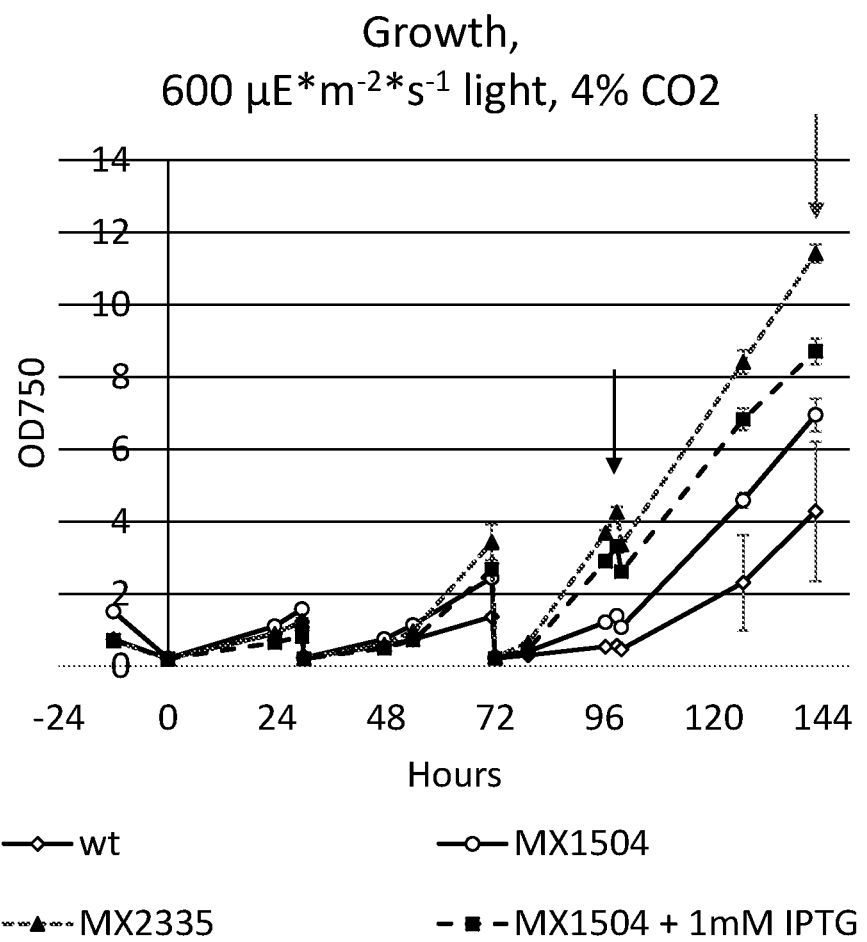
FIG. 5 depicts growth, as measured by optical density at 750 nm (OD750) of wild type, MX2335, and MX1504 with and without 1 mM IPTG after repeated dilutions with fresh media. Arrows indicate time points at which sample aliquots were removed for dry weight determination, which is given in FIG. 6.

Particular embodiments disclosed herein demonstrate increased photoautotrophic growth of photosynthetic microorganisms with reduced RpaB pathway activity. The advantage of Rpa-B down regulation on photoautotrophic growth is evident shortly after culturing begins with the increased growth becoming more apparent as the culture is propagated over time. See, for example, FIG. 5. In particular embodiments, a volume fraction of the liquid culture can be replaced with an equivalent volume of new growth media during the culturing period, as is understood by one of ordinary skill in the art.

Modified photosynthetic microorganisms disclosed herein have increased photosynthetic capacity. Photosynthetic capacity is defined here as the maximum rate of electron transport through the photosynthetic electron transport chain. Photosynthetic capacity can be independently measured for different segments of the photosynthetic electron transport chain. For the segment through PSII, photosynthetic capacity can be measured by determining the rate of oxygen evolution of whole cells in the presence of para-benzoquinone and potassium ferricyanide, which serve to accept electrons directly from PSII, allowing for PSII oxygen evolution to run at its maximal rate, independent of down-stream proteins in the electron transport chain. For the segment including the entire electron transport chain through PSI, increased photosynthetic capacity can be measured by determining the rate of oxygen uptake of whole cells in the presence of methyl viologen and potassium cyanide, which serve to accept electrons directly from PSI, allowing for the entire electron transport chain to run at maximal rate, independent of down-stream proteins in, e.g., carbon fixation or nitrate reduction. In this latter embodiment, the uptake rate of oxygen is a measure of the photosynthetic capacity because of the specific chemistry of the assay involving methyl viologen, which follows the following half reactions:

$$2 H_2O \rightarrow 4H^+ + 4e^- + O_2$$

$$2O_2 + 4H^+ + 4e^- \rightarrow 2H_2O_2$$

This leads to a balanced equation below, where 1 molecule of oxygen is consumed for every molecule of $O_2$ that could potentially be evolved:

$$2 H_2O + O_2 \rightarrow 2H_2O_2$$

Increased photosynthetic capacity can increase total carbon fixation, production of carbon containing compounds, and growth (biomass accumulation).

Figure 6:
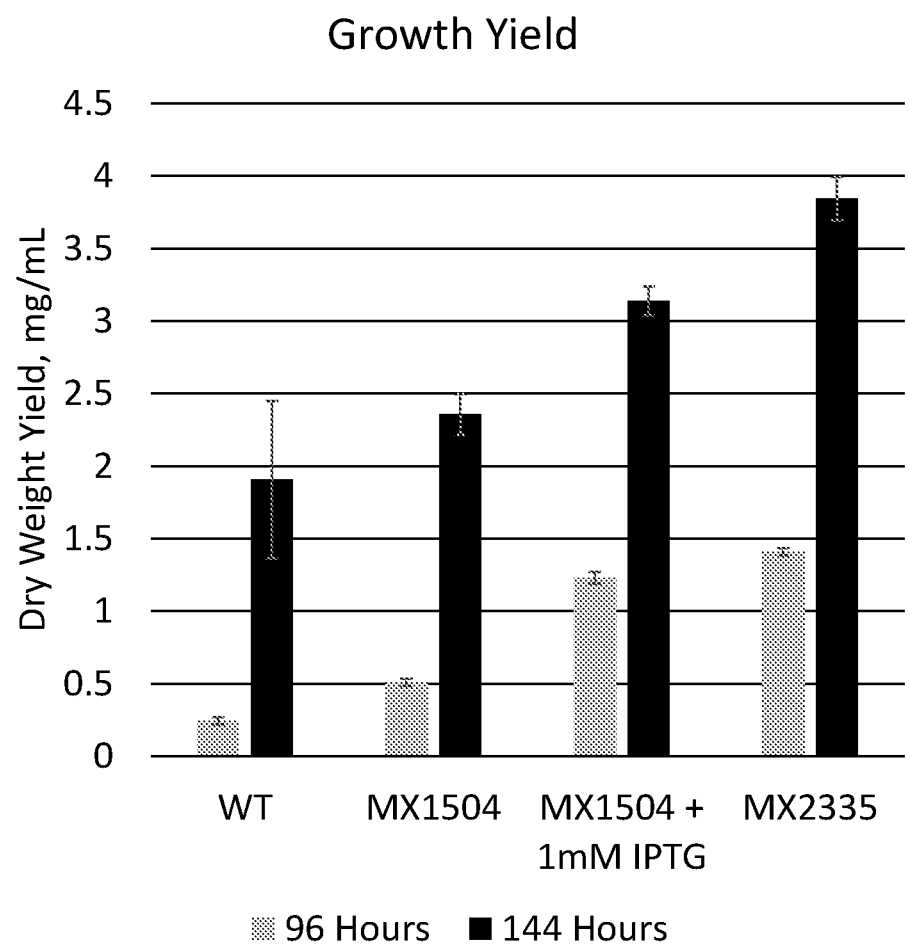
FIG. 6 depicts growth yields of WT, MX1504 without and with 1 mM IPTG, and MX2335 as determined 96 and 144 hours into the experiment. This growth experiment is the same as that for which data in FIG. 5 is presented.

Particular embodiments include increasing photosynthetic biomass accumulation from photoautotrophic growth of a photosynthetic microorganism comprising modifying the photosynthetic microorganism to down-regulate RpaB pathway activity within the photosynthetic microorganism as compared to photosynthetic biomass accumulation of the same species. See, for example, FIG. 6.

The Exemplary Embodiments below describe particular embodiments of the disclosure. Those of ordinary skill in the art should recognize in light of the present disclosure that many changes can be made to the specific embodiments disclosed herein and still obtain a like or similar result without departing from the spirit and scope of the disclosure.

EXEMPLARY EMBODIMENTS

1. A modified photosynthetic microorganism with increased photosynthetic capacity as compared to a photosynthetic microorganism of the same species without the modification.
2. A modified photosynthetic microorganism of embodiment 1 wherein the modified photosynthetic microorganism includes a genetic modification.
3. A modified photosynthetic microorganism of embodiment 1 or a genetically-modified photosynthetic microorganism of embodiment 2 wherein the increased photosynthetic capacity results from decreased RpaB pathway activity.
4. A genetically-modified photosynthetic microorganism of embodiment 3 wherein the decreased RpaB pathway activity results from (i) expression of at least one exogenous nucleotide sequence and/or (ii) a wild-type nucleotide sequence deletion wherein (i) and/or (ii) decreases RpaB pathway activity as compared to a photosynthetic microorganism of the same species without the modification(s).
5. A genetically-modified photosynthetic microorganism of embodiment 4 wherein the exogenous nucleotide sequence (i) results in translation of an incomplete or unstable RpaB protein; (ii) results in translation of an RpaB protein that folds incorrectly; (iii) reduces transcription of the RpaB gene; (iv) results in incomplete transcription of the RpaB gene; (v) interferes with an encoded RpaB RNA transcript and/or (vi) reduces translation of RpaB.
6. A genetically-modified photosynthetic microorganism of embodiment 4 wherein the exogenous nucleotide sequence is a foreign set of base pairs inserted or substituted into the RpaB coding region.
7. A genetically-modified photosynthetic microorganism of embodiment 4 wherein the exogenous nucleotide sequence is an antisense sequence that interferes with transcription or translation of the RpaB gene.
8. A genetically-modified photosynthetic microorganism of embodiment 4 wherein the exogenous nucleotide sequence expresses an RpaB decoy under the control of a promoter.
9. A genetically-modified photosynthetic microorganism of any of the preceding embodiments including at least two of the described exogenous nucleotide sequences, at least three of the described exogenous nucleotide sequences, at least four of the described exogenous nucleotide sequences, or at least five of the described exogenous nucleotide sequences.
10. A genetically-modified photosynthetic microorganism of embodiments 8 or 9 wherein the RpaB decoy is an N-terminal fragment of RpaB or SrrA including a phosphor-receiver domain but no DNA binding domain or a non-functional DNA binding domain.
11. A genetically-modified photosynthetic microorganism of any of embodiments 8-10 wherein the RpaB decoy is a fragment of wild type RpaB including Asp56 or a conservative substitution thereof or an N-terminal fragment of wild type SrrA including Asp64 or a conservative substitution thereof.
12. A genetically-modified photosynthetic microorganism of any of embodiments 8-10 wherein the RpaB decoy is N-RpaB or N-SrrA.
13. A genetically-modified photosynthetic microorganism of any of embodiments 8-10 wherein the RpaB decoy is an N-RpaB variant that maintains Asp56 or a conservative substitution thereof or an N-SrrA variant that maintains Asp64 or a conservative substitution thereof.
14. A genetically-modified photosynthetic microorganism of any of embodiments 4-13 wherein the exogenous nucleotide sequence includes SEQ ID NO: 23 or SEQ ID NO: 33.
15. A genetically-modified photosynthetic microorganism of any of embodiments 4-13 wherein the exogenous nucleotide sequence includes SEQ ID NO: 23 and SEQ ID NO: 33.
16. A genetically-modified photosynthetic microorganism of any of embodiments 4-15 wherein the exogenous nucleotide sequence expresses guide RNA and a Cas9 protein.
17. A genetically-modified photosynthetic microorganism of any of embodiments 4-16 wherein the exogenous nucleotide sequence includes SEQ ID NO: 41.
18. A genetically-modified photosynthetic microorganism of any of embodiments 4-17 wherein the exogenous nucleotide sequence includes SEQ ID NO: 43.
19. A genetically-modified photosynthetic microorganism of any of embodiments 4-18 wherein the exogenous nucleotide sequence includes SEQ ID NO: 41 and SEQ ID NO: 43.
20. A genetically-modified photosynthetic microorganism of embodiment 16 wherein the guide RNA includes SEQ ID NO: 42 or a biologically active fragment thereof.
21. A genetically-modified photosynthetic microorganism of embodiment 16 or 20 wherein the Cas9 protein includes SEQ ID NO: 44 or a variant thereof including a conservative substitution.
22. A genetically-modified photosynthetic microorganism of embodiment 16 or 20 wherein the Cas9 protein includes a substitution at amino acid positions 10 and/or 841.
23. A genetically-modified photosynthetic microorganism of any of embodiments 8-22 wherein the promoter is an inducible promoter.
24. A genetically-modified photosynthetic microorganism of any of embodiments 8-22 wherein the promoter is endogenous to the genome of the genetically-modified photosynthetic microorganism.
25. A genetically-modified photosynthetic microorganism of any of embodiments 1-24 wherein the genetically-modified photosynthetic microorganism is a Cyanobacteria.
26. A genetically-modified photosynthetic microorganism of any of embodiments 1-24 wherein the genetically-modified photosynthetic microorganism is a Cyanobacteria selected from *Synechococcus elongatus*, *Arthrospira maxima*, *Arthrospira platensis*, and *Cyanobacterium aponinum*.

27. A genetically-modified photosynthetic microorganism of any of embodiments 1-26 wherein the genetically-modified photosynthetic microorganism has increased photosynthetic capacity as compared to a wild type photosynthetic microorganism of the same species.

28. A method for increasing photosynthetic capacity and/or biomass accumulation of a photosynthetic microorganism including modifying the photosynthetic microorganism to reduce RpaB pathway activity within the photosynthetic microorganism as compared to a photosynthetic microorganism of the same species without the modification or as compared to a wild type photosynthetic microorganism of the same species.

29. A method of embodiment 28 wherein the modifying includes genetically modifying the photosynthetic microorganism.

30. A method of embodiment 28 or 29 wherein the modifying includes inserting an exogenous nucleotide sequence into the photosynthetic microorganism or deleting an endogenous nucleotide sequence from the photosynthetic microorganism.

31. A method of embodiment 30 wherein the exogenous nucleotide sequence (i) results in translation of an incomplete or unstable RpaB protein; (ii) results in translation of an RpaB protein that folds incorrectly; (iii) reduces transcription of the RpaB gene; (iv) results in incomplete transcription of the RpaB gene; (v) interferes with an encoded RpaB RNA transcript and/or (vi) reduces translation of RpaB.

32. A method of any of embodiments 28-31 wherein modifying includes inserting or substituting a foreign set of base pairs into the RpaB coding region.

33. A method of any of embodiments 28-32 wherein modifying includes inserting an antisense sequence that interferes with transcription or translation of the RpaB gene.

34. A method of any of embodiments 28-33 wherein the modifying includes inserting an exogenous nucleotide sequence that expresses an RpaB decoy under the control of a promoter into the photosynthetic microorganism.

35. A method of embodiment 34 wherein the RpaB decoy is an N-terminal fragment of RpaB or SrrA including a phosphor-receiver domain but no DNA binding domain or a non-functional DNA binding domain.

36. A method of embodiment 34 or 35 wherein the expressed RpaB decoy is an N-terminal fragment of wild type RpaB including Asp56 or a conservative substitution thereof an N-terminal fragment of wild type SrrA including Asp64 or a conservative substitution thereof.

37. A method of embodiment 34 or 35 wherein the expressed RpaB decoy is N-RpaB or N-SrrA.

38. A method of embodiment 34 or 35 wherein the expressed RpaB decoy is an N-RpaB variant that maintains Asp56 or a conservative substitution thereof or an N-SrrA variant that maintains Asp64 or a conservative substitution thereof.

39. A method of embodiment 34 wherein the exogenous nucleotide sequence includes SEQ ID NO: 23 or SEQ ID NO: 33.

40. A method of embodiment 34 wherein the exogenous nucleotide sequence includes SEQ ID NO: 23 and SEQ ID NO: 33.

41. A method of any of embodiments 28-40 wherein the exogenous nucleotide sequence expresses guide RNA and a Cas9 protein.

42. A method of embodiment 41 wherein the exogenous nucleotide sequence includes SEQ ID NO: 41.

43. A method of embodiment 41 or 42 wherein the exogenous nucleotide sequence includes SEQ ID NO: 43.

44. A method of any of embodiments 41-43 wherein the exogenous nucleotide sequence includes SEQ ID NO: 41 and SEQ ID NO: 43.

45. A method of any of embodiments 41-44 wherein the guide RNA includes SEQ ID NO: 42 or a biologically active fragment thereof.

46. A method of any of embodiments 41-45 wherein the Cas9 protein includes SEQ ID NO: 44 or a variant thereof including a conservative substitution.

47. A method of any of embodiments 41-46 wherein the Cas9 protein includes a substitution at amino acid positions 10 and/or 841.

48. A method of any of embodiments 34-47 wherein the promoter is an inducible promoter.

49. A method of any of embodiments 34-48 wherein the promoter is endogenous to the genome of the genetically-modified photosynthetic microorganism.

50. A method of any of embodiments 28-49 wherein the genetically-modified photosynthetic microorganism is a Cyanobacteria.

51. A method of any of embodiments 28-50 wherein the genetically-modified photosynthetic microorganism is a Cyanobacteria selected from *Synechococcus elongatus, Arthrospira maxima, Arthrospira platensis,* and *Cyanobacterium aponinum.*

52. A method of any of embodiments 28-51 wherein the genetically-modified photosynthetic microorganism has increased photosynthetic capacity as compared to a photosynthetic microorganism of the same species without the modification or as compared to a wild type photosynthetic microorganism of the same species.

53. A method of any of embodiments 28-52 wherein the genetically-modified photosynthetic microorganism shows increased photosynthetic biomass accumulation from photoautotrophic growth as compared to a photosynthetic microorganism of the same species without the modification or as compared to a wild type photosynthetic microorganism of the same species.

54. A method of increasing photoautotrophic growth of a photosynthetic microorganism including
modifying the photosynthetic microorganism to reduce RpaB pathway activity within the photosynthetic microorganism as compared to a photosynthetic microorganism of the same species without the modification or as compared to a wild type photosynthetic microorganism of the same species and
culturing the modified photosynthetic microorganism in a liquid culture,
thereby increasing photoautotrophic growth of the photosynthetic microorganism as compared to the photosynthetic microorganism of the same species without the modification or as compared to the wild type photosynthetic microorganism of the same species.

55. A method of embodiment 54 wherein the modifying includes genetically modifying the photosynthetic microorganism.

56. A method of embodiment 54 or 55 wherein the modifying includes inserting an exogenous nucleotide sequence into the photosynthetic microorganism or deleting an endogenous nucleotide sequence from the photosynthetic microorganism.

57. A method of embodiment 56 wherein the exogenous nucleotide sequence (i) results in translation of an incomplete or unstable RpaB protein; (ii) results in translation of an RpaB protein that folds incorrectly; (iii) reduces transcription of the RpaB gene; (iv) results in incomplete transcription of the RpaB gene; (v) interferes with an encoded RpaB RNA transcript and/or (vi) reduces translation of RpaB.
58. A method of any of embodiments 54-57 wherein modifying includes inserting or substituting a foreign set of base pairs into the RpaB coding region.
59. A method of any of embodiments 54-58 wherein modifying includes inserting an antisense sequence that interferes with transcription or translation of the RpaB gene.
60. A method of any of embodiments 54-59 wherein the modifying includes inserting an exogenous nucleotide sequence that expresses an RpaB decoy under the control of a promoter into the photosynthetic microorganism.
61. A method of embodiment 60 wherein the RpaB decoy is an N-terminal fragment of RpaB or SrrA including a phosphor-receiver domain but no DNA binding domain or a non-functional DNA binding domain.
62. A method of embodiment 60 or 61 wherein the expressed RpaB decoy is an N-terminal fragment of wild type RpaB including Asp56 or a conservative substitution thereof an N-terminal fragment of wild type SrrA including Asp64 or a conservative substitution thereof.
63. A method of embodiment 60 or 61 wherein the expressed RpaB decoy is N-RpaB or N-SrrA.
64. A method of embodiment 60 or 61 wherein the expressed RpaB decoy is an N-RpaB variant that maintains Asp56 or a conservative substitution thereof or an N-SrrA variant that maintains Asp64 or a conservative substitution thereof.
65. A method of embodiment 60 wherein the exogenous nucleotide sequence includes SEQ ID NO: 23 or SEQ ID NO: 33.
66. A method of embodiment 60 wherein the exogenous nucleotide sequence includes SEQ ID NO: 23 and SEQ ID NO: 33.
67. A method of any of embodiments 54-66 wherein the exogenous nucleotide sequence expresses guide RNA and a Cas9 protein.
68. A method of embodiment 67 wherein the exogenous nucleotide sequence includes SEQ ID NO: 41.
69. A method of embodiment 67 or 68 wherein the exogenous nucleotide sequence includes SEQ ID NO: 43.
70. A method of any of embodiments 67-69 wherein the exogenous nucleotide sequence includes SEQ ID NO: 41 and SEQ ID NO: 43.
71. A method of any of embodiments 67-70 wherein the guide RNA includes SEQ ID NO: 42 or a biologically active fragment thereof.
72. A method of any of embodiments 67-71 wherein the Cas9 protein includes SEQ ID NO: 44 or a variant thereof including a conservative substitution.
73. A method of any of embodiments 67-72 wherein the Cas9 protein includes a substitution at amino acid positions 10 and/or 841.
74. A method of any of embodiments 60-73 wherein the promoter is an inducible promoter.
75. A method of any of embodiments 60-74 wherein the promoter is endogenous to the genome of the genetically-modified photosynthetic microorganism.
76. A method of any of embodiments 54-75 wherein the genetically-modified photosynthetic microorganism is a Cyanobacteria.
77. A method of any of embodiments 54-76 wherein the genetically-modified photosynthetic microorganism is a Cyanobacteria selected from *Synechococcus elongatus, Arthrospira maxima, Arthrospira platensis,* and *Cyanobacterium aponinum.*

When an inserted exogenous promoter is endogenous to the genome of the genetically-modified photosynthetic microorganism, this means that an extra copy of a wild-type promoter of the species is inserted as part of a genetic construct.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically-significant reduction in a modified Cyanobacteria's increased photosynthetic capacity.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, if references have been made to patents, printed publications, journal articles and other written text throughout this specification (referenced materials herein), each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

SEQUENCE LISTING

```
<160> NUMBER OF SEQ ID NOS: 44

<210> SEQ ID NO 1
<211> LENGTH: 8
<212> TYPE: PRT
<213> ORGANISM: Cyanobacterium aponinum
<220> FEATURE:
<221> NAME/KEY: Xaa 1
<222> LOCATION: (1)..(1)
<223> OTHER INFORMATION: Gly/Thr
<220> FEATURE:
<221> NAME/KEY: Xaa 7 and 8
<222> LOCATION: (7)..(8)
<223> OTHER INFORMATION: Thr/Ala

<400> SEQUENCE: 1

Xaa Thr Thr Ala Cys Ala Xaa Xaa
1               5

<210> SEQ ID NO 2
<211> LENGTH: 126
<212> TYPE: PRT
<213> ORGANISM: Artificial sequence
<220> FEATURE:
<223> OTHER INFORMATION: N-RpaB
```

<400> SEQUENCE: 2

```
Met Glu Asn Arg Lys Glu Lys Ile Leu Val Val Asp Asp Glu Ala Ser
1               5                   10                  15

Ile Arg Arg Ile Leu Glu Thr Arg Leu Ala Met Ile Gly Tyr Glu Val
            20                  25                  30

Val Thr Ala Ala Asp Gly Glu Ala Leu Ile Thr Phe Arg Asn Ala
        35                  40                  45

Thr Pro Asp Leu Val Val Leu Asp Val Met Met Pro Lys Leu Asp Gly
    50                  55                  60

Tyr Gly Val Cys Gln Glu Leu Arg Lys Glu Ser Asp Val Pro Ile Ile
65              70                  75                  80

Met Leu Thr Ala Leu Gly Asp Val Ala Asp Arg Ile Thr Gly Leu Glu
                85                  90                  95

Leu Gly Ala Asp Asp Tyr Val Val Lys Pro Phe Ser Pro Lys Glu Leu
            100                 105                 110

Glu Ala Arg Ile Arg Ser Val Leu Arg Arg Val Glu Lys Ser
            115                 120                 125
```

<210> SEQ ID NO 3
<211> LENGTH: 327
<212> TYPE: DNA
<213> ORGANISM: Cyanobacterium aponinum

<400> SEQUENCE: 3

```
tgagaaaaag tgtaaacaaa tattaagaaa aagatcagaa aaatttaaca acacgtaata    60
aaaaaatgcg tcactacggg ttataaattt acatgaaagg ttaaaacact tttctgagac   120
gattttgata aaaagttgt caaaaaatta gtttctttta caaatgctta acaaaaactt   180
ggttttaagc acaaaataag agagactaat ttgcagaagt tttacaagga aatcttgaag   240
aaaaagatct aagtaaaacg actctgttta accaaaattt aacaaattta acaaaacaaa   300
ctaaatctat taggagatta actaagc                                       327
```

<210> SEQ ID NO 4
<211> LENGTH: 409
<212> TYPE: DNA
<213> ORGANISM: Cyanobacterium aponinum

<400> SEQUENCE: 4

```
cttgaaaaag ttgaggtatt aatagagctt gataaatgat aataaaaaca gatttagctc    60
ttattttaag ggaaaaagaa ataaataaaa tattagtaaa tatcaaaaat atcagccttt   120
caaaaataat ttgactcttt tcaaaaaaaa atgttatctt taaggtatgc tttaaacctt   180
aaatacttct attggtaaca ctgttctcaa tcttatttca gattttccca ttgagcataa   240
ataaaatatt aagcagaagt agaaaaggtt gatattagca ataataaaaa ttaacaataa   300
aatgtgaaaa cagattacta ctgattattt attgccatga gctaattagt aataatttgt   360
ctttttttgat cgaaaaatga aatttttttaa gcggaggaac tgaaaatta              409
```

<210> SEQ ID NO 5
<211> LENGTH: 205
<212> TYPE: DNA
<213> ORGANISM: Cyanobacterium aponinum

<400> SEQUENCE: 5

```
tagagtatga taaatgaca aggaaaggat tatttctct tgtttaaatt ctcaagattc     60
ttatgcttat ttatttatg taagtgtctc ttttccttga aatagaaaga aaaaagtggc   120
```

```
taattttgag aaaagctaac aacgctttgg ttaactaaaa atcaaaagtg agattactga    180
tcgcttaaga aatggagtat tgatt                                         205

<210> SEQ ID NO 6
<211> LENGTH: 338
<212> TYPE: DNA
<213> ORGANISM: Cyanobacterium aponinum

<400> SEQUENCE: 6
gcagttagat aaataagtaa tgagcgggag aaatagggc aaatggccat tcgccctac     60 agggaggtgg caggtgttag ggtgtttagg ggatgaggtg atgagggtag agggagataa   120
ggtgtcgggt ttcagatttc aggttttaga agaaagtaac gagtaattat caactattca   180
ctattcacta ttgcctgttg cccttctctc cttgaaatat aaaaaaatgt aaaaatatca   240
ttaagaaaag taacaaaata aacagaaagg ttgacaaagt tgacgcttta atatccgtat   300
gttagcttta taacaacgaa atcaacggag gagtgaaa                           338

<210> SEQ ID NO 7
<211> LENGTH: 411
<212> TYPE: DNA
<213> ORGANISM: Cyanobacterium aponinum

<400> SEQUENCE: 7
tatttatata taaactcgaa taaaattatc aatataaagt caaactatat ctatcctatt    60
ttaactgcta ttggtaagtc ccttaattag tgttggggtg aatagatttt aaaagggcaa   120
accccccttt atcctccctc gagaggggg agggcaaaag gcaaggggca agggaaaaat    180
taagaattaa gaattaaaaa ctccgaacac ctgtaggggc gaatagccat tcgcttcccc   240 tcatccccc atctcccaa caccctaagc ccctactcgt tactcattta tttacatcat     300
ttatttacat cattaagaaa agtaacaaat tttgacaagt agtctttga caggaaaaag    360 caaattctcg aagatgaaaa caatagaaaa aaattcaatc ttacagtaac g            411

<210> SEQ ID NO 8
<211> LENGTH: 214
<212> TYPE: DNA
<213> ORGANISM: Cyanobacterium aponinum

<400> SEQUENCE: 8
agagttatat ttacatagtg tgtgcgagta agggcaactt ttgtaggtag atgaataaac    60
ctcaaattac tcatcttaaa agacgatatt tttaatctat tcttctgtaa taaaatactt   120
ctttcgatag agatatttaa tacttttgag agatgaaaat aatttcaata attgtcatga   180
tagagagtaa gtgcaaataa gaaaaaattg attt                               214

<210> SEQ ID NO 9
<211> LENGTH: 211
<212> TYPE: DNA
<213> ORGANISM: Cyanobacterium aponinum

<400> SEQUENCE: 9
gtgatatttg gtttattcta tattttcctt aagtaaaaat tcagtcatga gggaaacttt    60
tgttaaaatt tgctttaaat taataggaag atcattaaga aaatcttaaa aagattgagt   120
ttttagatcg aaattattga agaaaaatta acaggggttc tgctcaaaat tttattaaat   180
tactctactg tagtaaagga gaaattttat t                                  211
```

<210> SEQ ID NO 10
<211> LENGTH: 380
<212> TYPE: DNA
<213> ORGANISM: Cyanobacterium aponinum

<400> SEQUENCE: 10

```
ataaccaatg ggacttgaat tttagatcca tttatttaat tctattttg ttacatttct      60 ttatattaat cagaattatg ttactttgtt ttgttttatg tcgttacctt attgaagaaa     120
gagtggatga gaaggtaaat gacggggcat aaatatcgat tcgttgtcag aataagctgt    180
tttattcact taactggttg tttgccaatt tctccctaat tcccataact tgtataacta     240
aatttaataa tcaatttag taaattaaga ataggtaaa agtagtattt agaattaagt       300
taactttaat aaatttcctg tattttttta tagaaaaaag tataaaataa aaacatatca    360
aaaaagtttg aaatgacaat                                                  380
```

<210> SEQ ID NO 11
<211> LENGTH: 542
<212> TYPE: DNA
<213> ORGANISM: Cyanobacterium aponinum

<400> SEQUENCE: 11

```
gaatagttga taattactcg ttactcatta ctcacttaaa cctgccacct gatacctgcc      60
acctctcccc ccatcacctc atcccctcaa cattccgaac cccttgacac ttgaactaa     120 aattgtatta aagtgcaaat ctggacgggg ttaaccagtg tgacttataa tagtaaacgc    180
tgttttttat aataaataag ctaaatattt aaaaactatg agtaaatata cactaaatgg    240
tactagacgt aagcagaaaa gaacctccgg tttccgcgcc cgtatgagaa ccaaaaatgg    300
tagaaaagta attcaagctc gtcgtaataa gggtagaaaa agattagcag tataaaatta    360
ctgttaaata aggaagctaa gtttagcatt ttaagtttga tattactaat cattaaattt    420
actgtgaaat ataggtggga ctaccatcaa agcatcgact gaaacggcgt ttaaatttcc    480
aatctgttta tcaacagggt attcgccgct ctagtcgtta ttttattgtc cgagggttac    540
gg                                                                     542
```

<210> SEQ ID NO 12
<211> LENGTH: 70
<212> TYPE: DNA
<213> ORGANISM: Cyanobacterium aponinum
<220> FEATURE:
<221> NAME/KEY: n1
<222> LOCATION: (1)..(1)
<223> OTHER INFORMATION: Region 116 bp long, wherein each nucleotide is
    independently selected from: a, t, c and g
<220> FEATURE:
<221> NAME/KEY: n17
<222> LOCATION: (17)..(17)
<223> OTHER INFORMATION: Region 7 bp long, wherein each nucleotide is
    independently selected from: a, t, c and g
<220> FEATURE:
<221> NAME/KEY: n33
<222> LOCATION: (33)..(33)
<223> OTHER INFORMATION: Region 15 bp long, wherein each nucleotide is
    independently selected from: a, t, c and g
<220> FEATURE:
<221> NAME/KEY: n48
<222> LOCATION: (48)..(48)
<223> OTHER INFORMATION: Region 22 bp long, wherein each nucleotide is
    independently selected from: a, t, c and g
<220> FEATURE:
<221> NAME/KEY: n55
<222> LOCATION: (55)..(55)
<223> OTHER INFORMATION: Region 55 bp long, wherein each nucleotide is

```
       independently selected from: a, t, c and g
<220> FEATURE:
<221> NAME/KEY: n67
<222> LOCATION: (67)..(67)
<223> OTHER INFORMATION: Region 2 bp long, wherein each nucleotide is
      independently selected from: a, t, c and g

<400> SEQUENCE: 12
natgcaaaaa acgaatnatg tgtaaaaaga aangtagtca aagttacnta atgtnccgag      60 gacaaanatg                                                            70

<210> SEQ ID NO 13
<211> LENGTH: 71
<212> TYPE: DNA
<213> ORGANISM: Artificial sequence
<220> FEATURE:
<223> OTHER INFORMATION: Generalized PnirA sequence with nucleotide
      changes in the RBS
<220> FEATURE:
<221> NAME/KEY: n1
<222> LOCATION: (1)..(1)
<223> OTHER INFORMATION: Region 116 bp long, wherein each nucleotide is
      independently selected from: a, t, c and g
<220> FEATURE:
<221> NAME/KEY: n17
<222> LOCATION: (17)..(17)
<223> OTHER INFORMATION: Region 7 bp long, wherein each nucleotide is
      independently selected from: a, t, c and g
<220> FEATURE:
<221> NAME/KEY: n33
<222> LOCATION: (33)..(33)
<223> OTHER INFORMATION: Region 15 bp long, wherein each nucleotide is
      independently selected from: a, t, c and g
<220> FEATURE:
<221> NAME/KEY: n48
<222> LOCATION: (48)..(48)
<223> OTHER INFORMATION: Region 22 bp long, wherein each nucleotide is
      independently selected from: a, t, c and g
<220> FEATURE:
<221> NAME/KEY: n55
<222> LOCATION: (55)..(55)
<223> OTHER INFORMATION: Region 55 bp long, wherein each nucleotide is
      independently selected from: a, t, c and g
<220> FEATURE:
<221> NAME/KEY: n68
<222> LOCATION: (68)..(68)
<223> OTHER INFORMATION: Region 2 bp long, wherein each nucleotide is
      independently selected from: a, t, c and g

<400> SEQUENCE: 13
natgcaaaaa acgaatnatg tgtaaaaaga aangtagtca aagttacnta atgtnggagg      60
atcagccnat g                                                          71

<210> SEQ ID NO 14
<211> LENGTH: 70
<212> TYPE: DNA
<213> ORGANISM: Artificial sequence
<220> FEATURE:
<223> OTHER INFORMATION: Generalized PnirA sequence a nucleotide changes
      in the operator region and the TATA box
<220> FEATURE:
<221> NAME/KEY: n1
<222> LOCATION: (1)..(1)
<223> OTHER INFORMATION: Region 116 bp long, wherein each nucleotide is
      independently selected from: a, t, c and g
<220> FEATURE:
<221> NAME/KEY: n17
<222> LOCATION: (17)..(17)
<223> OTHER INFORMATION: Region 7 bp long, wherein each nucleotide is
      independently selected from: a, t, c and g
<220> FEATURE:
<221> NAME/KEY: n33
<222> LOCATION: (33)..(33)
```

```
<223> OTHER INFORMATION: Region 15 bp long, wherein each nucleotide is
      independently selected from: a, t, c and g
<220> FEATURE:
<221> NAME/KEY: n48
<222> LOCATION: (48)..(48)
<223> OTHER INFORMATION: Region 22 bp long, wherein each nucleotide is
      independently selected from: a, t, c and g
<220> FEATURE:
<221> NAME/KEY: n55
<222> LOCATION: (55)..(55)
<223> OTHER INFORMATION: Region 55 bp long, wherein each nucleotide is
      independently selected from: a, t, c and g
<220> FEATURE:
<221> NAME/KEY: n67
<222> LOCATION: (67)..(67)
<223> OTHER INFORMATION: Region 2 bp long, wherein each nucleotide is
      independently selected from: a, t, c and g

<400> SEQUENCE: 14
natgcaaaaa acgcatnatg cgtaaaaagc atngtaatca aagttacnta atatnccgag      60 gacaaanatg                                                            70

<210> SEQ ID NO 15
<211> LENGTH: 70
<212> TYPE: DNA
<213> ORGANISM: Artificial sequence
<220> FEATURE:
<223> OTHER INFORMATION: Generalized PnirA sequence with nucleotide
      changes in the RBS, the operator region and the TATA box
<220> FEATURE:
<221> NAME/KEY: n1
<222> LOCATION: (1)..(1)
<223> OTHER INFORMATION: Region 116 bp long, wherein each nucleotide is
      independently selected from: a, t, c and g
<220> FEATURE:
<221> NAME/KEY: n17
<222> LOCATION: (17)..(17)
<223> OTHER INFORMATION: Region 7 bp long, wherein each nucleotide is
      independently selected from: a, t, c and g
<220> FEATURE:
<221> NAME/KEY: n33
<222> LOCATION: (33)..(33)
<223> OTHER INFORMATION: Region 15 bp long, wherein each nucleotide is
      independently selected from: a, t, c and g
<220> FEATURE:
<221> NAME/KEY: n48
<222> LOCATION: (48)..(48)
<223> OTHER INFORMATION: Region 22 bp long, wherein each nucleotide is
      independently selected from: a, t, c and g
<220> FEATURE:
<221> NAME/KEY: n55
<222> LOCATION: (55)..(55)
<223> OTHER INFORMATION: Region 22 bp long, wherein each nucleotide is
      independently selected from: a, t, c and g
<220> FEATURE:
<221> NAME/KEY: n67
<222> LOCATION: (67)..(67)
<223> OTHER INFORMATION: Region 2 bp long, wherein each nucleotide is
      independently selected from: a, t, c and g

<400> SEQUENCE: 15
natgcaaaaa acgcatnatg cgtaaaaagc atngtaatca aagttacnta atatnccgag      60 gacaaanatg                                                            70

<210> SEQ ID NO 16
<211> LENGTH: 67
<212> TYPE: DNA
<213> ORGANISM: Cyanobacterium aponinum
<220> FEATURE:
<221> NAME/KEY: n4
<222> LOCATION: (4)..(4)
<223> OTHER INFORMATION: Region 7 bp long, wherein each nucleotide is
      independently selected from: a, t, c and g
```

<220> FEATURE:
<221> NAME/KEY: n51
<222> LOCATION: (51)..(51)
<223> OTHER INFORMATION: Region 15 bp long, wherein each nucleotide is
      independently selected from: a, t, c and g

<400> SEQUENCE: 16
catngtttac tcaaaacctt gacattgaca ctaatgttaa ggtttaggct ncaagttaaa      60
aagcatg      67

<210> SEQ ID NO 17
<211> LENGTH: 67
<212> TYPE: DNA
<213> ORGANISM: Artificial sequence
<220> FEATURE:
<223> OTHER INFORMATION: Modified variant of PcorT includes changes in
      the RBS
<220> FEATURE:
<221> NAME/KEY: n4
<222> LOCATION: (4)..(4)
<223> OTHER INFORMATION: Region 7 bp long, wherein each nucleotide is
      independently selected from: a, t, c and g
<220> FEATURE:
<221> NAME/KEY: n51
<222> LOCATION: (51)..(51)
<223> OTHER INFORMATION: Region 15 bp long, wherein each nucleotide is
      independently selected from: a, t, c and g

<400> SEQUENCE: 17
catngtttac tcaaaacctt gacattgaca ctaatgttaa ggtttaggct ngaggataaa      60
aagcatg      67

<210> SEQ ID NO 18
<211> LENGTH: 65
<212> TYPE: DNA
<213> ORGANISM: Artificial sequence
<220> FEATURE:
<223> OTHER INFORMATION: Modified variant of PcorT includes changes in
      the TATA box
<220> FEATURE:
<221> NAME/KEY: n4
<222> LOCATION: (4)..(4)
<223> OTHER INFORMATION: Region 7 bp long, wherein each nucleotide is
      independently selected from: a, t, c and g
<220> FEATURE:
<221> NAME/KEY: n49
<222> LOCATION: (49)..(49)
<223> OTHER INFORMATION: Region 15 bp long, wherein each nucleotide is
      independently selected from: a, t, c and g

<400> SEQUENCE: 18
catngtttac tcaaaacctt gacattgact aatgttaagg tttagaatnc aagttaaaaa      60
gcatg      65

<210> SEQ ID NO 19
<211> LENGTH: 67
<212> TYPE: DNA
<213> ORGANISM: Artificial sequence
<220> FEATURE:
<223> OTHER INFORMATION: Modified variant of PcorT includes changes in
      the RBS and the TATA box
<220> FEATURE:
<221> NAME/KEY: n4
<222> LOCATION: (4)..(4)
<223> OTHER INFORMATION: Region 7 bp long, wherein each nucleotide is
      independently selected from: a, t, c and g
<220> FEATURE:
<221> NAME/KEY: n51
<222> LOCATION: (51)..(51)
<223> OTHER INFORMATION: Region 15 bp long, wherein each nucleotide is independently selected from: a, t, c and g

<400> SEQUENCE: 19
catngtttac tcaaaacctt gacattgaca ctaatgttaa ggtttagaat ngaggataaa    60
aaccatg                                                              67

<210> SEQ ID NO 20
<211> LENGTH: 69
<212> TYPE: DNA
<213> ORGANISM: Synechococcus elongatus
<220> FEATURE:
<221> NAME/KEY: n1
<222> LOCATION: (1)..(1)
<223> OTHER INFORMATION: Region 8 bp long, wherein each nucleotide is
      independently selected from: a, t, c and g
<220> FEATURE:
<221> NAME/KEY: n28
<222> LOCATION: (28)..(28)
<223> OTHER INFORMATION: Region 4 bp long, wherein each nucleotide is
      independently selected from: a, t, c and g
<220> FEATURE:
<221> NAME/KEY: n59
<222> LOCATION: (59)..(59)
<223> OTHER INFORMATION: Region 12 bp long, wherein each nucleotide is
      independently selected from: a, t, c and g
<220> FEATURE:
<221> NAME/KEY: n66
<222> LOCATION: (66)..(66)
<223> OTHER INFORMATION: Region 7 bp long, wherein each nucleotide is
      independently selected from: a, t, c and g

<400> SEQUENCE: 20
naatacctga ataattgttc atgtgttnta aaaatgtgaa caatcgttca actatttang    60 gaggtnatg                                                            69

<210> SEQ ID NO 21
<211> LENGTH: 74
<212> TYPE: DNA
<213> ORGANISM: Artificial sequence
<220> FEATURE:
<223> OTHER INFORMATION: Zn2+-inducible PsmtA with changes in the RBS
<220> FEATURE:
<221> NAME/KEY: n1
<222> LOCATION: (1)..(1)
<223> OTHER INFORMATION: Region 8 bp long, wherein each nucleotide is
      independently selected from: a, t, c and g
<220> FEATURE:
<221> NAME/KEY: n28
<222> LOCATION: (28)..(28)
<223> OTHER INFORMATION: Region 4 bp long, wherein each nucleotide is
      independently selected from: a, t, c and g
<220> FEATURE:
<221> NAME/KEY: n59
<222> LOCATION: (59)..(59)
<223> OTHER INFORMATION: Region 10 bp long, wherein each nucleotide is
      independently selected from: a, t, c and g
<220> FEATURE:
<221> NAME/KEY: n71
<222> LOCATION: (71)..(71)
<223> OTHER INFORMATION: Region 4 bp long, wherein each nucleotide is
      independently selected from: a, t, c and g

<400> SEQUENCE: 21
naatacctga ataattgttc atgtgttnta aaaatgtgaa caatcgttca actatttana    60
aggaggtgat natg                                                      74

<210> SEQ ID NO 22
<211> LENGTH: 73
<212> TYPE: DNA
<213> ORGANISM: Artificial sequence

```
<220> FEATURE:
<223> OTHER INFORMATION: Zn2+-inducible PsmtA with changes in the RBS
<220> FEATURE:
<221> NAME/KEY: n1
<222> LOCATION: (1)..(1)
<223> OTHER INFORMATION: Region 8 bp long, wherein each nucleotide is
      independently selected from: a, t, c and g
<220> FEATURE:
<221> NAME/KEY: n28
<222> LOCATION: (28)..(28)
<223> OTHER INFORMATION: Region 4 bp long, wherein each nucleotide is
      independently selected from: a, t, c and g
<220> FEATURE:
<221> NAME/KEY: n59
<222> LOCATION: (59)..(59)
<223> OTHER INFORMATION: Region 10 bp long, wherein each nucleotide is
      independently selected from: a, t, c and g
<220> FEATURE:
<221> NAME/KEY: n70
<222> LOCATION: (70)..(70)
<223> OTHER INFORMATION: Region 5 bp long, wherein each nucleotide is
      independently selected from: a, t, c and g

<400> SEQUENCE: 22
naatacctga ataattgttc atgtgttnta aaaatgtgaa caatcgttca actatttana      60
aggaggtatn atg                                                        73

<210> SEQ ID NO 23
<211> LENGTH: 381
<212> TYPE: DNA
<213> ORGANISM: Artificial sequence
<220> FEATURE:
<223> OTHER INFORMATION: N-RpaB Gene Sequence

<400> SEQUENCE: 23
atggaaaatc gcaaggaaaa aatcctcgtt gtcgacgatg aagcgagcat ccggcggatt      60
cttgaaactc ggttggcgat gattggttac gaagttgtca ccgcagccga cggcgaagaa     120
gccctcatca ccttccgcaa tgctacgccg atctcgtgg tgctcgatgt gatgatgccc      180
aagctcgatg gctatggcgt tgccaagag ctgcgcaaag agtcggacgt tccgatcatc      240
atgctgacag ccttgggcga tgtggccgat cgcattacgg gcttgagtt gggagctgat      300 gactacgtcg tcaaaccctt ctcgcctaag gaactagaag cgcgaatccg ctcggtgctg     360
cgtcgggtcg aaaaaagcta g                                               381

<210> SEQ ID NO 24
<211> LENGTH: 244
<212> TYPE: PRT
<213> ORGANISM: Synechococcus elongatus

<400> SEQUENCE: 24

Met Glu Asn Arg Lys Glu Lys Ile Leu Val Val Asp Asp Glu Ala Ser
1               5                   10                  15

Ile Arg Arg Ile Leu Glu Thr Arg Leu Ala Met Ile Gly Tyr Glu Val
            20                  25                  30

Val Thr Ala Ala Asp Gly Glu Glu Ala Leu Ile Thr Phe Arg Asn Ala
        35                  40                  45

Thr Pro Asp Leu Val Val Leu Asp Val Met Met Pro Lys Leu Asp Gly
    50                  55                  60

Tyr Gly Val Cys Gln Glu Leu Arg Lys Glu Ser Asp Val Pro Ile Ile
65                  70                  75                  80

Met Leu Thr Ala Leu Gly Asp Val Ala Asp Arg Ile Thr Gly Leu Glu
                85                  90                  95
```

Leu Gly Ala Asp Asp Tyr Val Val Lys Pro Phe Ser Pro Lys Glu Leu
            100                 105                 110

Glu Ala Arg Ile Arg Ser Val Leu Arg Arg Val Glu Lys Ser Gly Ala
        115                 120                 125

Asn Gly Ile Pro Ser Ser Gly Val Ile Gln Ile Asn Ser Ile Arg Ile
    130                 135                 140

Asp Thr Asn Lys Arg Gln Val Tyr Lys Gly Asp Glu Arg Ile Arg Leu
145                 150                 155                 160

Thr Gly Met Glu Phe Ser Leu Leu Glu Leu Leu Val Ser Arg Ser Gly
                165                 170                 175

Glu Pro Phe Ser Arg Ala Glu Ile Leu Gln Glu Val Trp Gly Tyr Thr
            180                 185                 190

Pro Glu Arg His Val Asp Thr Arg Val Val Asp Val His Ile Ser Arg
        195                 200                 205

Leu Arg Ala Lys Leu Glu Asp Asp Pro Gly Asn Pro Glu Leu Ile Leu
    210                 215                 220

Thr Ala Arg Gly Thr Gly Tyr Leu Phe Gln Arg Ile Val Glu Pro Gly
225                 230                 235                 240

Glu Glu Gly Arg

<210> SEQ ID NO 25
<211> LENGTH: 735
<212> TYPE: DNA
<213> ORGANISM: Synechococcus elongatus

<400> SEQUENCE: 25
ttggaaaatc gcaaggaaaa aatcctcgtt gtcgacgatg aagcgagcat ccggcggatt        60
cttgaaactc ggttggcgat gattggttac gaagttgtca ccgcagccga cggcgaagaa       120
gccctcatca ccttccgcaa tgctacgccg gatctcgtgg tgctcgatgt gatgatgccc       180
aagctcgatg gctatggcgt ttgccaagag ctgcgcaaag agtcggacgt tccgatcatc       240
atgctgacag ccttgggcga tgtggccgat cgcattacgg ggcttgagtt gggagctgat       300
gactacgtcg tcaaacccct tctcgcctaa gaactagaag cgcgaatccg ctcggtgctg       360
cgtcgggtcg aaaaaagcgg tgctaatggc atccccagtt cgggcgtcat ccagatcaac       420
agcatccgca tcgacaccaa taagcgccaa gtctacaaag gcgatgagcg catccgtctg       480
acgggcatgg agttcagttt gttggaactg ctggtcagcc gctccggtga acctttagc        540 cgcgccgaaa tcctgcaaga ggtctggggc tatacccccg agcgccacgt cgatacccgc       600
gtagtcgatg tccacatctc gcggctgcgc gccaaattgg aagacgatcc gggcaaccct       660
gagctcattc tgacggcccg aggaaccggc tacctcttcc aacgcatcgt tgaaccgggc       720
gaagaagggc gttag                                                        735

<210> SEQ ID NO 26
<211> LENGTH: 248
<212> TYPE: PRT
<213> ORGANISM: Synechococcus elongatus

<400> SEQUENCE: 26

Met Thr Ala Thr Thr Pro Ser Lys Glu Thr Ile Leu Val Val Asp Asp
1               5                   10                  15

Glu Ala Ser Ile Arg Arg Ile Leu Glu Thr Arg Leu Ser Met Ile Gly
            20                  25                  30

Tyr Asn Val Val Thr Ala Cys Asp Gly Thr Glu Ala Leu Glu Leu Phe
        35                  40                  45

Glu Asn Thr Ala Pro Asp Leu Val Val Leu Asp Val Met Met Pro Lys
            50                  55                  60

Leu Asp Gly Tyr Gly Val Cys Gln Glu Leu Arg Lys Glu Ser Asp Val
 65                  70                  75                  80

Pro Ile Val Met Leu Thr Ala Leu Gly Asp Val Ala Asp Arg Ile Thr
                85                  90                  95

Gly Leu Glu Leu Gly Ala Asp Asp Tyr Val Val Lys Pro Phe Ser Pro
                100                 105                 110

Lys Glu Leu Glu Ala Arg Ile Arg Cys Val Leu Arg Arg Val Glu Lys
            115                 120                 125

Glu Ser Val Ala Gly Ile Pro Asn Ser Gly Val Ile Gln Val Ser Asp
130                 135                 140

Leu Arg Ile Asp Thr Asn Lys Arg Gln Val Phe Arg Ala Asp Glu Arg
145                 150                 155                 160

Ile Arg Leu Thr Gly Met Glu Phe Ser Leu Leu Glu Leu Leu Val Ser
                165                 170                 175

Arg Ser Gly Glu Pro Phe Asn Arg Gly Glu Ile Leu Lys Glu Val Trp
                180                 185                 190

Gly Tyr Thr Pro Glu Arg His Val Asp Thr Arg Val Val Asp Val His
                195                 200                 205

Ile Ser Arg Leu Arg Ser Lys Leu Glu Asp Asp Pro Ala Asn Pro Glu
210                 215                 220

Leu Ile Leu Thr Ala Arg Gly Thr Gly Tyr Leu Phe Gln Arg Ile Ile
225                 230                 235                 240

Asp Ser Val Ala Ser Glu Gly Pro
                245

<210> SEQ ID NO 27
<211> LENGTH: 233
<212> TYPE: PRT
<213> ORGANISM: Tolypothrix Sp.

<400> SEQUENCE: 27

Met Val Asp Asp Glu Ala Ser Ile Arg Arg Ile Leu Glu Thr Arg Leu
 1               5                  10                  15

Ser Met Ile Gly Tyr Asp Val Val Thr Ala Gly Asp Gly Glu Glu Ala
                20                  25                  30

Leu Glu Thr Phe Arg Lys Ala Asp Pro Asp Leu Val Val Leu Asp Val
                35                  40                  45

Met Met Pro Lys Leu Asp Gly Tyr Gly Val Cys Gln Glu Leu Arg Lys
 50                  55                  60

Glu Ser Asp Val Pro Ile Ile Met Leu Thr Ala Leu Gly Asp Val Ala
 65                  70                  75                  80

Asp Arg Ile Thr Gly Leu Glu Leu Gly Ala Asp Asp Tyr Val Val Lys
                85                  90                  95

Pro Phe Ser Pro Lys Glu Leu Glu Ala Arg Ile Arg Ser Val Leu Arg
                100                 105                 110

Arg Val Asp Lys Thr Ser Ala Ser Gly Ile Pro Ser Ser Gly Val Ile
            115                 120                 125

His Val Ala Asn Ile Lys Ile Asp Thr Asn Lys Arg Gln Val Tyr Lys
130                 135                 140

Gly Asp Glu Arg Ile Arg Leu Thr Gly Met Glu Phe Ser Leu Leu Glu
145                 150                 155                 160

Leu Leu Val Ser Arg Ser Gly Glu Ala Phe Ser Arg Ser Glu Ile Leu

```
                            165                 170                 175
Gln Glu Val Trp Gly Tyr Thr Pro Glu Arg His Val Asp Thr Arg Val
                180                 185                 190

Val Asp Val His Ile Ser Arg Leu Arg Ala Lys Leu Glu Asp Asp Pro
            195                 200                 205

Ser Asn Pro Glu Leu Ile Leu Thr Ala Arg Gly Thr Gly Tyr Leu Phe
        210                 215                 220

Gln Arg Ile Ile Glu Pro Gly Glu Glu
225                 230

<210> SEQ ID NO 28
<211> LENGTH: 247
<212> TYPE: PRT
<213> ORGANISM: Thermosynechococcus elongatus

<400> SEQUENCE: 28

Met Glu Thr His Lys Glu Lys Ile Leu Val Val Asp Asp Glu Ala Ser
1               5                   10                  15

Ile Arg Arg Ile Leu Glu Thr Arg Leu Ser Met Ile Gly Tyr Thr Val
                20                  25                  30

Val Thr Ala Ala Asp Gly Glu Glu Ala Leu Thr Thr Phe Arg Gln Glu
            35                  40                  45

Gln Pro Asp Leu Val Val Leu Asp Val Met Met Pro Lys Leu Asp Gly
        50                  55                  60

Tyr Gly Val Cys Gln Glu Leu Arg Lys Glu Ser Asp Val Pro Ile Ile
65                  70                  75                  80

Met Leu Thr Ala Leu Gly Asp Val Ala Asp Arg Ile Thr Gly Leu Glu
                85                  90                  95

Leu Gly Ala Asp Asp Tyr Val Val Lys Pro Phe Ser Pro Lys Glu Leu
            100                 105                 110

Glu Ala Arg Ile Arg Ser Val Leu Arg Arg Ile Glu Lys Thr Asn Thr
        115                 120                 125

Ser Gly Ile Pro Ser Ser Gly Val Ile Gln Val Gly Asn Ile Arg Ile
    130                 135                 140

Asp Thr Asn Lys Arg Gln Val Tyr Lys Gly Asp Glu Arg Ile Arg Leu
145                 150                 155                 160

Thr Gly Met Glu Phe Met Leu Leu Glu Leu Leu Val Gly Arg Ser Gly
                165                 170                 175

Glu Pro Phe Ser Arg Ala Glu Ile Leu Glu Gln Val Trp Gly Tyr Thr
            180                 185                 190

Pro Glu Arg His Val Asp Thr Arg Val Val Asp Val His Ile Ser Arg
        195                 200                 205

Leu Arg Ala Lys Leu Glu Glu Asp Pro Ser Asn Pro Glu Leu Ile Leu
    210                 215                 220

Thr Ala Arg Gly Thr Gly Tyr Leu Phe Gln Arg Ile Thr Glu Pro Gly
225                 230                 235                 240

Glu Ala Ser Asn Lys Asn Gln
                245

<210> SEQ ID NO 29
<211> LENGTH: 243
<212> TYPE: PRT
<213> ORGANISM: Arthrospira platensis

<400> SEQUENCE: 29

Met Glu Asn His Lys Glu Arg Ile Leu Val Val Asp Asp Glu Ala Ser
```

```
              1               5              10              15
            Ile Arg Arg Ile Leu Glu Thr Arg Leu Ser Met Ile Gly Tyr Asp Val
                             20                  25                  30

Val Thr Ala Ala Asp Gly Glu Glu Ala Leu Glu Thr Phe Arg Leu Thr
                             35                  40                  45

Glu Pro Asp Leu Val Val Leu Asp Val Met Met Pro Lys Leu Asp Gly
                             50                  55                  60

Tyr Gly Val Cys Gln Glu Leu Arg Lys Glu Ser Asp Ile Pro Ile Ile
             65                  70                  75                  80

Met Leu Thr Ala Leu Gly Asp Val Ala Asp Arg Ile Thr Gly Leu Glu
                             85                  90                  95

Leu Gly Ala Asp Asp Tyr Val Val Lys Pro Phe Ser Pro Lys Glu Leu
                            100                 105                 110

Glu Ala Arg Ile Arg Ser Val Leu Arg Arg Ile Asp Lys Asn Gly Ala
                            115                 120                 125

Ser Gly Ile Pro Ser Ser Gly Val Ile Gln Ile Ala Ser Ile Arg Ile
                            130                 135                 140

Asp Thr Asn Lys Arg Gln Val Tyr Lys Gly Asp Glu Arg Ile Arg Leu
            145                 150                 155                 160

Thr Gly Met Glu Phe Ser Leu Leu Glu Leu Leu Val Ser Arg Ser Gly
                            165                 170                 175

Glu Pro Phe Ser Arg Ser Glu Ile Leu Gln Glu Val Trp Gly Tyr Thr
                            180                 185                 190

Pro Glu Arg His Val Asp Thr Arg Val Val Asp Val His Ile Ser Arg
                            195                 200                 205

Leu Arg Ala Lys Leu Glu Asp Asp Pro Ser Asn Pro Glu Leu Ile Leu
                            210                 215                 220

Thr Ala Arg Gly Thr Gly Tyr Leu Phe Gln Arg Ile Ile Asp Pro Ser
            225                 230                 235                 240

Glu Val Gly

<210> SEQ ID NO 30
<211> LENGTH: 732
<212> TYPE: DNA
<213> ORGANISM: Arthrospira platensis

<400> SEQUENCE: 30
ttggaaaacc ataaggaaag aatttttagtt gtcgatgacg aggccagtat ccgccggatt      60
ttggaaactc gcctttccat gatcggttac gatgtagtaa ctgccgccga cggggaggag     120
gctttagaaa ccttccgcct gacagaacct gacctcgtgg ttttggatgt gatgatgcct     180
aaactagatg gctacggagt ttgtcaggaa ttaaggaagg agtctgacat ccccattatt     240
atgctcaccg ccttggggga tgtcgccgat cgcatcaccg ggttagaatt aggcgctgat     300
gattatgtcg tcaaacccct tcacccaag gaactagagg cccgtatccg ttccgtcctg     360
cgccgcattg ataaaaatgg cgcttctgga attcccagtt ctggagttat ccaaattgcc     420
agtattagga ttgacaccaa caagcgacag gtttacaaag gtgatgaacg catccgctta     480
accgggatgg agtttagcct attgaactc ttggtcagtc ggtcaggaga acccttttcc     540
cgatccgaaa ttctccagga agtttgggga tatactcccg aacgccatgt tgatactcgc     600
gtcgtcgatg tgcatatttc ccggctcaga gctaagttag aagatgatcc tagcaaccca     660
gaactgattt tgaccgctcg cggtactggc tatttattcc agcgcattat tgatccttca     720
gaagtggggt ga                                                         732
```

<210> SEQ ID NO 31
<211> LENGTH: 244
<212> TYPE: PRT
<213> ORGANISM: Cyanobacterium aponinum

<400> SEQUENCE: 31

Met Glu Thr Gln Lys Glu Lys Ile Leu Val Val Asp Asp Glu Ala Ser
1               5                   10                  15

Ile Arg Arg Ile Leu Glu Thr Arg Leu Ser Met Ile Gly Tyr Asp Val
            20                  25                  30

Val Thr Ala Ala Asp Gly Glu Asp Ala Ile Ala Thr Phe His Glu Thr
        35                  40                  45

Gln Pro Asp Leu Val Val Leu Asp Val Met Met Pro Lys Leu Asp Gly
    50                  55                  60

Tyr Gly Val Cys Gln Glu Leu Arg Lys Glu Ser Asp Ile Pro Ile Ile
65                  70                  75                  80

Met Leu Thr Ala Leu Gly Asp Val Ala Asp Arg Ile Thr Gly Leu Glu
                85                  90                  95

Leu Gly Ala Asp Asp Tyr Val Val Lys Pro Phe Ser Pro Lys Glu Leu
            100                 105                 110

Glu Ala Arg Ile Arg Ser Val Leu Arg Arg Val Asp Lys Thr Gly Val
        115                 120                 125

Ala Gly Ile Pro Ser Ser Gly Val Ile Ser Ile Asn Ser Ile Arg Ile
    130                 135                 140

Asp Thr Asn Lys Arg Gln Val Tyr Lys Gly Asp Gln Arg Ile Arg Leu
145                 150                 155                 160

Thr Gly Met Glu Phe Ser Leu Leu Glu Leu Leu Val Ser Lys Ser Gly
                165                 170                 175

Glu Pro Phe Ser Arg Ser Glu Ile Leu Gln Glu Val Trp Gly Tyr Thr
            180                 185                 190

Pro Glu Arg His Val Asp Thr Arg Val Val Asp Val His Val Ser Arg
        195                 200                 205

Leu Arg Ala Lys Leu Glu Asp Asp Pro Ser Asn Pro Glu Leu Ile Leu
    210                 215                 220

Thr Ala Arg Gly Thr Gly Tyr Leu Phe Gln Arg Ile Leu Glu Pro Gly
225                 230                 235                 240

Glu Lys Lys Lys

<210> SEQ ID NO 32
<211> LENGTH: 735
<212> TYPE: DNA
<213> ORGANISM: Cyanobacterium aponinum

<400> SEQUENCE: 32
ttggaaactc aaaagagaa aattttagta gttgacgatg aagcaagtat tcgccgtatt      60
ttagaaactc gtctctcgat gattggttat gatgttgtca ctgccgctga tggagaagat     120
gcgatcgcaa cttttcatga aactcaacca gatttagtgg ttttagacgt aatgatgccc     180
aaattagacg gctatggagt ttgtcaagaa ctaagaaaag aatctgatat acccattatt     240
atgttaactg ctttaggaga tgtagcagat cgcattacag gtttagagct aggagcagat     300
gattatgtgg taaaaccttt ctctcccaaa gaattagaag caagaatccg ctctgtgtta     360
agaagagttg acaaaacagg agttgcagga atacctagtt cgggagttat ctccattaac     420
tctatcagaa ttgacaccaa caaaagacag gtttacaaag agatcaaag aatccgctta     480

```
acaggaatgg aatttagctt actagaactg cttgtaagta aatcaggaga acctttttct    540
cgctcagaaa tcttacagga ggtttgggga tatacacctg agcgtcatgt cgatactaga    600
gttgtggacg ttcacgtatc ccgtttaaga gcaaaattag aagatgaccc tagcaatcct    660
gaactgattt taaccgctag aggtacagga tatttgtttc aaaggatatt agaaccggga    720
gaaaagaaaa agtag                                                     735

<210> SEQ ID NO 33
<211> LENGTH: 402
<212> TYPE: DNA
<213> ORGANISM: Synechococcus elongatus

<400> SEQUENCE: 33
atgcgatcgc ttaaagctgt cgaagctccg agcctcaagg aaaaaatttt agtcgtagac     60
gacgaagctg cggtccgtcg cattttgact atgcgcctct cgatggctgg ctatcaggtg    120
gtggtcgcca gcgatggcca tgaagccttg gcgatgtttg agcaagaagc gcccgatttg    180
atcgtgttgg atgtgatgct acccaaactc gatggctacg gcgtttgccg tgagttgcgg    240
aagctctccg atgtaccaat catcatgctc tctgccctgg gggatatcgc cgatcgcatt    300
acagggctcg acttgggtgc tgacgactat ctgcccaagc ccttctctcc caaggaactg    360
gaagcgcgga tcgccacaat tctgcgccgg ctggatgact ct                       402

<210> SEQ ID NO 34
<211> LENGTH: 134
<212> TYPE: PRT
<213> ORGANISM: Synechococcus elongatus

<400> SEQUENCE: 34

Met Arg Ser Leu Lys Ala Val Glu Ala Pro Ser Leu Lys Glu Lys Ile
1               5                   10                  15

Leu Val Val Asp Asp Glu Ala Ala Val Arg Arg Ile Leu Thr Met Arg
            20                  25                  30

Leu Ser Met Ala Gly Tyr Gln Val Val Ala Ser Asp Gly His Glu
        35                  40                  45

Ala Leu Ala Met Phe Glu Gln Glu Ala Pro Asp Leu Ile Val Leu Asp
    50                  55                  60

Val Met Leu Pro Lys Leu Asp Gly Tyr Gly Val Cys Arg Glu Leu Arg
65                  70                  75                  80

Lys Leu Ser Asp Val Pro Ile Ile Met Leu Ser Ala Leu Gly Asp Ile
                85                  90                  95

Ala Asp Arg Ile Thr Gly Leu Asp Leu Gly Ala Asp Asp Tyr Leu Pro
            100                 105                 110

Lys Pro Phe Ser Pro Lys Glu Leu Glu Ala Arg Ile Ala Thr Ile Leu
        115                 120                 125

Arg Arg Leu Asp Asp Ser
    130

<210> SEQ ID NO 35
<211> LENGTH: 768
<212> TYPE: DNA
<213> ORGANISM: Synechococcus elongatus

<400> SEQUENCE: 35
atgcgatcgc ttaaagctgt cgaagctccg agcctcaagg aaaaaatttt agtcgtagac     60
gacgaagctg cggtccgtcg cattttgact atgcgcctct cgatggctgg ctatcaggtg    120
```

```
gtggtcgcca gcgatggcca tgaagccttg gcgatgtttg agcaagaagc gcccgatttg    180
atcgtgttgg atgtgatgct acccaaactc gatggctacg gcgtttgccg tgagttgcgg    240
aagctctccg atgtaccaat catcatgctc tctgccctgg gggatatcgc cgatcgcatt    300
acagggctcg acttgggtgc tgacgactat ctgcccaagc ccttctctcc caaggaactg    360
gaagcgcgga tcgccacaat tctgcgccgg ctggatgact ctcccaatgc gctatccgcc    420
ccttcctccc cagggggtgtt gcgcatcagt gatgtagaaa tcgataccaa ccgccgccaa    480
gtctttcagc ggggcgagcg ggttcccctg acttacaccg aattcagcct gctggaacta    540
ttgttccggc agcccggtcg ggtcgtaccg cgcgccgaaa tcttggaaga actctggggc    600
tatccgccgc ggcgcaatgc cgacctgcga gtcgtcgatg tctatgtcgc ccgtctgcga    660
tcaaagctcg aagccgaccc ccgcaatcct gagctgatca tcacagtccg cggaacaggc    720
tatacctccc agcgcctcaa agatttaccg gaagcggctg gagcctag                768
```

<210> SEQ ID NO 36
<211> LENGTH: 255
<212> TYPE: PRT
<213> ORGANISM: Synechococcus elongatus

<400> SEQUENCE: 36

```
Met Arg Ser Leu Lys Ala Val Glu Ala Pro Ser Leu Lys Glu Lys Ile
1               5                   10                  15

Leu Val Val Asp Asp Glu Ala Ala Val Arg Arg Ile Leu Thr Met Arg
            20                  25                  30

Leu Ser Met Ala Gly Tyr Gln Val Val Ala Ser Asp Gly His Glu
        35                  40                  45

Ala Leu Ala Met Phe Glu Gln Glu Ala Pro Asp Leu Ile Val Leu Asp
    50                  55                  60

Val Met Leu Pro Lys Leu Asp Gly Tyr Gly Val Cys Arg Glu Leu Arg
65                  70                  75                  80

Lys Leu Ser Asp Val Pro Ile Ile Met Leu Ser Ala Leu Gly Asp Ile
                85                  90                  95

Ala Asp Arg Ile Thr Gly Leu Asp Leu Gly Ala Asp Asp Tyr Leu Pro
            100                 105                 110

Lys Pro Phe Ser Pro Lys Glu Leu Glu Ala Arg Ile Ala Thr Ile Leu
        115                 120                 125

Arg Arg Leu Asp Asp Ser Pro Asn Ala Leu Ser Ala Pro Ser Ser Pro
    130                 135                 140

Gly Val Leu Arg Ile Ser Asp Val Glu Ile Asp Thr Asn Arg Arg Gln
145                 150                 155                 160

Val Phe Gln Arg Gly Glu Arg Val Pro Leu Thr Tyr Thr Glu Phe Ser
                165                 170                 175

Leu Leu Glu Leu Leu Phe Arg Gln Pro Gly Arg Val Val Pro Arg Ala
            180                 185                 190

Glu Ile Leu Glu Glu Leu Trp Gly Tyr Pro Pro Arg Arg Asn Ala Asp
        195                 200                 205

Leu Arg Val Val Asp Val Tyr Val Ala Arg Leu Arg Ser Lys Leu Glu
    210                 215                 220

Ala Asp Pro Arg Asn Pro Glu Leu Ile Ile Thr Val Arg Gly Thr Gly
225                 230                 235                 240

Tyr Thr Ser Gln Arg Leu Lys Asp Leu Pro Glu Ala Ala Gly Ala
                245                 250                 255
```

<210> SEQ ID NO 37
<211> LENGTH: 762
<212> TYPE: DNA
<213> ORGANISM: Arthrospira platensis

<400> SEQUENCE: 37

| | | | | | |
|---|---|---|---|---|---|
| atgaccataa | aagcacggct | tgacgaacgg | cgcaatcctg | aaaaaatcct | catcgccgat | 60 |
| gatgagtctg | caattcggcg | tattttgaca | acccgtctgt | caatggtcgg | ttacagtgtt | 120 |
| gtcgcagcag | cagatggctt | acaagctatt | gaaatgttcg | atcgcgaaag | tccagacctg | 180 |
| gtagttttgg | atgtaatgat | gccaagactt | aacggttacg | gggtttgtca | aaaaattcga | 240 |
| gaaatttctg | atattcccat | cattatgtta | accgccttgg | gagatgtagc | cgatcgcatt | 300 |
| accggtttag | aattgggggc | tgatgattac | ctcactaaac | cctttctcc | caaagaattg | 360 |
| gaagcccgca | ttcacgctat | cctccgtcgg | ttcaaagata | acgcatcttc | ccatgatcta | 420 |
| agtcccgaag | tcatccaagt | tgatactctc | cgcattgaca | ccattaaacg | acgggtttac | 480 |
| aaaggcgata | aattgttgcc | cctcacatat | atcgagttta | acttgctcga | actgttgttt | 540 |
| aagcgttctg | gtgaagcggt | ttctcgttcc | gaaattctgc | aacaattgtg | gggttacacc | 600 |
| ccccgccgca | ttgccgatat | gcgcgttgtt | gatgttcatg | tggctcgcct | acgagctaaa | 660 |
| attgagactg | atcagcgtaa | tcctgagtat | attctcacgg | ttcgcggtat | tggctactct | 720 |
| tcccagcgac | tcgcagcagt | ggaagaacca | attggcgcat | aa | | 762 |

<210> SEQ ID NO 38
<211> LENGTH: 253
<212> TYPE: PRT
<213> ORGANISM: Arthrospira platensis

<400> SEQUENCE: 38

Met Thr Ile Lys Ala Arg Leu Asp Glu Arg Arg Asn Pro Glu Lys Ile
1               5                   10                  15

Leu Ile Ala Asp Asp Glu Ser Ala Ile Arg Arg Ile Leu Thr Thr Arg
            20                  25                  30

Leu Ser Met Val Gly Tyr Ser Val Val Ala Ala Asp Gly Leu Gln
        35                  40                  45

Ala Ile Glu Met Phe Asp Arg Glu Ser Pro Asp Leu Val Val Leu Asp
    50                  55                  60

Val Met Met Pro Arg Leu Asn Gly Tyr Gly Val Cys Gln Lys Ile Arg
65                  70                  75                  80

Glu Ile Ser Asp Ile Pro Ile Ile Met Leu Thr Ala Leu Gly Asp Val
                85                  90                  95

Ala Asp Arg Ile Thr Gly Leu Glu Leu Gly Ala Asp Asp Tyr Leu Thr
            100                 105                 110

Lys Pro Phe Ser Pro Lys Glu Leu Glu Ala Arg Ile His Ala Ile Leu
        115                 120                 125

Arg Arg Phe Lys Asp Asn Ala Ser Ser His Asp Leu Ser Pro Glu Val
    130                 135                 140

Ile Gln Val Asp Thr Leu Arg Ile Asp Thr Ile Lys Arg Arg Val Tyr
145                 150                 155                 160

Lys Gly Asp Lys Leu Leu Pro Leu Thr Tyr Ile Glu Phe Asn Leu Leu
                165                 170                 175

Glu Leu Leu Phe Lys Arg Ser Gly Glu Ala Val Ser Arg Ser Glu Ile
            180                 185                 190

Leu Gln Gln Leu Trp Gly Tyr Thr Pro Arg Arg Ile Ala Asp Met Arg

```
            195                 200                 205
Val Val Asp Val His Val Ala Arg Leu Arg Ala Lys Ile Glu Thr Asp
    210                 215                 220

Gln Arg Asn Pro Glu Tyr Ile Leu Thr Val Arg Gly Ile Gly Tyr Ser
225                 230                 235                 240

Ser Gln Arg Leu Ala Ala Val Glu Glu Pro Ile Gly Ala
                245                 250

<210> SEQ ID NO 39
<211> LENGTH: 810
<212> TYPE: DNA
<213> ORGANISM: Procholorcoccus marinus

<400> SEQUENCE: 39
atgtatgaag aaggttcatc catgcttgag aagagcaatg atgggcccgg ttcaaaacct      60
gcctctctcc cttctgccac aatttttagtt gttgatgatg aaccagcagt tttaaaagtc    120
ttggttacca ggcttgagtt agcaggctat aaagttgttt cagcttcaga tggtgaagag    180
gctttagatg tttttcatag ggaaattcct gatcttgtcg ttcttgatgt aatgcttcct    240
aagcttgatg gctttgctgt atgtaggaga ttgcgagctg aatcaattgt cccgattatt    300
tttcttagtg ctcttgaagc aatatctgag cgagtagcgg gacttgactt gggtgctgat    360
gattatttat ctaaaccgtt tagtccaaaa gagcttgaag cacgtatagc cacaatattg    420
cgtagaatgg gtcctggcgc gtctgtagct gaacctagag agattcctgc tgggcaaggt    480
gtgatgaaac taggtgaatt agttgtggat acaaatcgtc gtcaggttag tcgcggtgga    540
gaaaggattg gtttaactta cacagagttt agtttgcttg aattactgtt tcgtgaccct    600
gggaaagtag ttcctagagc agagatactt gagcagctat ggggatatcc tcctaggcgt    660
gctgctgact aagagttgt tgacgtttat gtagcacgtt tgcgaggcaa gcttgagcca    720
gatcctcgta atccggagtt aattcttact gtaagaggca taggttattc atctcagagg    780
ttgaatgagt ttcctcctgt tagctcttaa                                       810

<210> SEQ ID NO 40
<211> LENGTH: 269
<212> TYPE: PRT
<213> ORGANISM: Procholorcoccus marinus

<400> SEQUENCE: 40

Met Tyr Glu Glu Gly Ser Ser Met Leu Glu Lys Ser Asn Asp Gly Pro
1               5                   10                  15

Gly Ser Lys Pro Ala Ser Leu Pro Ser Ala Thr Ile Leu Val Val Asp
                20                  25                  30

Asp Glu Pro Ala Val Leu Lys Val Leu Val Thr Arg Leu Glu Leu Ala
            35                  40                  45

Gly Tyr Lys Val Val Ser Ala Ser Asp Gly Glu Glu Ala Leu Asp Val
        50                  55                  60

Phe His Arg Glu Ile Pro Asp Leu Val Val Leu Asp Val Met Leu Pro
65                  70                  75                  80

Lys Leu Asp Gly Phe Ala Val Cys Arg Arg Leu Arg Ala Glu Ser Ile
                85                  90                  95

Val Pro Ile Ile Phe Leu Ser Ala Leu Glu Ala Ile Ser Glu Arg Val
            100                 105                 110

Ala Gly Leu Asp Leu Gly Ala Asp Asp Tyr Leu Ser Lys Pro Phe Ser
        115                 120                 125
```

```
Pro Lys Glu Leu Glu Ala Arg Ile Ala Thr Ile Leu Arg Arg Met Gly
    130                 135                 140

Pro Gly Ala Ser Val Ala Glu Pro Arg Glu Ile Pro Ala Gly Gln Gly
145                 150                 155                 160

Val Met Lys Leu Gly Glu Leu Val Val Asp Thr Asn Arg Arg Gln Val
                165                 170                 175

Ser Arg Gly Gly Glu Arg Ile Gly Leu Thr Tyr Thr Glu Phe Ser Leu
            180                 185                 190

Leu Glu Leu Leu Phe Arg Asp Pro Gly Lys Val Val Pro Arg Ala Glu
        195                 200                 205

Ile Leu Glu Gln Leu Trp Gly Tyr Pro Pro Arg Ala Ala Asp Leu
    210                 215                 220

Arg Val Val Asp Val Tyr Val Ala Arg Leu Arg Gly Lys Leu Glu Pro
225                 230                 235                 240

Asp Pro Arg Asn Pro Glu Leu Ile Leu Thr Val Arg Gly Ile Gly Tyr
                245                 250                 255

Ser Ser Gln Arg Leu Asn Glu Phe Pro Pro Val Ser Ser
            260                 265
```

```
<210> SEQ ID NO 41
<211> LENGTH: 20
<212> TYPE: PRT
<213> ORGANISM: Artificial sequence
<220> FEATURE:
<223> OTHER INFORMATION: DNA Encoding Guide RNA for transcriptional
      interference of the nblS gene in Synechococcus elongatus PCC7942

<400> SEQUENCE: 41

Thr Thr Gly Gly Cys Ala Ala Cys Ala Ala Cys Thr Gly Cys Gly Cys
1               5                   10                  15

Gly Ala Thr Ala
        20
```

```
<210> SEQ ID NO 42
<211> LENGTH: 20
<212> TYPE: RNA
<213> ORGANISM: Artificial sequence
<220> FEATURE:
<223> OTHER INFORMATION: Guide RNA for transcriptional interference of
      the nblS gene in Synechococcus elongatus PCC7942

<400> SEQUENCE: 42
uuggcaacaa cugcgcgaua                                               20
```

```
<210> SEQ ID NO 43
<211> LENGTH: 4107
<212> TYPE: DNA
<213> ORGANISM: Artificial sequence
<220> FEATURE:
<223> OTHER INFORMATION: DNA sequence to drive expression of the Cas9
      protein

<400> SEQUENCE: 43
atggataaga atactcaat aggcttagct atcggcacaa atagcgtcgg atgggcggtg     60
atcactgatg aatataaggt tccgtctaaa aagttcaagg ttctgggaaa tacagaccgc   120
cacagtatca aaaaaaatct tataggggct ctttttatttg acagtggaga gacagcggaa  180
gcgactcgcc tcaaacggac agctcgtaga aggtatacac gtcggaagaa tcgtatttgt   240
tatctacagg agatttttc aaatgagatg gcgaaagtag atgatagttt ctttcatcga   300
cttgaagagt ctttttttggt ggaagaagat aagaagcatg aacgtcatcc tattttttgga 360
```

```
aatatagtag atgaagttgc ttatcatgag aaatatccaa ctatctatca tctgcgaaaa    420
aaattggtag attctactga taaagcggat ttgcgcttaa tctatttggc cttagcgcac    480
atgattaagt ttcgtggtca tttttttgatt gagggagatt taaatcctga taatagtgat   540
gtggacaaac tatttatcca gttggtacaa acctacaatc aattatttga agaaaaccct    600
attaacgcaa gtggagtaga tgctaaagcg attctttctg cacgattgag taaatcaaga    660
cgattagaaa atctcattgc tcagctcccc ggtgagaaga aaaatggctt atttgggaat    720
ctcattgctt tgtcattggg tttgacccct aattttaaat caaattttga tttggcagaa    780
gatgctaaat tacagctttc aaaagatact tacgatgatg atttagataa tttattggcg    840
caaattggag atcaatatgc tgatttgttt ttggcagcta agaatttatc agatgctatt    900
ttactttcag atatcctaag agtaaatact gaaataacta aggctcccct atcagcttca    960
atgattaaac gctacgatga acatcatcaa gacttgactc ttttaaaagc tttagttcga   1020
caacaacttc cagaaaagta taagaaaatc ttttttgatc aatcaaaaaa cggatatgca   1080
ggttatattg atgggggagc tagccaagaa gaattttata aatttatcaa accaatttta   1140
gaaaaaatgg atggtactga ggaattattg gtgaaactaa atcgtgaaga tttgctgcgc   1200
aagcaacgga ccttttgacaa cggctctatt ccccatcaaa ttcacttggg tgagctgcat   1260
gctattttga aaggcaaga ggactttat ccattttttaa aagacaatcg tgagaagatt   1320
gaaaaaatct tgacttttcg aatcccttat tatgttggtc cattggcgcg tggcaatagt   1380
cgttttgcat ggatgactcg gaagtctgaa gaaacaatta ccccatggaa ttttgaagaa   1440
gttgtcgata aggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat taaagaaga ttatttcaaa aaaatagaat gttttgatag tgttgaaatt   1740
tcaggagttg aagatagatt taatgcttca ttagggacct accatgattt gctaaaaatt   1800
attaaagata agattttttt ggataatgaa gaaaatgaag atatcttaga ggatattgtt   1860
ttaacattga ccttatttga agatagggag atgattgagg aaagacttaa aacatacgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040 gatttttttga aatcagatgg ttttgccaat cgcaattta tgcagctgat ccatgatgat   2100
agtttgacat ttaaagaaga tattcaaaaa gcacaagtgt ctggacaagg cgatagttta   2160
catgaacata ttgcaaattt agctggtagc cctgctatta aaaaggtat tttacagact   2220 gtaaaagttg ttgatgaatt ggtcaaagta atggggcggc ataagccaga aaatatcgtt   2280
attgaaatgg cacgtgaaaa tcagacaact caaaagggcc agaaaaattc gcagagcgt    2340 atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatgcc   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
```

```
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta agtgattac cttaaaatct     2880 aaattagttt ctgacttccg aaaagatttc caattctata agtacgtga gattaacaat     2940 taccatcatg cccatgatgc gtatctaaat gccgtcgttg gaactgcttt gattaagaaa    3000
tatccaaaac ttgaatcgga gtttgtctat ggtgattata agtttatga tgttcgtaaa     3060 atgattgcta agtctgagca agaaataggc aaagcaaccg caaatatttt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc aagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aagggaaat cgaagaagtt aaaatccgtt    3480
aaagagttac tagggatcac aattatggaa agaagttcct ttgaaaaaaa tccgattgac    3540
tttttagaag ctaaaggata taggaagtt aaaaaagact taatcattaa actacctaaa    3600
tatagtcttt ttgagttaga aaacggtcgt aaacggatgc tggctagtgc cggagaatta    3660
caaaaaggaa atgagctggc tctgccaagc aaatatgtga ttttttata tttagctagt    3720 cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta acgatatac gtctacaaaa    4020 gaagttttag atgccactct tatccatcaa tccatcactg gtctttatga aacacgcatt    4080
gatttgagtc agctaggagg tgactaa                                         4107
```

<210> SEQ ID NO 44
<211> LENGTH: 1368
<212> TYPE: PRT
<213> ORGANISM: Artificial sequence
<220> FEATURE:
<223> OTHER INFORMATION: Cas9 protein

<400> SEQUENCE: 44

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110
```

-continued

```
His Glu Arg His Pro Ile Phe Gly Asn Ile Val Asp Glu Val Ala Tyr
            115                 120                 125
His Glu Lys Tyr Pro Thr Ile Tyr His Leu Arg Lys Lys Leu Val Asp
        130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
```

-continued

```
            530                 535                 540
Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                    565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                    645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                    725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                    805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                    885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960
```

```
Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                1000                1005

Val Tyr Gly Asp Tyr Lys Val Tyr Asp Val Arg Lys Met Ile Ala
         1010                1015                1020

Lys Ser Glu Gln Glu Ile Gly Lys Ala Thr Ala Lys Tyr Phe Phe
         1025                1030                1035

Tyr Ser Asn Ile Met Asn Phe Phe Lys Thr Glu Ile Thr Leu Ala
         1040                1045                1050

Asn Gly Glu Ile Arg Lys Arg Pro Leu Ile Glu Thr Asn Gly Glu
         1055                1060                1065

Thr Gly Glu Ile Val Trp Asp Lys Gly Arg Asp Phe Ala Thr Val
         1070                1075                1080

Arg Lys Val Leu Ser Met Pro Gln Val Asn Ile Val Lys Lys Thr
         1085                1090                1095

Glu Val Gln Thr Gly Gly Phe Ser Lys Glu Ser Ile Leu Pro Lys
         1100                1105                1110

Arg Asn Ser Asp Lys Leu Ile Ala Arg Lys Lys Asp Trp Asp Pro
         1115                1120                1125

Lys Lys Tyr Gly Gly Phe Asp Ser Pro Thr Val Ala Tyr Ser Val
         1130                1135                1140

Leu Val Val Ala Lys Val Glu Lys Gly Lys Ser Lys Lys Leu Lys
         1145                1150                1155

Ser Val Lys Glu Leu Leu Gly Ile Thr Ile Met Glu Arg Ser Ser
         1160                1165                1170

Phe Glu Lys Asn Pro Ile Asp Phe Leu Glu Ala Lys Gly Tyr Lys
         1175                1180                1185

Glu Val Lys Lys Asp Leu Ile Ile Lys Leu Pro Lys Tyr Ser Leu
         1190                1195                1200

Phe Glu Leu Glu Asn Gly Arg Lys Arg Met Leu Ala Ser Ala Gly
         1205                1210                1215

Glu Leu Gln Lys Gly Asn Glu Leu Ala Leu Pro Ser Lys Tyr Val
         1220                1225                1230

Asn Phe Leu Tyr Leu Ala Ser His Tyr Glu Lys Leu Lys Gly Ser
         1235                1240                1245

Pro Glu Asp Asn Glu Gln Lys Gln Leu Phe Val Glu Gln His Lys
         1250                1255                1260

His Tyr Leu Asp Glu Ile Ile Glu Gln Ile Ser Glu Phe Ser Lys
         1265                1270                1275

Arg Val Ile Leu Ala Asp Ala Asn Leu Asp Lys Val Leu Ser Ala
         1280                1285                1290

Tyr Asn Lys His Arg Asp Lys Pro Ile Arg Glu Gln Ala Glu Asn
         1295                1300                1305

Ile Ile His Leu Phe Thr Leu Thr Asn Leu Gly Ala Pro Ala Ala
         1310                1315                1320

Phe Lys Tyr Phe Asp Thr Thr Ile Asp Arg Lys Arg Tyr Thr Ser
         1325                1330                1335

Thr Lys Glu Val Leu Asp Ala Thr Leu Ile His Gln Ser Ile Thr
         1340                1345                1350
```

-continued

```
Gly Leu  Tyr Glu Thr Arg Ile  Asp Leu Ser Gln Leu  Gly Gly Asp
    1355             1360                 1365
```

What is claimed is:

1. A genetically-modified Cyanobacterium comprising an exogenous nucleotide sequence comprising SEQ ID NO: 23 that expresses an N-terminal fragment of RpaB polypeptide comprising the amino acid sequence of SEQ ID NO: 2, and wherein the N-terminal fragment does not comprise a DNA binding domain or a functional DNA binding domain, under the control of a promoter that results in down-regulated RpaB pathway activity in the genetically-modified Cyanobacterium as compared to a Cyanobacterium of the same species without the exogenous nucleotide sequence.

2. The genetically-modified Cyanobacterium of claim 1 wherein the promoter is
   (a) an inducible promoter; or
   (b) endogenous to the genome of the genetically-modified Cyanobacterium.

3. The genetically-modified Cyanobacterium of claim 1 wherein the genetically-modified Cyanobacterium is a Cyanobacterium selected from *Synechococcus elongatus, Arthrospira maxima, Arthrospira platensis*, and *Cyanobacterium aponinum*.

4. The genetically-modified Cyanobacterium of claim 1 wherein the genetically-modified Cyanobacterium has increased
   (a) photosynthetic capacity as compared to a Cyanobacterium of the same species without the exogenous nucleotide sequence; and/or
   (b) photosynthetic biomass accumulation from photoautotrophic growth as compared to a Cyanobacterium of the same species without the exogenous nucleotide sequence.

* * * * *